United States Patent
Hunziker

(10) Patent No.: US 11,759,653 B2
(45) Date of Patent: Sep. 19, 2023

(54) IMAGE GUIDED LASER THERAPY

(71) Applicant: Cutera, Inc., Brisbane, CA (US)

(72) Inventor: Lukas Hunziker, San Jose, CA (US)

(73) Assignee: CUTERA, INC., Brisbane, CA (US)

(*) Notice: Subject to any disclaimer, the term of this patent is extended or adjusted under 35 U.S.C. 154(b) by 0 days.

(21) Appl. No.: 17/677,974

(22) Filed: Feb. 22, 2022

(65) Prior Publication Data
US 2023/0064129 A1 Mar. 2, 2023

Related U.S. Application Data

(63) Continuation of application No. 17/576,902, filed on Jan. 14, 2022.
(Continued)

(51) Int. Cl.
| *A61N 5/067* | (2006.01) |
| *G16H 30/40* | (2018.01) |
| *A61B 90/00* | (2016.01) |
| *A61N 5/06* | (2006.01) |
| *G16H 20/40* | (2018.01) |
| *A61B 17/00* | (2006.01) |

(Continued)

(52) U.S. Cl.
CPC ............ *A61N 5/067* (2021.08); *A61B 90/361* (2016.02); *A61N 5/0616* (2013.01); *G16H 20/40* (2018.01); *G16H 30/40* (2018.01); *A61B 2017/00061* (2013.01); *A61B 2017/00154* (2013.01); *A61B 2018/00904* (2013.01); *A61B 2018/20351* (2017.05)

(58) Field of Classification Search
CPC ........ A61N 5/06; A61N 5/0616; A61N 5/062; A61N 2005/0626; A61N 2005/0642–0644; A61N 2005/065; A61N 5/067; A61B 2018/00904; A61B 2018/20351; A61B 2018/20353; A61B 90/36; A61B 90/361; G16H 30/40
USPC .................. 607/88, 96, 104; 128/898; 362/3
See application file for complete search history.

(56) References Cited

U.S. PATENT DOCUMENTS

| 5,543,870 A | 8/1996 | Blanchard |
| 5,582,703 A | 12/1996 | Sluzky et al. |

(Continued)

FOREIGN PATENT DOCUMENTS

| WO | 2020003138 A1 | 1/2020 |
| WO | 2020003138 A1 | 2/2020 |

OTHER PUBLICATIONS

Welch, A. J. (2011), Optical-thermal response of laser-irradiated tissue, 2nd edition, Springer Science+Business, Media, pp. 53-54.

(Continued)

*Primary Examiner* — Ahmed M Farah
(74) *Attorney, Agent, or Firm* — Timothy L. Scott, Esq.

(57) ABSTRACT

Systems, devices, and methods for treating a skin of a patient with therapeutic laser light via imaging a first skin area of the patient to obtain at least a first image, processing the at least a first image of the first skin area with at least one processor to identify within the first skin area at least one or more target skin areas and a non-target skin area, generating a treatment map of the first skin area based on the identified one or more target skin areas and the non-target skin area, and treating at least a portion of the one or more target skin areas with therapeutic laser light based on the generated treatment map.

28 Claims, 23 Drawing Sheets

Related U.S. Application Data

(60) Provisional application No. 63/238,126, filed on Aug. 28, 2021.

(51) Int. Cl.
*A61B 18/00* (2006.01)
*A61B 18/20* (2006.01)

(56) References Cited

U.S. PATENT DOCUMENTS

| | | | |
|---|---|---|---|
| 5,594,561 A | 1/1997 | Blanchard | |
| 5,626,410 A | 5/1997 | Chambers et al. | |
| 5,640,479 A | 6/1997 | Hegg et al. | |
| 6,258,081 B1 | 7/2001 | Festag et al. | |
| 6,328,733 B1 | 12/2001 | Trost | |
| 6,451,010 B1 | 9/2002 | Angeley | |
| 6,511,475 B1 | 1/2003 | Altshuler et al. | |
| 6,532,244 B1 | 3/2003 | Dewey et al. | |
| 6,616,275 B1 | 9/2003 | Dick et al. | |
| 6,726,679 B1 | 4/2004 | Dick et al. | |
| 6,848,790 B1 | 2/2005 | Dick et al. | |
| 6,887,233 B2 | 5/2005 | Angeley et al. | |
| 7,066,930 B2 | 6/2006 | Boll et al. | |
| 7,077,840 B2 | 7/2006 | Altshuler et al. | |
| 7,220,254 B2 | 5/2007 | Altshuler et al. | |
| 7,263,255 B2 | 8/2007 | Andersen et al. | |
| 7,309,335 B2 | 12/2007 | Altshuler et al. | |
| 7,438,713 B2 | 10/2008 | Angeley et al. | |
| 7,758,621 B2 | 7/2010 | Altshuler et al. | |
| 7,824,396 B2 | 11/2010 | Angeley et al. | |
| 7,935,107 B2 | 5/2011 | Altshuler et al. | |
| 8,109,924 B2 | 2/2012 | Altshuler et al. | |
| 8,190,243 B2 | 5/2012 | Welches et al. | |
| 8,275,442 B2 | 9/2012 | Allison | |
| 8,475,507 B2 | 7/2013 | Dewey et al. | |
| 8,526,108 B2 | 9/2013 | Weinold et al. | |
| 8,702,769 B2 | 4/2014 | Eckhouse et al. | |
| 8,783,873 B2 | 7/2014 | Weinold et al. | |
| 8,845,630 B2 | 9/2014 | Mehta et al. | |
| 8,882,753 B2 | 11/2014 | Mehta et al. | |
| 9,017,316 B2 | 4/2015 | Khatchaturov et al. | |
| 9,066,738 B2 | 6/2015 | Mehta et al. | |
| 9,226,917 B2 | 1/2016 | Strong et al. | |
| 9,301,681 B2 | 4/2016 | Ha et al. | |
| 9,717,629 B2 | 10/2017 | Anderegg | |
| 9,962,079 B2 | 5/2018 | Carmeli et al. | |
| 9,974,436 B2 | 5/2018 | Ha et al. | |
| 10,045,820 B2 * | 8/2018 | Youngquist | G16H 20/40 |
| 10,092,446 B2 | 10/2018 | Anderegg | |
| 10,327,636 B2 | 6/2019 | Ha et al. | |
| 10,420,676 B2 | 9/2019 | Kim | |
| 10,492,862 B2 | 12/2019 | Domankevitz | |
| 10,495,490 B2 | 12/2019 | Waisman et al. | |
| 10,507,135 B2 | 12/2019 | Ha et al. | |
| 10,575,987 B2 | 3/2020 | Ha | |
| 10,588,781 B2 | 3/2020 | Kim et al. | |
| 2003/0036751 A1 | 2/2003 | Anderson et al. | |
| 2005/0154382 A1 * | 7/2005 | Altshuler | A61B 90/30 606/9 |
| 2009/0024023 A1 | 1/2009 | Welches et al. | |
| 2015/0230863 A1 * | 8/2015 | Youngquist | A61B 18/203 606/9 |
| 2016/0035079 A1 | 2/2016 | Tenney et al. | |
| 2016/0317226 A1 * | 11/2016 | Jagdeo | A61B 90/06 |
| 2021/0186610 A1 | 6/2021 | Zuo et al. | |
| 2021/0220667 A1 | 7/2021 | Schuster et al. | |

OTHER PUBLICATIONS

Wolff, K., et al.,(2017), Fitzpatrick's color atlas and synopsis of clinical dermatology, 7th edition, New York: McGraw-Hill Education, pp. 164-167 and 215-218.

Yakimov, B. P. et al.,(2020), Melanin distribution from the dermal-epidermal junction to the stratum corneum: Non-invasive in vivo assessment by fluorescence and Raman microspectroscopy. Scientific Reports, 10(1). doi:10.1038/s41598-020-71220-6, 13 pages.

Altshuler, G., (2001), Extended theory of selective photothermolysis. Lasers in Surgery and Medicine, 29(5), 416-432. doi:10.1002/lsm.1136.

International Search Report and Written Opinion dated Dec. 7, 2022, PCT Application No. PCT/US2022/041775 filed Aug. 27, 2022.

PCT Search Report and Written Opinion dated Dec. 7, 2022, International Patent Application No. PCT/US2022/041775 filed Aug. 27, 2022.

* cited by examiner

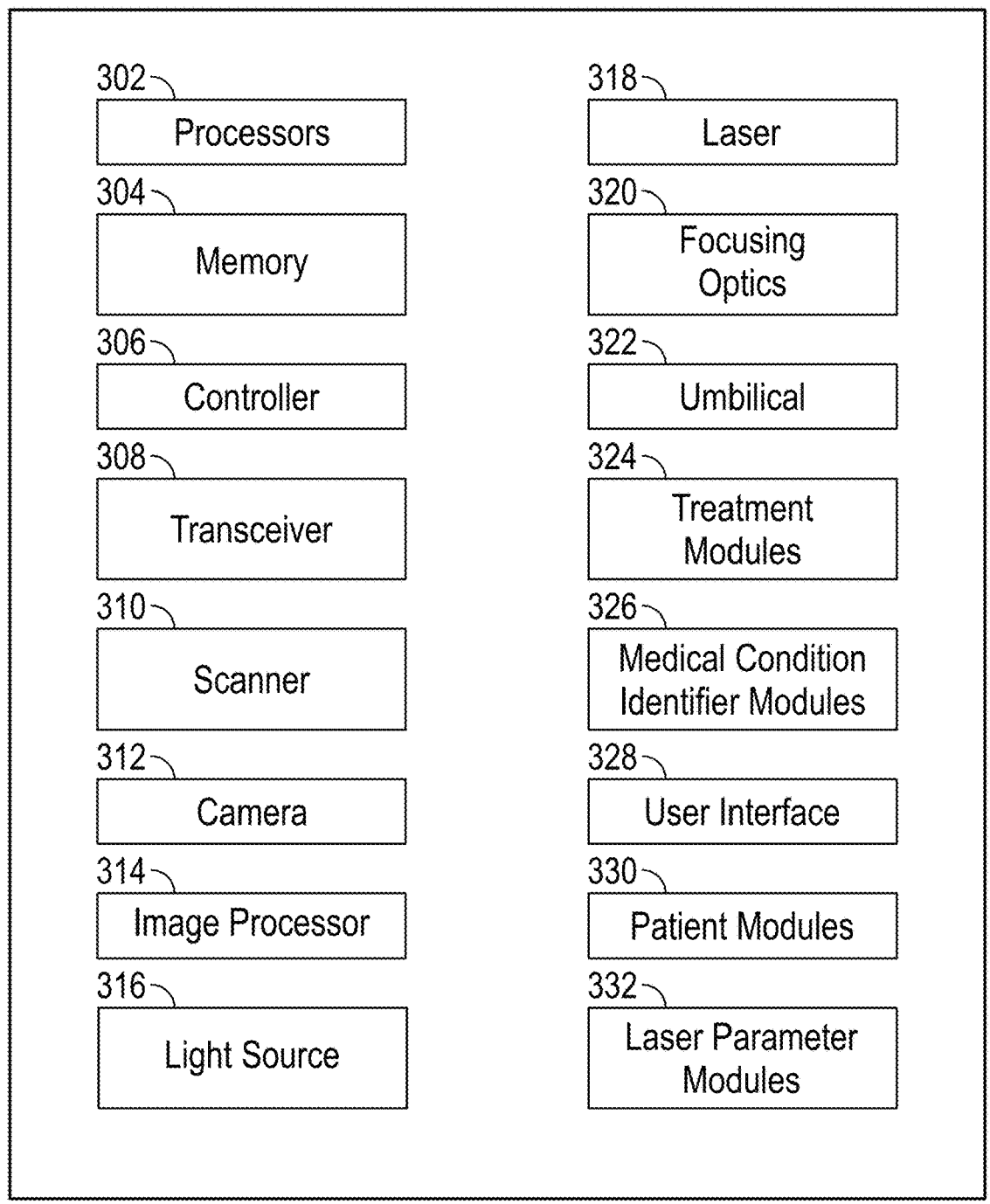
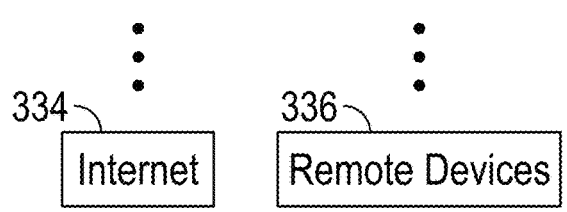
FIG. 3

2000

2002
Initiate a first laser treatment procedure with a first set of laser pulse parameters on one or more target skin areas 2004
Initiate a second laser treatment procedure with a second set of laser pulse parameters on the one or more target skin areas 2006
Initiate an $N^{th}$ laser treatment procedure with an $N^{th}$ set of laser pulse parameters on the one or more target skin areas

2102
Initiate a first laser treatment procedure with a first set of laser pulse parameters on a first portion of the one or more target skin areas during a first portion of the treatment 2104
Initiate a second laser treatment procedure with a second set of laser pulse parameters on a second portion of the one or more target skin areas during a second portion of the treatment 2106
Initiate an $N^{th}$ laser treatment procedure with an $N^{th}$ set of laser pulse parameters on an $N^{th}$ portion of the one or more target skin areas during an $N^{th}$ portion of the treatment

FIG. 21

IMAGE GUIDED LASER THERAPY

REFERENCE TO RELATED APPLICATION

The present application is a continuation of U.S. patent application Ser. No. 17/576,902, filed Jan. 14, 2022, entitled "Image Guided Laser Therapy," which claims priority to U.S. Provisional Patent Application No. 63/238,126 filed Aug. 28, 2021. This application claims the benefit of priority to both of the foregoing applications, each of which is hereby incorporated by reference in its entirety.

BACKGROUND OF THE DISCLOSURE

This disclosure relates generally to medical devices and more particularly, to methods, apparatus, and systems for treating lesions or other medical and/or dermatological conditions using laser energy.

DESCRIPTION OF THE RELATED ART

Currently, commercial laser-based skin treatment systems typically utilize a spot size of 2 to 5 millimeters (mm) to treat many types of skin lesions.

Utilizing such current commercial systems, laser treatment of skin lesions can be a lengthy and time-consuming process that requires significant operator skill to diagnose lesions, select appropriate laser treatment parameters, and manually position the laser hand piece to apply a sequence of laser pulses of the specified spot size and parameters to the lesion. For example, a typical patient may have 10 to 30 facial lesions, each of which needs to be diagnosed individually to determine appropriate treatment parameters, and the laser beam from the hand piece needs to be manually and sequentially aligned to each lesion with a precision of about 1 mm to apply the laser treatment pulses. This process requires a high degree of skill from the system operator, and even relatively skilled operators may overtreat or undertreat significant skin areas, including both target skin areas such as a lesion or portion thereof, or non-lesion areas for which no treatment is desired, but which are treated either by error or because the laser spot size cannot be limited to only the target (e.g., lesion) area.

SUMMARY OF THE DISCLOSURE

In one aspect, the present disclosure relates to systems, devices, and/or methods of treating lesions or other medical events with a guided laser therapy.

In another aspect, the present disclosure relates to systems, devices, and/or methods that utilize a procedure for mapping out treatment and non-treatment areas.

In another aspect, the present disclosure relates to systems, devices, and/or methods that determine one or more treatment parameters which may or may not be based on one or more characteristics of one or more treatment areas.

In another aspect, the present disclosure relates to systems, devices, and/or methods that determine one or more treatment sequences which may or may not be based on one or more characteristics of one or more treatment areas.

In another aspect, the present disclosure relates to systems, devices, and/or methods that utilize one or more multi-factorial confluent treatments.

In another aspect, the present disclosure relates to systems, devices, and/or methods that utilize one or more multi-factorial fractional treatments.

In another aspect, the present disclosure relates to systems, devices, and/or methods that determine a treatment handpiece's velocity and/or the time data.

In another aspect, the present disclosure relates to systems, devices, and/or methods for mapping target and non-target areas within a skin area of a patient, and providing an automated treatment process to selectively maximize and optimize the treatment of target areas and minimize treatment of non-target areas.

BRIEF DESCRIPTION OF THE DRAWINGS

The disclosure may be understood by reference to the following description taken in conjunction with the accompanying drawings in which:

FIG. 3 is a block diagram, according to one embodiment;

FIG. 20 is a treatment flow chart, according to one embodiment;

FIG. 21 is a treatment flow chart, according to one embodiment;

Figure 1:
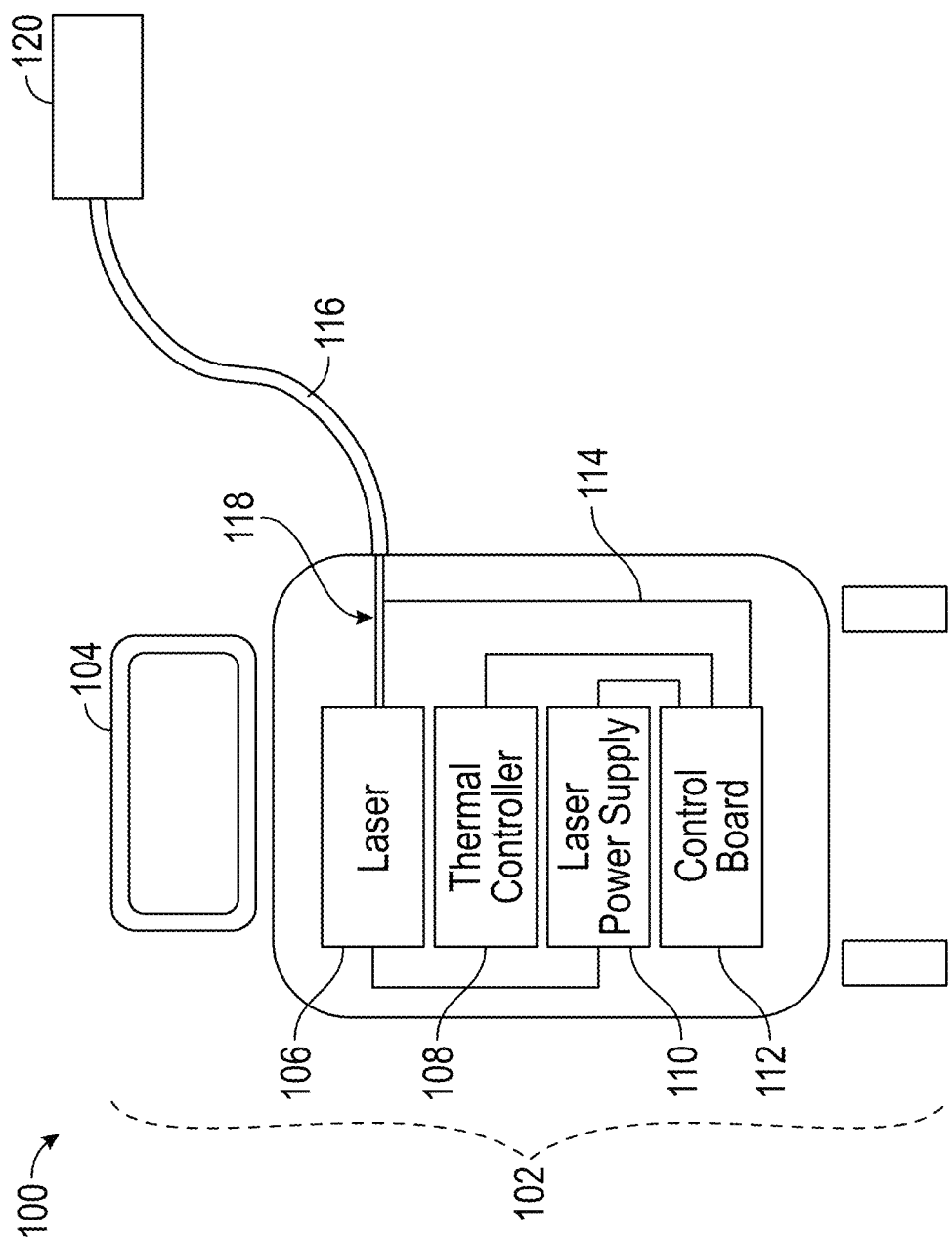
FIG. 1 is an illustration of a laser skin treatment system, according to one embodiment.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure.

DETAILED DESCRIPTION OF SPECIFIC EMBODIMENTS

Illustrative embodiments of the disclosure are described herein. For clarity, not all features of an actual implementation are provided in detail. In any actual embodiment, numerous implementation-specific decisions must be made to achieve the design-specific goals. Such a development effort, while possibly complex and time-consuming, would nevertheless be a routine task for persons of skill in the art given this disclosure.

This application does not intend to distinguish between components that differ in name but not function. "Including" and "includes" are used in an open-ended fashion, and should be interpreted to mean "including, but not limited to." "Couple" or "couples" are intended to mean either a direct or an indirect electrical connection. "Or" is used in the inclusive sense (i.e., "and/or") unless a specific use to the contrary is explicitly stated.

As used herein, "target skin area" refers to an area of skin to be treated as a unit for purposes of receiving one or more laser pulses (e.g., as a therapy or treatment for a skin condition) in at least a portion thereof. In embodiments of the present disclosure, a target skin area comprises an area determined or identified from an image of a larger skin area that includes both target skin areas (at least a portion of which is intended to be treated with one or more laser pulses) and non-target skin areas not identified/intended to be treated with laser pulses. A target skin area may comprise an area for which all or substantially all of the area is intended to receive laser pulses, or an area that is to be treated by applying laser pulses to only a portion or fraction of the total area (e.g., a fractional treatment comprising a predetermined percentage of the total area of the target skin area) but which is considered as a unit for consideration of which portions of the whole are to receive laser pulses. Thus, a target skin area may include areas of skin that do not receive laser pulses as part of a treatment, in contrast to non-target skin areas, for which no portion is intended to receive laser pulses. As used herein, "confluent treatment" is defined as a treatment where the laser spots are nominally contiguous. As used herein, "fractional treatment" is defined as a treatment where the laser spots are spaced by some nominal amount.

In FIG. 1, an illustration of a laser skin treatment system 100 is shown, according to one embodiment. The laser skin treatment system 100 may include a console 102, a user interface 104, a laser 106, a thermal controller 108, a laser power supply 110, a control board 112, one or more communication lines 114, an umbilical 116, an optical delivery system 118, and/or a hand-held handpiece 120. In one example, the thermal controller 108 and the control board 112 and/or any other controller may be a single controller.

Further, the controller in FIG. 3 may be one or more controllers. The disclosure relates to the use of a camera and illumination system to capture an image of a selected area of skin (or one or more images of one or more potential treatment areas) for laser treatment of skin lesions within the selected area, using a software algorithm and image processor to create one or more 2-dimensional spatial maps of lesions within the image, and then using these maps to perform automated or user-guided, spatially selective treatment of the lesions with a laser (See FIG. 2). In one embodiment, lesions within the image comprise target skin areas to be treated with the laser, while non-lesion areas comprise non-target areas for which laser treatment is not desired.

The treatment is provided by a laser system that is comprised of the console 102 and the hand-held device 120 that is coupled to the console 102 by the umbilical 116. As shown in FIG. 1, the console 102 contains the laser 106, the laser power supply 110 and thermal management systems (e.g., thermal controller 108) to drive the laser 106. Further, the system 100 may include a user interface 104 (e.g., a graphical user interface) with controls for allowing the user to operate and/or modify the system 100, a master control board with a CPU 112 that provides overall control and coordination of all system 100 operations, and an electrical interface (not shown) to the umbilical 116 to provide power and communication to the hand piece 120. Laser emission is directed from the laser 106 through an optical delivery system that is part of the umbilical 116, such as a fiber, articulated arm, or other optical coupling systems or components. The laser 106 may be a diode laser, fiber laser, DPSS laser or another type of laser with emission in the visible, near-infrared, or mid-infrared portion of the electromagnetic spectrum, depending on the requirements of the application and/or the skin condition(s) to be treated.

Figure 2:
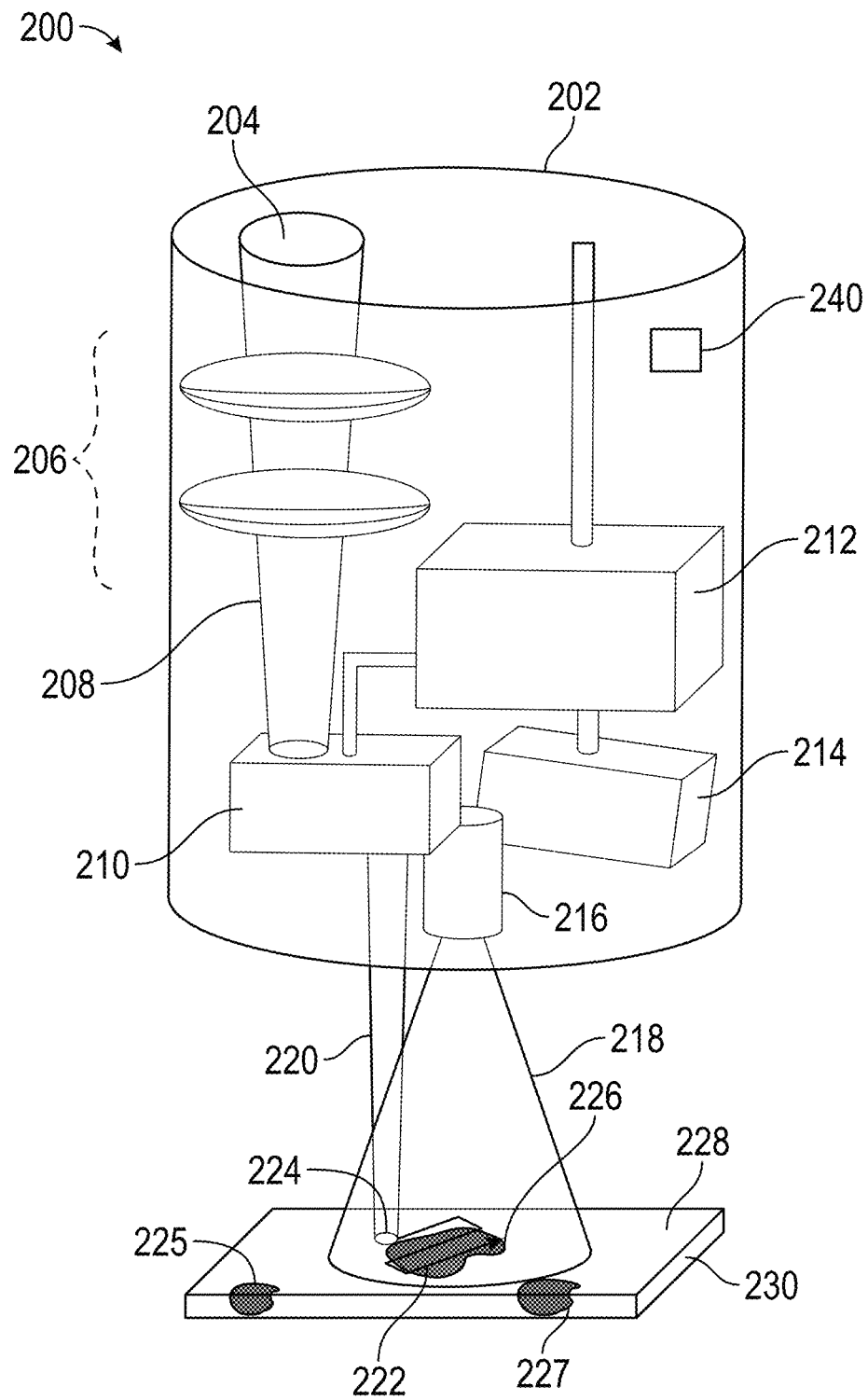
FIG. 2 is another illustration of a laser skin treatment system, according to one embodiment.

In FIG. 2, another illustration of a portion of a treatment system is shown, according to one embodiment. As shown in FIG. 2, a handheld device 200 (e.g., a handpiece) may include a scanner device 210 (e.g., a movable mirror driven by an electric motor for directing the laser light to a portion of a target skin area), an image processor 212, a camera 214, an illumination source 216, electronics, and optical elements 206 that focus a laser beam 220 to a desired portion of a target area 224 (e.g., a small spot) on the skin surface. In another example, the handheld device 200 may include an umbilical interface 202, a laser input area 204, focusing optics 206, a laser beam 208 moving through the focusing optics 206, the scanner device 210, the image processor 212, the camera 214, and/or the light source 216 (e.g., LEDs, etc.). In this example, the handheld device 200 has main internal elements, including laser beam optical elements 206, a scanner 210, a camera 214, and an LED illumination source 216, and image processor 212. The handheld device 200 may interact with a skin area 230 using scanner 210 to direct laser beam 220 along a scan path 222 to treat a target skin area 224 (e.g., one or more spots, as shown at 224, located along scan path 222) in coordination with images from image processor 212 captured by camera 214 having a field of view 218 illuminated by illumination source 216. In one example, scan path 222 may be determined by image processor 212 so as to treat all or part of a pigmented lesion 225, 226, 227 (and/or any other medical condition) located in an imaged or selected skin area 228 which includes both target skin areas (e.g., 225, 226, 227) to be treated and non-target areas to be left untreated. In addition, handheld device 200 may include a location tracking device 240, which may provide locational data (e.g., 3D coordinates)

and/or movement data (e.g., velocity, acceleration, angle, etc.) as the handheld device 200 is moved, preferably at a high data sampling rate (e.g., 1000-10,000 Hz or greater) to ensure that scanner 210 can maintain the laser beam 220 at a desired treatment location and/or move to a desired sequence of treatment locations along scan path 222 even in the presence of movement (whether intentional or unintentional) of handheld device 200 by a user.

In one example, camera 214 may contain a lens system (not shown) that projects an image of the treatment plane onto an image sensor and/or optical filters that block background light from the sensor. The lens system may employ one or more lenses (e.g., from 2 to 6 lenses) to provide the desired combination of a working distance, field of view, and spatial resolution, to enable the system to control movement of scanner 210 to apply laser light (e.g., one or more pulses at spots 224 along scan path 222) to a target skin area such as a lesion 226. The image sensor may be a CMOS or CCD sensor with 1 to 20 million pixels or more, depending on the desired spatial resolution. Camera 214 and/or image processor 212 may include optical filters to capture image data under desired lighting conditions based on, e.g., wavelength, polarization, or other factors depending on the application. The light source 216 may contain optical emitters such as LEDs that illuminate the selected or imaged area containing target and non-target skin areas.

In various embodiments, light source 216 may provide light in the ultra-violet (UV), visible, or infrared (e.g., near infrared or NIR, mid-infrared or MIR, or far-infrared or FIR) using LEDs or other optical emitters, and may be used in concert with corresponding passband filters to increase the contrast of one or more lesion types in the processed images. For example, UV light is absorbed much more strongly by pigmented lesions than visible or near-IR light. Therefore, pigmented lesions will appear much darker and with greater contrast when illuminated by UV light and captured by an image sensor through a UV passband filter. Similarly, a near-IR illumination source and filter will increase the contrast for vascular lesions. Depending upon the types of skin conditions/lesion treated, a combination of ambient light, UV light, IR light, and/or any other light source may be utilized in various embodiments.

FIG. 3 shows a block diagram 300 of a system for providing image-based laser treatment for one or more target skin areas, according to one embodiment. The block diagram 300 identifies certain components or subsystems of embodiments such as those of FIGS. 1 and 2. Systems of the present disclosure may include one or more processors 302, a memory 304, one or more controllers 306, a transceiver 308, a scanner 310 (e.g., a movable device such as a mirror for directing laser treatment pulse(s) to target skin area(s)s within an imaged skin area), an imaging device 312 (e.g., a camera), an image processor 314, one or more light sources 316, one or more laser sources 318, focusing optics 320, an umbilical 322, one or more treatment modules 324, one or more medical condition identifier modules 326, a user interface 328, one or more patient modules 330, and/or one or more laser parameter modules 332.

In one embodiment, the system described by block diagram 300 may communicate via the Internet 334 (or another communications channel such as cellular communication) to one or more remote devices 336. In another embodiment, the system of block diagram 300 may communicate to remote devices without the Internet 334 (e.g., by direct or wire connection). In one example, the one or more treatment modules 324 may include treatment data, parameter data, treatment results, treatment patterns, and/or any other information relating to one or more treatments to be provided to a target skin area. In another example, the one or more medical condition identifier modules 326 may include vascular lesion data, pigmented lesion data, remodeling data, collagen data, and/or any other medical condition identifier data disclosed herein or apparent to persons of skill the art in view of this disclosure. The medical condition identifier module(s) 326 may be used in processing captured images to identify target skin areas associated with a medical condition, and/or to determine treatment parameters therefor.

In one example, systems of the present disclosure may image a tattoo area on a patient's skin, and process the image(s) to determine laser light fluences, frequencies (e.g., 532, 760, or 1064 nm, or other wavelengths), or other parameters to provide optimized treatment (e.g., on a pixel-by-pixel basis) to remove the tattoo based on color and color intensity in the processed image(s). In another example, a user interface 328 may include one or more user interfaces to display captured images, treatment maps (created by algorithm and/or as modified by a user), before treatment and after treatment results, one or more recommended procedures, and/or any other user display information disclosed herein. In another example, the one or more patient modules 330 may include any patient data disclosed herein or apparent to persons of skill in the art. In another example, the one or more laser parameter modules 332 may include any laser parameter and/or treatment parameters described herein or apparent to persons of skill in the art.

Figure 4:
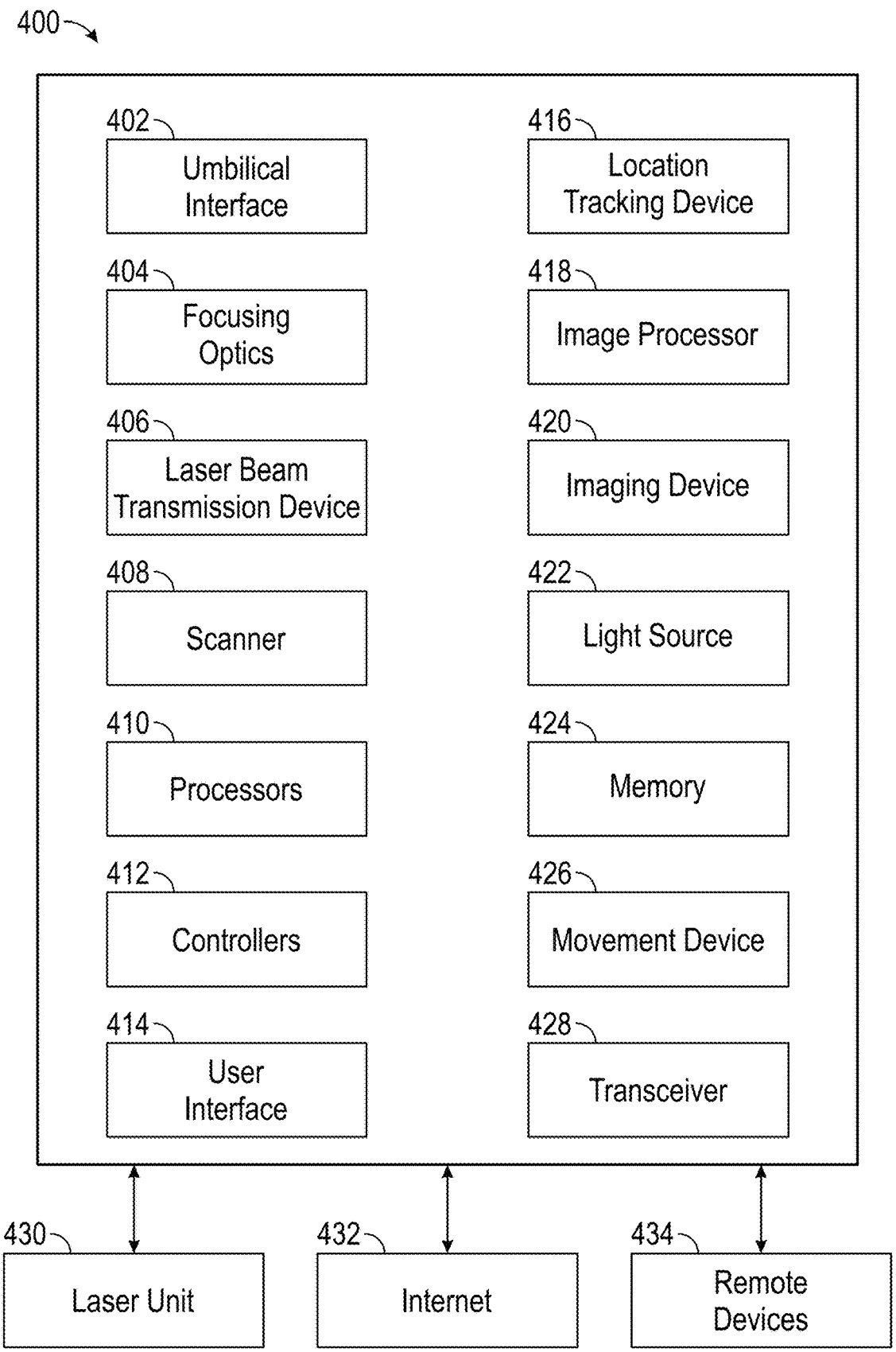
FIG. 4 is a block diagram, according to one embodiment.

FIG. 4 shows a block diagram according to another embodiment, identifying features, components, or subsystems that may be present in a handheld device 400 according to one embodiment herein embodiments herein. Handheld device 400 may be coupled to a laser unit 430 that provides laser light for delivery to target skin area(s), and may be coupled to the internet 432 or to remove devices 434 (e.g., a computer such as a handheld device or phone). Handheld device 400 may include an umbilical interface 402; focusing optics 404 for applying laser light to the target skin area(s); a laser beam transmission device 406; a scanner 408 (e.g., a movable mirror driven by a motor for applying laser light to a target skin area within an imaged skin area); one or more processors 410; one or more controllers 412; a user interface 414; a location tracking device 416 for tracking the location of the handpiece and/or the skin area to which laser light is directed; one or more image processors 418; an imaging device 420 (e.g., a camera); one or more light sources 422; a memory 424; a movement device 426 for determining the movement of the handpiece 400; and a transceiver 428. Each and every component disclosed herein may be provided in a handpiece according to this disclosure, and each and every component may be considered optional and omitted or provided separately from handheld device 400.

Figure 5A:
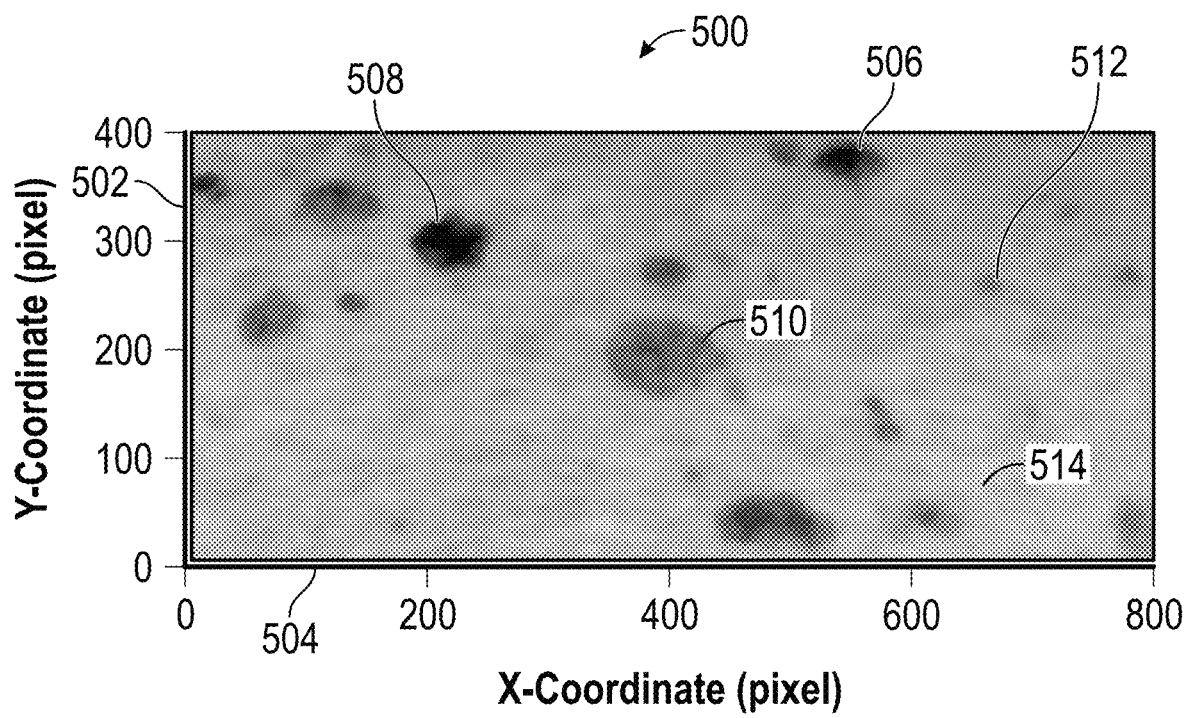
FIGS. 5A-5D are illustrations of a treatment mapping procedure for one or more target skin areas within a first skin area, according to one embodiment.
Figure 5B:
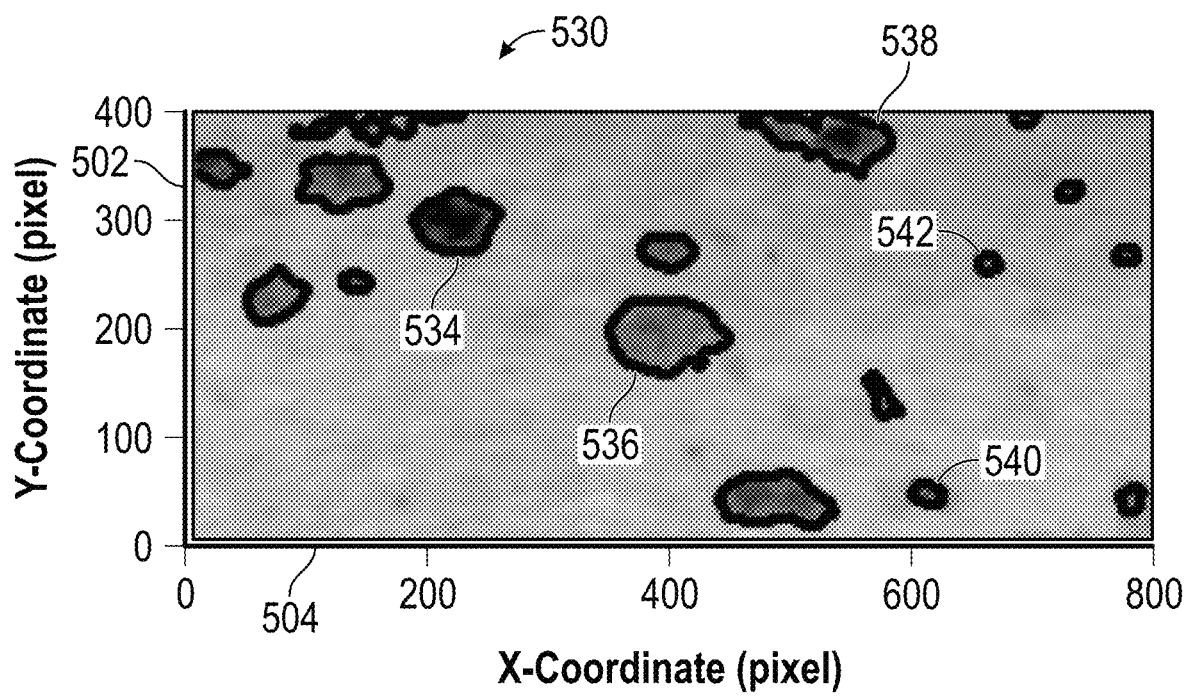
Figure 5C:
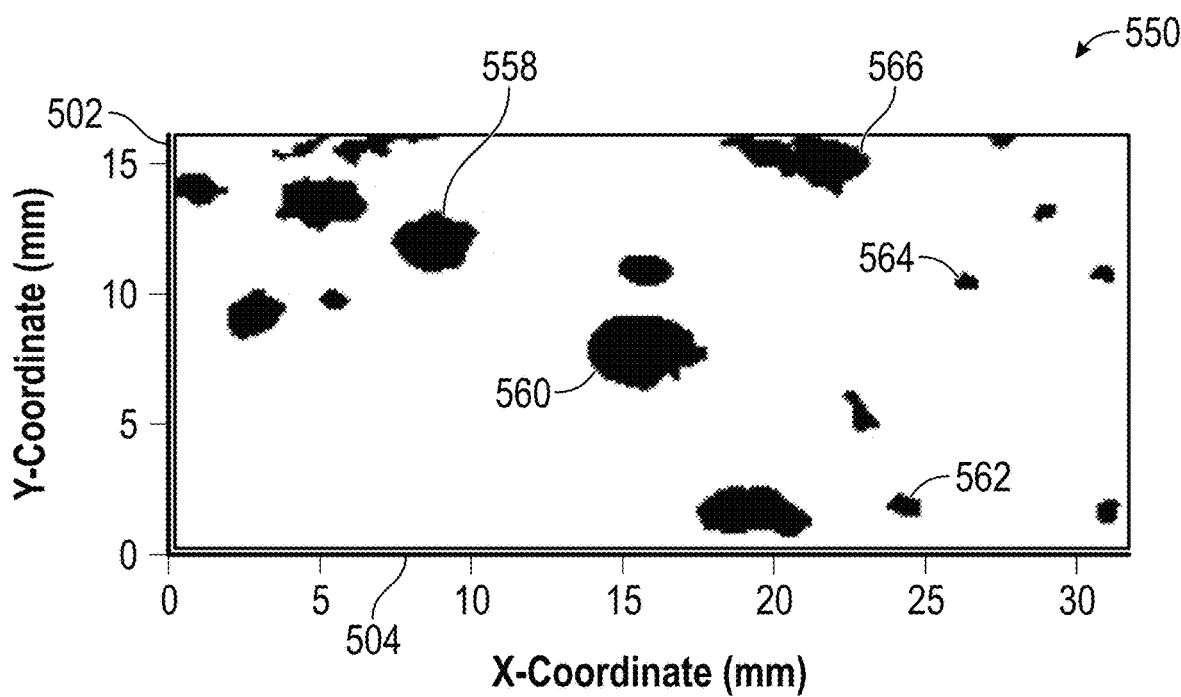

In FIGS. 5A-D, illustrations of a treatment mapping procedure for one or more selected or imaged skin areas (e.g., target skin areas within non-treatment areas) are shown, according to one embodiment. After an image is recorded, the recorded image is passed to an image processor (e.g. image processor 212, FIG. 2), which applies an image processing algorithm that processes the image to identify and locate lesions and their boundaries within the imaged skin area. In one embodiment, this may involve performing a segmentation algorithm on the image. FIG. 5A and FIG. 5B show images of an area of skin having pigmented skin lesions before and after processing of the captured image using an image segmentation algorithm, respectively. FIG. 5B shows the boundaries of a plurality of target skin areas in the selected (imaged) skin area shown in the figure, with the remaining portions being non-target areas to receive no laser treatment. In some embodiments, the boundaries shown in FIG. 5B may assist a user in visualizing or confirming all of the target skin areas identified by the processing algorithm in the imaged area. In alternative embodiments, the boundaries may be omitted. The image processing algorithm can in one embodiment classify each pixel in the image as healthy or lesion tissue and use the pixel data to create a map of all target skin areas to be treated. In the embodiment shown in FIG. 5B, this includes identifying the boundaries of each lesion area, as well as non-lesion areas comprising non-target areas for which no treatment is to be provided. FIG. 5C illustrates an example of a treatment map after rescaling the image from pixel coordinates to spatial coordinates in the treatment plane.

Figure 5D:
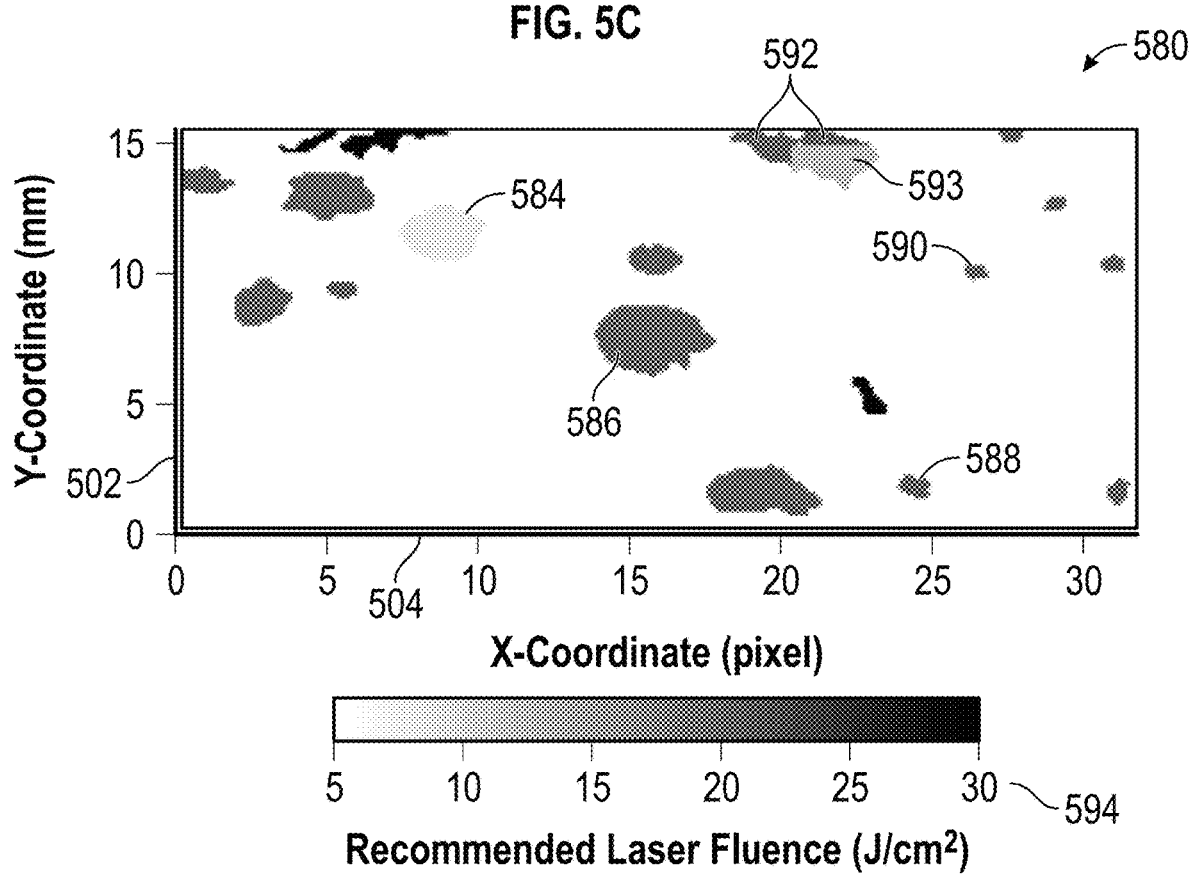

In one embodiment, the image processing algorithm may analyze the image data in several ways to determine optimum laser parameters for treating each lesion area or sub-area at a desired level of detail, which may extend to the pixel-level of the processed image. For example, the algorithm may create a shaded (e.g., grayscale or color-coded) image in which the darkness or color of a lesion, or a sub-area within a lesion, may indicate the density of the target chromophore present. The shaded image may in turn be used to determine the laser fluences that will achieve the maximum therapeutic effect without overtreatment. An example of a map of recommended laser fluence settings, as determined by one embodiment of the image-processing algorithm, is shown in FIG. 5D. Different lesions (or different sub-areas within a single lesion) are depicted in FIG. 5D as lighter or darker than other lesions or lesion sub-areas, and the grayscale or color classification for each pixel (or group of pixels in some embodiments) may be used in the algorithm to determine laser fluences for the therapeutic laser pulses to treat each target skin area (e.g., lesion) or portion thereof. In addition to fluence values, the algorithm may also determine one or more additional treatment parameters for a lesion area or sub-area, such as laser power, pulse width, beam diameter/spot size, etc., to determine not only optimum treatment parameters for the target lesion area or sub-area, but also to minimize undesired treatment (i.e., exposure to laser light) of non-target areas.

FIGS. 5A-5D collectively are an example of one image processing sequence for pigmented lesions. In FIG. 5A, an image of a selected skin area comprising treatment and non-treatment areas obtained from an image sensor is shown before the image is processed. FIGS. 5B-5D show different processed versions of the image of FIG. 5A according to various embodiments. In FIG. 5B, a projection of lesion boundaries onto the image, as determined by an image processing algorithm, is shown. In FIG. 5C, a treatment map indicating all lesion locations (in black) after scaling from pixel coordinates to physical treatment plane coordinates is shown. In FIG. 5D, a map of recommended values for laser fluence settings determined by the algorithm from optical density (e.g., grayscale or color values) of lesion pixels is shown.

FIG. 5A shows a first image 500 which may include a Y-coordinate axis 502, an X-coordinate axis 504, a first lesion 506, a second lesion 508, a third lesion 510, a fourth lesion 512, and/or an Nth lesion 514. In one example, the first lesion 506 includes two main areas with two parts in each. The first area of first lesion 506 is located on the upper left of the lesion body, and has a darker point area with a lighter heart shaped area. The second area of first lesion 506 is located to the lower right of the first area and includes a dark lens shaped area with a lighter rim area. In another example, the second lesion 508 has a heavy dark area surrounded by moderate dark areas. The third lesion 510 has a few dark spots surrounded by lighter areas. Fourth lesion 512 is a small, light area. In another example, the Nth lesion 514 has a dark center surrounded by light areas. All five lesions have different shading and/or colors, different sizes, and different shapes. The second lesion 508 is the darkest lesion, followed by the first lesion 506, the third lesion 510, the fourth lesion 512, and then the Nth lesion 514. The third lesion 510 is the largest lesion, followed by the first lesion 506, the second lesion 508, the Nth lesion 514, and then the fourth lesion 512.

FIG. 5B shows a second image 530 which may include a first lesion boundary 538, a second lesion boundary 534, a third lesion boundary 536, a fourth lesion boundary 542, and/or an Nth lesion boundary 540. In one example, the first lesion boundary 538 has an irregular shape, the second lesion boundary 534 has an approximate circle shape, the third lesion boundary 536 has an approximate oval shape, the fourth lesion boundary 542 has a circular shape, and the Nth lesion boundary 540 has a circular shape. In a preferred embodiment, the image processing algorithm may determine image boundaries that are arbitrary in shape and based on the grayscale or color pixel values of each lesion identified within the image.

FIG. 5C shows a third image 550 (e.g., a treatment map) which identifies target skin areas to be treated within the imaged skin area, with the remainder of the image comprising non-target area to be left untreated. The mapped target skin areas may include a first treatment area 566, a second treatment area 558, a third treatment area 560, a fourth treatment area 564, and/or an Nth treatment area 562. In this example, after scaling from the pixel coordinates (FIG. 5B) to physical treatment plane coordinates in FIG. 5C, a treatment map is created to distinguish areas to be treated from areas to be left untreated (i.e., target and non-target areas).

FIG. 5D shows the fourth image 580 comprising a graded treatment map that not only illustrates target and non-target areas, but provides an indication of differences in the laser fluence that should be used to treat each target area or sub-area. In the embodiment shown, the scale of grayscale values 594 at the bottom of the figure provides a fluence scale for correlating laser fluence values suitable for treating corresponding grayscale values in each target skin area and/or sub-areas. While FIG. 5D specifically discloses laser fluences (indicated by the grayscale shading) to be used for each target area, it will be appreciated in view of the present disclosure that FIG. 5D may also incorporate other parameters such as laser pulse duration, as discussed more fully in connection with FIG. 7

FIG. 5D illustrates a treatment map that includes a first set of treatment parameters based on the density of the shading in each target skin areas. Appropriate laser fluence parameters may be determined from the scale of grayscale values 594 at the bottom of the Figure. The figure illustrates that two different treatment fluences 592, 593 may be used to treat first lesion 506, a second set of treatment fluences 584 may be used to treat second lesion 508, a third set of treatment parameters 586 may be used to treat third lesion 510, a fourth set of treatment parameters 590 may be used to treat fourth lesion 512, and/or an Nth set of treatment parameters 588 may be used to treat Nth lesion 514.

In one example, the algorithm may apply a scale of shading values 594 to each lesion area or sub-area to determine fluence values or other treatment parameters. In the example of FIG. 5D, the algorithm may use scale 594 for the first lesion 506 to indicate that a first portion 593 of the first lesion 506 should be treated using a range of 8 J/cm² to 11 J/cm², while a second portion 592 of the first lesion 506 should be treated using a range of 16 J/cm² to 18 J/cm². In another example, the algorithm may determine that the second set of treatment parameters 584 for the second lesion 508 should comprise using a fluence in the range of 5 J/cm² to 6 J/cm². In another example, the third set of treatment parameters 586 for the third lesion 510 as determined by the algorithm indicates that the entire third lesion 510 should be treated using a range of 18 J/cm² to 20 J/cm². In another example, the fourth set of treatment parameters 590 for the fourth lesion 512 indicates that the entire fourth lesion should be treated using a range of 12 J/cm² to 14 J/cm². In another example, the Nth set of treatment parameters 588 indicates that the entire Nth lesion 514 should be treated in a range of 13.5 J/cm² to 14.4 J/cm².

In another example, the first set of treatment parameters for the first lesion 506 indicate that a first portion of the first lesion 506 should be treated using a range of 8.2 J/cm² to 11.1 J/cm². Whereas, a second portion of the first lesion 506 should be treated using a range of 15.9 J/cm² to 18.1 J/cm². In another example, the second treatment parameter set for the second lesion 508 indicate that the entire second lesion 508 should be treated using a range of 5.3 J/cm² to 5.7 J/cm². In another example, the third set of treatment parameters 586 for the third lesion 510 indicate that the entire third lesion 510 should be treated using a range of 17.5 J/cm² to 20 J/cm². In another example, the fourth set of treatment parameters for the fourth lesion 512 indicate that the entire fourth lesion should be treated using a range of 12 J/cm² to 14 J/cm². In another example, the fifth set of treatment parameters indicate that this lesion should be treated with a range of 14.1 J/cm² to 14.9 J/cm². In another example, the Nth set of treatment parameters indicates that the entire Nth lesion 514 should be treated in a range of 13.8 J/cm² to 14.2 J/cm².

Figure 6A:
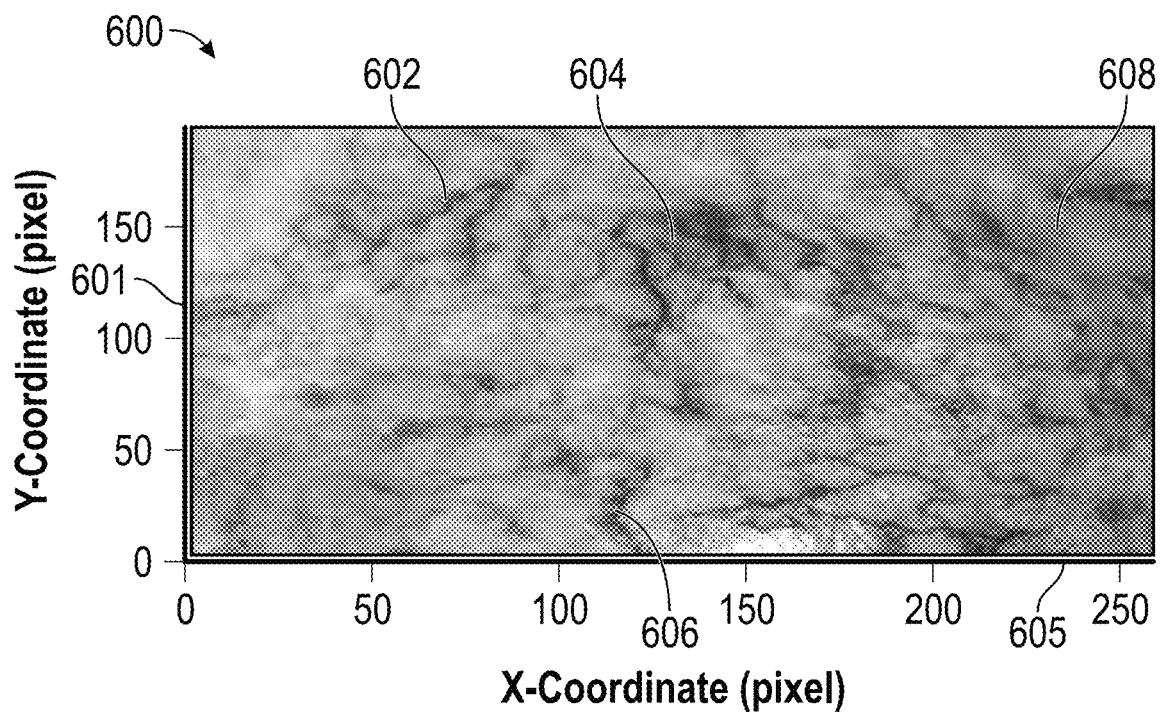
FIGS. 6A-B are illustrations of a treatment mapping procedure for one or more target skin areas within a first skin area, according to one embodiment.
Figure 6B:
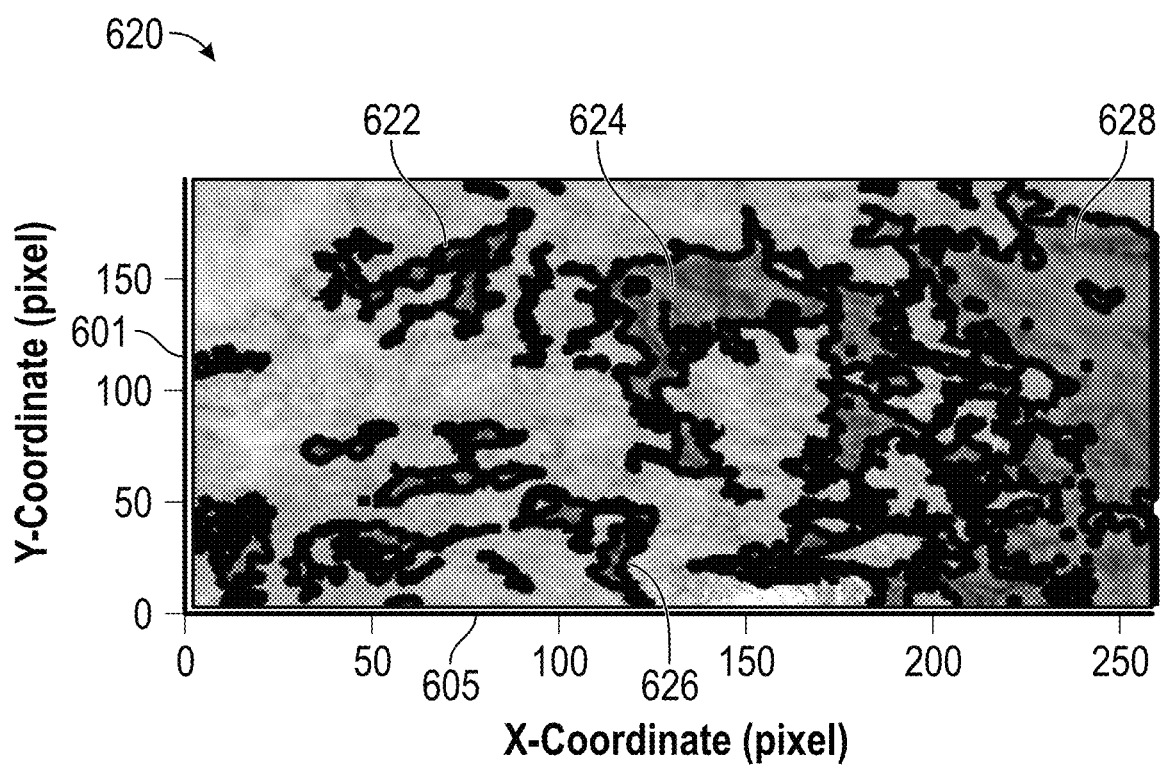

The mapping and treatment processes of the present disclosure may be used for a variety of lesion types. In FIGS. 6A-B, illustrations of a treatment mapping procedure for determining and treating target skin areas is shown, according to one embodiment, for a different type of lesion than those shown in FIGS. 5A-D. An example of a diffuse vascular lesion before and after the application of an image segmentation algorithm is shown in FIG. 6A and FIG. 6B, respectively. In FIG. 6A, an image of a selected skin area having multiple target skin areas obtained from an image sensor is shown. In FIG. 6B, a projection of the lesion boundaries onto the image as determined by the image processing algorithm is shown.

FIG. 6A shows a first image 600 of a selected skin area. Image 600 may include a Y-coordinate axis 601, an X-coordinate axis 605, a first lesion 602, a second lesion 604, a third lesion 606, and/or an Nth lesion 608. In one example, the first lesion 602 has a wishbone shape with two primary vein branches. In another example, the second lesion 604 has four to five primary vein branches. In another example, the third lesion 606 has one primary vein branch. In another example, the Nth lesion 608 has one primary vein branch. All four lesions have different colors, different sizes and different shapes or configurations. The second lesion 604 is the darkest lesion, followed by the third lesion 606, the first lesion 602, and then the Nth lesion 608. The second lesion 604 is the largest followed by the first lesion 602, the Nth lesion 608, and then the third lesion 606.

FIG. 6B shows a second image 620 which may include a first lesion boundary 622, a second lesion boundary 624, a third lesion boundary 626, and/or an Nth lesion boundary 628, with the remaining areas comprising non-target areas to receive no laser treatment. As shown in FIG. 6B, each of these lesion boundaries has an irregular shape.

Figure 7:
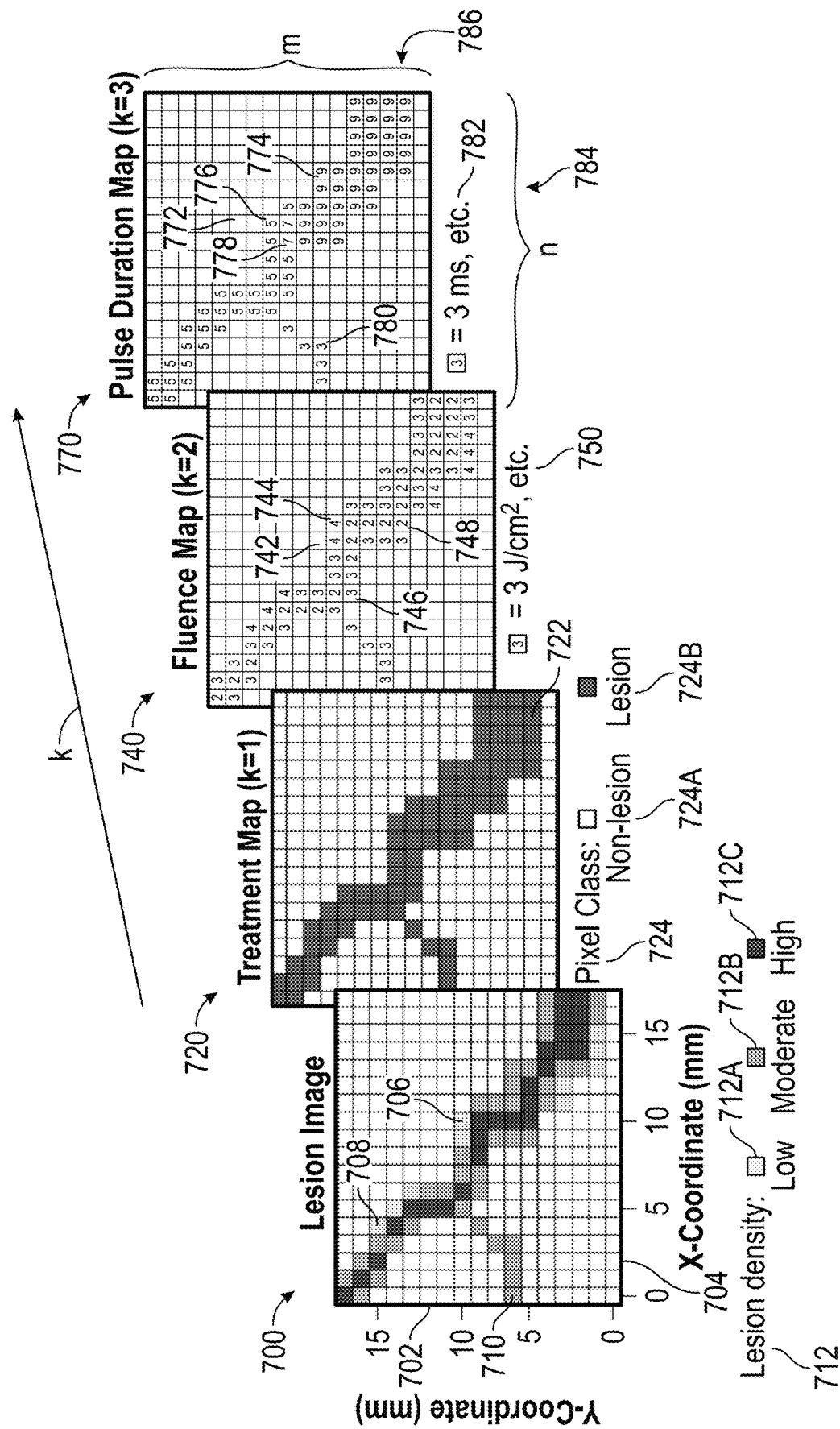
FIG. 7 illustrates a treatment mapping procedure and treatment parameters mapping for one or more target skin areas or sub-areas to be treated, according to one embodiment.

In one example, for vascular lesions, the image data may also be used to determine the optimum setting for laser pulse duration. In a particular embodiment, when treating vascular lesions, the laser pulse duration is set roughly equal to the thermal relaxation time of the vascular vessel to maximize treatment efficacy. The thermal relaxation time, in turn, is determined by the diameter of the vessel. Therefore, the image processing algorithm may perform an image analysis to identify the vessel diameter(s) associated with the location of a particular vascular lesion (e.g., using the pixels defining the lesion) to determine the optimum laser pulse duration to be calculated for treatment of each area or sub-area associated with the vascular lesion. In particular, a pixel-by-pixel analysis algorithm may be used to create a detailed map of a vascular lesion in which each pixel is treated individually as a sub-area of a larger target skin area comprising the entire lesion. The algorithm may also calculate or otherwise determine additional laser treatment parameters, which may include a laser wavelength, a delay time between laser pulses, a number of pulses fired at a particular location or pixel ("pulse stacking"), and/or a spatial overlap or separation distance between sequential pulses. Consequently, the algorithm may produce a treatment map in the form of a 3-dimensional, n×m×k array, where n, m, and k are the number of elements in each dimension of a treatment array for improved precision in targeting lesion tissue while not treating non-lesion (i.e., non-target) skin areas. Two of the dimensions provide the spatial coordinates of each pixel in the treatment plane and the third dimension provides one or more values for treatment parameters as shown in FIG. 7. In other embodiments, additional dimensions (e.g., a four-dimensional, five-dimensional, or Nth-dimensional array) may be used to provide even more precision in treating each lesion area or sub-area.

In FIG. 7, illustrations of a treatment mapping procedure and treatment parameters maps for one or more treatment (e.g., target) areas within a selected or imaged skin area are shown, according to one embodiment. In particular, an example of a 25×25 pixel image of a vascular lesion with a primary blood vessel branching into two smaller vessels is shown. In a first image 700 ("Lesion Image"), a raw image data with pixel coordinates converted to physical coordinates in the treatment plane is shown. In a second image 720 ("Treatment Map"), a treatment map indicating which pixels/areas should be treated and which should not be treated (i.e., target and non-target areas) is shown. In a third image 740 ("Fluence Map") and a fourth image 770 ("Pulse Duration Map"), determined and/or recommended settings for laser fluence and pulse duration, respectively, for each sub-area of the target lesion are shown, based on lesion density observed in first image 700, with different numbers in the map indicating higher or lower laser fluences or pulse duration for each target sub-area/pixel.

First image 700 includes a Y-coordinate axis 702, an X-coordinate axis 704, a primary lesion trunk 706, a first lesion branch 708, and/or a second lesion branch 710. A first legend 712 for the first image 700 may be used to identify low density lesion areas 712A, moderate density lesion areas 712B, and/or a high density lesion areas 712C. In alternative embodiments, a more graduated scale such as that provided in FIG. 5D may be used to indicate a greater range of lesion densities corresponding to a greater range of treatment parameters to be provided. In one example, the primary lesion trunk 706 and part of first lesion branch 708 are primarily high density with some moderate density areas, while the second lesion branch 710 is primarily moderate density with some low density areas.

FIG. 7 includes the second image 720 with a treatment map 722 for the lesion 706, 708, 710 to distinguish target/treatment areas or sub-areas from non-target areas. A second legend 724 for the second image 720 may be used to distinguish non-lesion image areas 724A from lesion image areas 724B in the treatment map 722. Treatment map 722 covers the entire lesions (706, 708, and 710) as well as non-treatment areas corresponding to the unshaded or non-lesion pixels. In various other examples, the treatment map 722 may cover any portion (e.g., 99.9%, . . . , 99.0%, 90.0%, . . . , 70.0%, . . . , 50.0%, . . . , 1.1%, . . . , 0.001%) of the lesion 706, 708, and 710.

FIG. 7 also includes the third image 740 which may include a fluence map 742 of the lesion 706, 708, 710. The fluence map 742 may include a first fluence number 744 (e.g., 4), a second fluence number 746 (e.g., 3), and/or an Nth fluence number 748 (e.g., 2), which may differ depending upon the fluence needed to treat treatment area(s) (e.g., one or more pixels) corresponding to the fluence value. In addition, a third legend 750 for third image 740 may show that the second fluence number 746 equals 3 J/cm$^2$. It will be appreciated that different legends may be used depending upon the type of lesion being treated, the power and/or beam diameter of the laser pulses, and other system-specific and patient-specific parameters. As previously discussed in connection with FIG. 5D, the laser fluence number may be determined based on one or more lesion characteristics (e.g., shade, color, target chromophore, etc.).

FIG. 7 further includes the fourth image 770 which may include a pulse duration map 772 for the lesion 706, 708, 710. The pulse duration map 772 may include a first pulse duration 774 (e.g., 9), a second pulse duration 776 (e.g., 5), a third pulse duration 778 (e.g., 7), and/or an Nth pulse duration 780 (e.g., 3). In addition, the fourth image 770 may have an n-coordinate 784 and an m-coordinate 786 corresponding to the location (e.g., pixel or spatial coordinates) of discrete sub-areas of the lesion 706, 708, 710. Further, a fourth legend 782 may show that the Nth pulse duration 780 is equal to 3 milliseconds (ms). In one embodiment, the laser pulse duration may be set roughly equal to the thermal relaxation time of the vascular vessel in a particular area or region of the lesion 706, 708, 710 to maximize treatment efficacy. The thermal relaxation time in turn is determined by the diameter of the vessel. In one example, the first pulse duration 774 is based on the diameter of the vessel. In this example, the first pulse duration 774 equals 9 and is the largest pulse duration utilized because the diameter of the vessel 706, as shown in the first image 700, is the largest. In another example, the third pulse duration 778 equals 7 because this area has the second largest diameter. In another example, the second pulse duration 776 equals 5 because this area (lesion branch 708) has the third largest diameter. Further, the Nth pulse duration 780 equals 3 because this area (lesion branch 710) has the smallest diameter. It should be noted that the pulse durations may be any number and/or any number disclosed in this disclosure.

For example, darker points or pixels in the first image 700 may require lower fluence (indicated by lower numbers in the fluence map 742) and lighter points may require higher fluence (indicated by higher numbers in the fluence map 742). In the fourth image 770, recommended settings for laser pulse duration based on width of the vein in the vicinity of each pixel location is specified. In this example, maps 722, 742, and 772 form a 3×25×25 array that provides a complete instruction set for x and y spatial coordinates, which pixels are to be treated, laser fluence settings, and pulse duration settings for the treatment areas of interest.

In a particular embodiment, a laser treatment system is provided to use the data from the maps (e.g., 722, 742, and 772) to perform tailored, spatially selective treatment on a desired scale (e.g., pixel-by-pixel basis). Spatial coordinates are sent from the image processor to a driver in the scanner module which positions an optical scanning element (e.g., a movable mirror) to direct the laser pulses to the designated positions on the skin surface. Laser parameter settings such as fluence and pulse duration for each lesion location or sub-location, which in one embodiment correspond to the pixels in the treatment array, are sent to the laser power supply 110 via the control board 112 to configure the laser 106 (FIG. 1) to generate and apply laser pulses having one or more parameters determined by the image processing algorithm to the desired target body areas or sub-areas, while avoiding or minimizing delivery of laser pulses to non-target areas. After the laser pulse is fired at the target areas (e.g., pixels), the process may be repeated for each lesion area/pixel in an automated manner until all lesions in the target skin area(s) have been treated.

Figure 8:
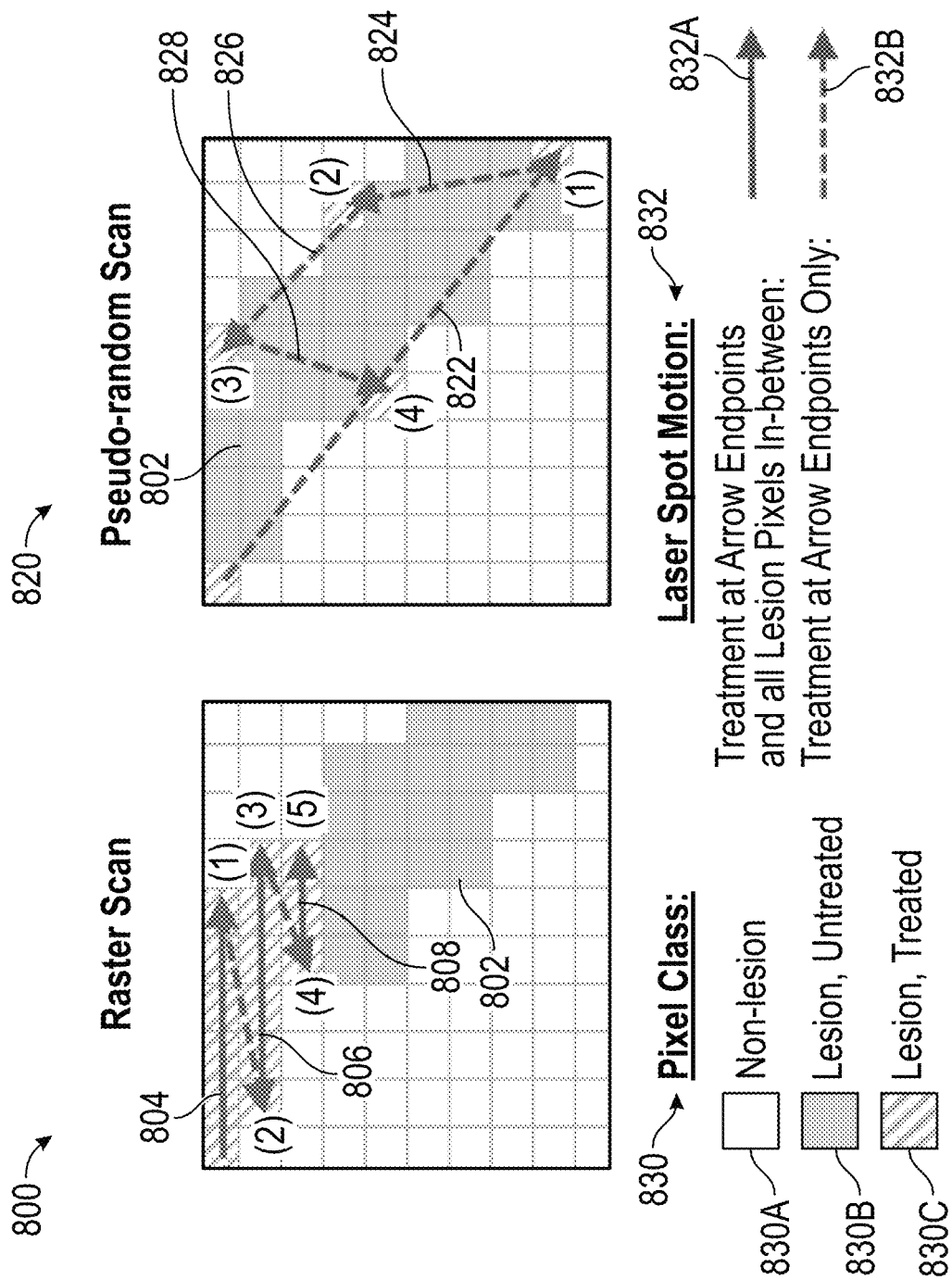
FIG. 8 illustrates a treatment mapping procedure with treatment pattern sequencing for treatment of sub-areas of a target skin area within one or more target skin areas, according to one embodiment.

In FIG. 8, illustrations of a treatment mapping procedure with pattern sequencing for directing laser light (e.g., laser pulses having a desired beam diameter, fluence, pulse width, etc.) to one or more treatment areas are shown, according to one embodiment. A raster scan pattern may be used whereby the scanner (e.g., a mirror movable by an electric motor) initially positions the laser beam at the first pixel location of the first row of the pixel array, scans the beam across the row one pixel at a time (with the laser firing with requested parameter settings at each lesion pixel or pixel group), then moving the beam to the first pixel of the next row and repeating the process until the entire area is treated as illustrated in a first image 800. Alternative scan patterns may also be employed to achieve specific clinical objectives. For example, heat deposited in a small skin area (e.g., a spot associated with one or more pixels) by the laser pulse will dissipate by conduction into adjacent areas, raising the tissue temperature of the treated spot and adjacent area for a period approximately equal to the thermal relaxation time. Therefore, if the time delay before treating a physically adjacent lesion pixel is less than or comparable to the relaxation time, the adjacent pixel will be treated at a slightly higher tissue temperature because of heat conducted from the prior pixel, which may result in overtreatment. To minimize heat leakage effects from adjacent areas, in one embodiment a pseudo-random scan pattern may be employed whereby lesion pixels are treated in a sequence that maximizes the delay to ensure that any heat received by conduction between treatments of adjacent pixels is dissipated before a pulse is applied to the adjacent area, as shown in a second image 820.

First image 800 which may include a lesion 802 and a first treatment pattern. The first treatment pattern may include a first path 804, a second path 806, and/or an Nth path 808. In this example, the first treatment pattern sequentially treats each and every lesion pixel on the first path 804, the second path 806, and/or the Nth path 808, in order. A first legend 830 for the first image 800 and second image 820 may include non-lesion image pixels 830A, untreated lesion image pixels 830B, and/or treated lesion image pixels 830C. A second legend 832 for the first image and second images 800, 820 may include first treatment image paths 832A and second treatment image paths 832B. In first treatment image paths 832A, treatment occurs at arrow endpoints and at all lesion pixels in-between these endpoints that are in the image path. In second treatment image paths 832B, treatment occurs only at the arrow endpoint pixels.

The second image 820 may include the lesion 802 and a second treatment pattern different from that of the first image 800. The second treatment pattern may include a first path 822, a second path 824, a third path 826, and/or an Nth path 828. In this example, the second treatment pattern only treats the lesion pixels at end points of the first path 822, the second path 824, the third path 826, and/or the Nth path 828. This treatment pattern allows heat from a treated pixel to fully dissipate before laser pulse(s) are applied to an adjacent pixel, minimizing overtreatment risk, but involves greater movement of the scanner.

FIG. 8 shows examples of scan patterns for treatment of a lesion. In first image 800, treatment of a lesion using a raster scan pattern whereby consecutive lesion pixels and rows are treated sequentially is shown. Movement of the laser beam follows the sequence from (1) to (5) where solid arrows indicate treatment at all intersected lesion pixels within the solid arrow path, and dashed arrows indicate treatment at arrow endpoints only, omitting treatment of pixels other than the arrow or path endpoints. In image 820, a treatment of the same lesion as in image 800 is shown using a pseudo-random scan pattern to limit buildup of heat in the tissue. For brevity, treatment of the first 5 lesion pixels only is shown. For both images 800 and 820, the scan pattern may continue until all lesion pixels are treated.

In one example, the volume heated by a laser pulse may be approximated as a planar element with thickness equal to the thickness of the absorbing tissue layer. The thermal relaxation time τ may then be estimated by dimensional analysis to be:

$$\tau = \frac{d^2}{8\kappa} \qquad \text{Eqn. 1}$$

where d is the thickness of the absorbing layer and κ is the thermal diffusivity of the tissue (κ≅0.1 mm²/s). For pigmented lesions, the absorbing layer may be approximated to be about 0.05 mm thick (due to variation of melanin concentration in the epidermis with depth) for which τ=3 ms. Thus, heat will dissipate exponentially from a treated spot with a time constant of about 3 ms. Consequently, when treating pigmented lesions with a pseudo random scan pattern to minimize temperature buildup, the time between treating adjacent pixels should be >3 ms and preferably >10 ms to maximize dissipation of heat. In various examples, the delay time utilized may be 3 ms, . . . , 3.1 ms, 3.5 ms, . . . , 4.0 ms, 4.5 ms, 15 ms, and/or 100 ms.

Figure 9B:
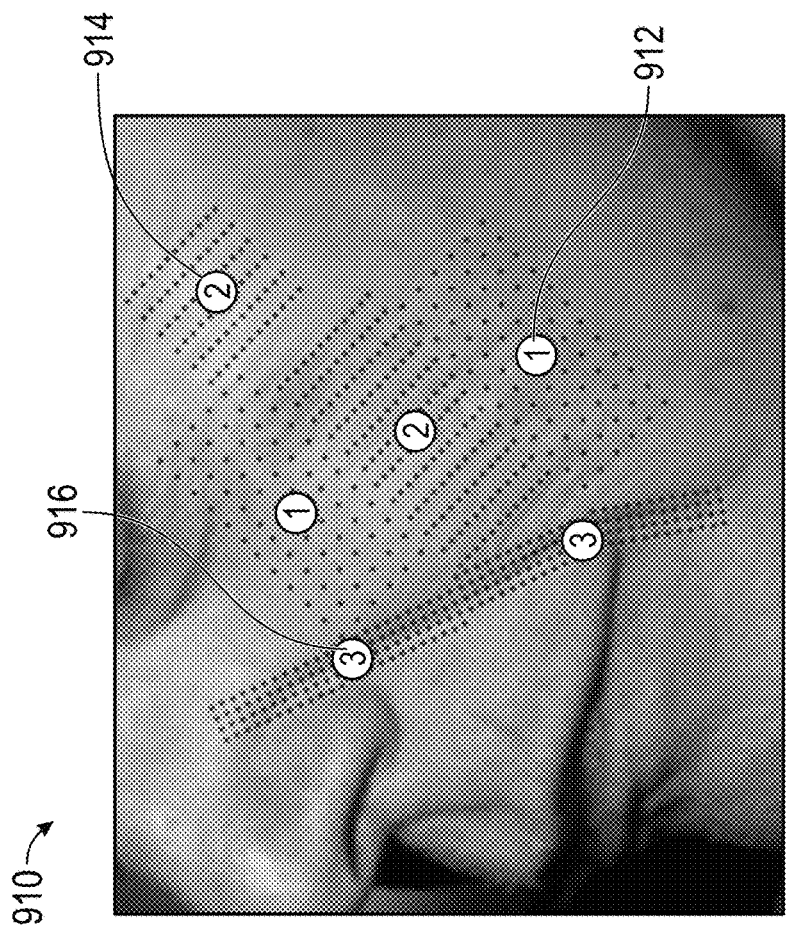
FIGS. 9A-B are illustrations of a treatment mapping procedure for a wrinkle treatment procedure, according to one embodiment.

In some cases, it may be preferred to use a scan pattern that delivers a fractional treatment, whereby some lesion pixels are left untreated. Stated differently, in fractional treatments, not only are non-target areas left untreated, but only a predetermined percentage of the total area of target skin areas are treated. For example, in a lesion such as lesion 802 of FIG. 8, in a fractional treatment laser pulses are applied to only a fraction or desired percentage (e.g., 10%, 20%, 30%, 40%, 50%, etc.) of the total target skin area comprising the lesion. In one example, a treatment procedure may apply laser pulses to a desired fraction (10 to 30%) of the skin surface of a lesion area with small treatment spots (diameter equal to 0.5 mm or less). Fractional treatments have the benefit of leaving each treatment location partially or completely surrounded by healthy tissue, which accelerates the wound healing process, minimizes overtreatment and associated damage and discomfort, and reduces patient downtime. Fractional treatments can also enable a higher laser fluence to be used compared to a non-fractional treatment, which can further improve the treatment efficacy. In the context of the present disclosure, this modality may be extended by leveraging the image data to provide a spatially varying treatment density that is tailored to the darkness of the lesion. For example, lower treatment densities (i.e., lower percentages of the total skin area within a lesion receiving laser pulses) may be used to treat darker areas of the lesion and vice versa. Alternatively, the treatment density may be tailored to the density of the lesions. For example, when treating wrinkles, a higher treatment density may be used to treat areas with higher density or more pronounced wrinkles as shown in FIGS. 9A-B.

Figure 9A:
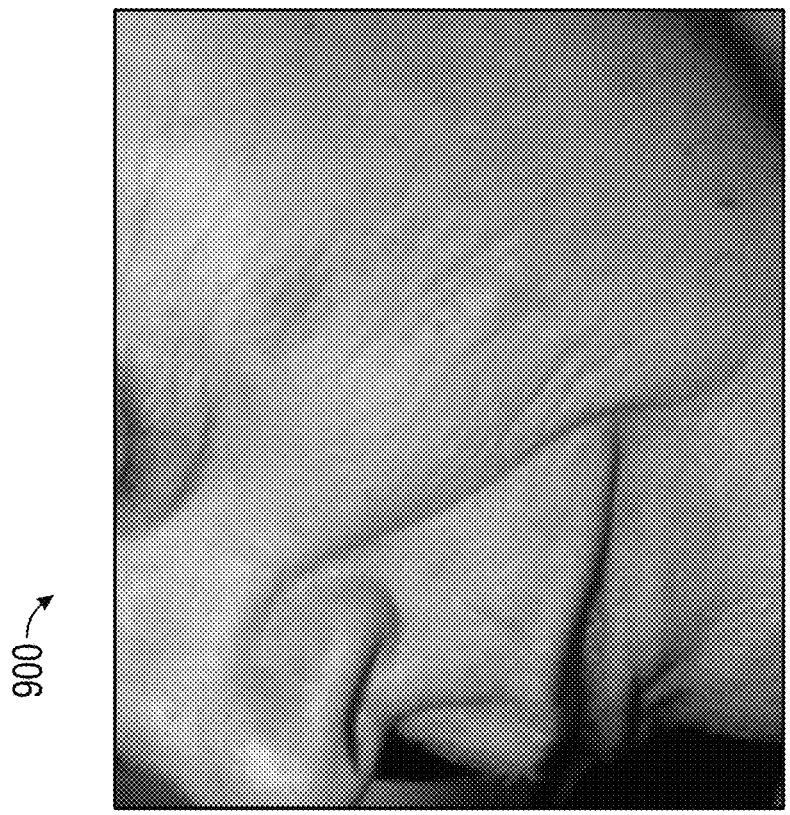

FIG. 9A shows a first image 900 of a patient. FIG. 9B shows a second image 910 of a patient. The second image 910 may include one or more selected skin areas having a first treatment area type 912, a second treatment area type 914, and/or an Nth treatment area type 916. FIG. 9B shows an example of a fractional laser treatment for wrinkles where the density of the treatment (i.e., the percentage of the total area of a lesion that is treated with laser pulses) is adjusted to the density and depth of the wrinkles. In this example, selected skin areas designed by the number 3 (e.g., Nth treatment area type 916) requires a relatively high density of laser treatment spots due to the deep nasolabial fold that runs from the nose to the edge of the lips. In contrast, selected skin areas designated by the number 2 (e.g., second treatment area type 914) and 1 (e.g., first treatment area type 912) require moderate (e.g., second treatment area type 914) and low treatment density (e.g., first treatment area type 912) due to the lesser relative density and depth of wrinkles along the cheek.

Figure 10:
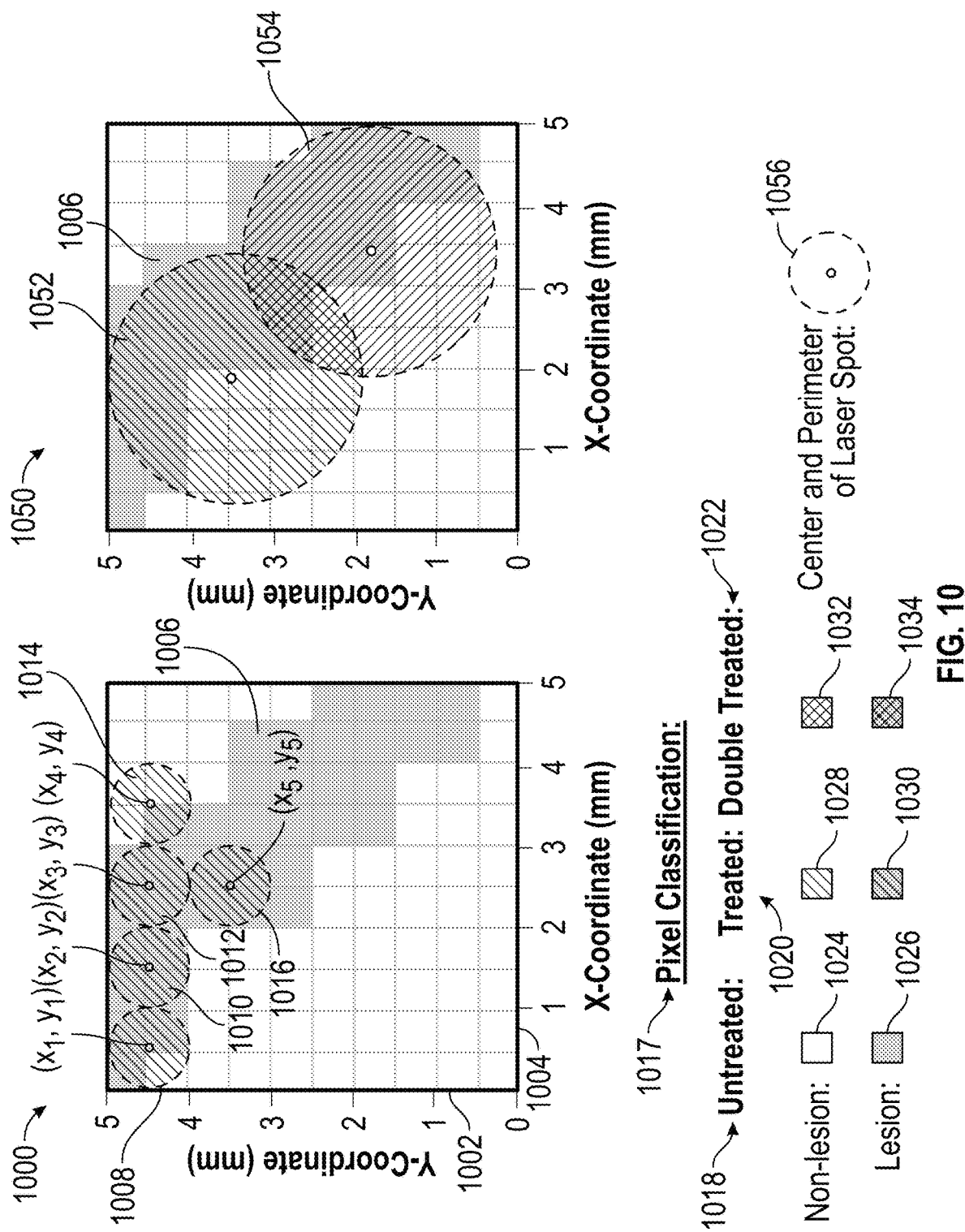
FIG. 10 illustrates a comparison of the precision of a laser skin treatment system using different laser spot sizes, according to one embodiment.

In FIG. 10, illustrations of an embodiment of a method of treatment having a high degree of precision in minimizing overtreatment of target skin areas and treatment of non-target skin areas are shown, according to one embodiment. FIG. 10 shows a first image 1000 of a selected skin area which may include a Y-coordinate axis 1002, an X-coordinate axis 1004, a lesion 1006, a first treatment pulse 1008, a second treatment pulse 1010, a third treatment pulse 1012, a fourth treatment pulse 1014, and/or an Nth treatment pulse 1016. A first legend 1017 utilized for the first image 1000 and a second image 1050 may include an untreated column 1018, a treated column 1020, and/or a double treated column 1022. The first legend 1017 may include untreated non-target (i.e., non-lesion) areas 1024, untreated target (e.g., lesion) areas 1026, a treated non-target areas 1028, treated target areas 1030, double treated non-target areas 1032, and/or a double treated target areas 1034. In addition, a second legend 1056 is utilized with both the first image 1000 and the second image 1050 to show the center and perimeter of individual laser pulses (e.g., beam or spot size). Second image 1050 illustrates the same lesion 1006 as image 1000, and depicts a first treatment pulse 1052, and an Nth treatment pulse 1054. By comparing first and second images 1000, 1050, it can be seen that second image 1050 has significantly more non-target tissue that is inadvertently treated by one or both of laser pulses 1052, 1054. In addition, first image 1000 has no double treated non-target areas and no double treated lesion (e.g., target) areas. In contrast, second image 1050 has a significant amount of double treated non-target (e.g., non-lesion) areas and double treated target (e.g., lesion) areas.

In one example, the laser spot size may cover more than one pixel on the treatment surface. In this case, an average of the optimum laser parameters for the pixels covered by a single laser pulse/spot may be used for treatment, and treatment proceeds on a shot-to-shot basis on a spatial scale defined by the spot size. This is illustrated in first image 1000, which shows the first 5 pulses 1008, 1010, 1012, 1014, and 1016 for an image-guided treatment procedure for the same lesion 1006 shown in FIG. 8 using a raster scan with no spatial overlap between spots that is programmed to treat at least a portion of all lesion pixels. In this case, each laser pulse treats approximately a 2×2 pixel square of lesion tissue and the treatment map (k=1) consists of the set of x and y-coordinates of all laser spot centers required to treat the lesion tissue 1006 in the treatment plane and satisfy one or more treatment goals such as minimizing treatment or double treatment of non-target tissue areas, maximizing treatment of target tissue areas, and minimizing overtreatment (e.g., double treatment, triple treatment, etc.) of target tissue areas. The treatment map may be specified as shown in Eqn. 2, where p equals the total number of spots:

$$\text{Treatment Map} = \{(x_1, y_1), (x_2, y_2), (x_3, y_3), \ldots (x_p, y_p)\} \qquad \text{Eqn. 2}$$

In one example, a treatment preferably exposes only target (e.g., lesion) tissue areas to laser irradiation in order to minimize patient discomfort and recovery time, but for the procedure illustrated in first image 1000, the finite laser spot size results in the first and fourth spots treating portions of 3 and 1 non-target tissue pixel areas, respectively. Accordingly, although embodiments of the present disclosure may be used to minimize treatment of non-target areas and maximize treatment of target skin areas, it will be appreciated that it may not always be practical or possible to treat precisely only target skin areas and completely avoid treatment of non-target areas. However, the present disclosure facilitates much more precise targeting of many lesion types so as to minimize treatment of non-target skin areas, maximize treatment of target skin areas, and avoid overtreatment of either target or non-target skin areas, using the systems and methods disclosed.

In FIG. 10, an example of a treatment for a lesion where the laser spot size covers multiple pixels in the treatment plane is shown. In first image 1000, the first 5 pulses are shown for a treatment procedure using a raster scan with a treatment algorithm to achieve no spatial overlap between the areas (e.g., pixels) treated by each laser pulse, and treatment of at least a portion of all lesion pixels. Stated differently, the treatment algorithm is implemented to achieve the treatment goals of maximizing the treatment of the target (e.g., lesion) skin area while minimizing double treatment of the target (e.g., lesion) skin area and maximizing the treatment of the target skin area. It will be appreciated that other or additional treatment goals (e.g., ensuring that the area of non-target skin areas are no more than a desired percentage (e.g., less than 50, 40, 30, 25, 20, 10, 5, or 1 percent) of the area of a particular target skin area being treated, where the areas of target and non-target skin areas are determined based on a mapping algorithm and one or more laser beam/spot sizes used to treat the target skin area/lesion) may be implemented.

In second image 1050, a treatment typical of prior art systems utilizing a relatively large spot size and manual application of the laser pulses to the lesion area by a system user is shown. Second image 1050 illustrates a large spot size laser beam being manually aligned to the lesion by user moving the hand piece without the aid of an image-guided scanning system as disclosed herein. The weight of the hand piece combined with limits in operator hand-to-eye coordination and visual acuity make it challenging to consistently and precisely align laser spots in a precise dimensional array as shown in first image 1000, where treatment of non-lesion tissue, overtreatment of lesion tissue due to overlapping spots, and under treatment of lesion tissue due to spaces between spots are all minimized. The foregoing human operator limitations are magnified in the case of treating a large lesion or many lesions manually with a small spot, since many (possibly hundreds) of spots would need to be precisely aligned to cover the large surface area. In such cases, achieving one or more goals such as minimizing treatment of non-target skin areas, maximizing treatment of target skin areas, and avoiding or minimizing overtreatment of either target or non-target areas can become essentially impossible.

For these reasons, a larger spot is typically used in current systems and treatment methods. As shown in second image 1050, this results in relatively high levels of over and under treated areas of lesion tissue, and undesired treatment of non-target tissue. Additionally, the ability to tailor treatment parameters to spatial variations in lesion properties is limited since the spatial resolution of the treatment provided is inherently limited by the larger spot size. Such current systems also require treatment parameters to be changed manually using system controls such as a touchscreen mounted to the console. This can be time consuming for the operator and consequently reduces the frequency at which treatment parameters are optimized to spatial variations in lesion properties, in contrast to the present disclosure which may determine and set treatment parameters for much smaller areas automatically, and provide automated treatment of the systems and speeds and accuracy or precision impossible to achieve by human operators. The cumulative effect of these factors results in both over-treatment and undertreatment of target and non-target areas for each patient, resulting in both longer recovery times and lower efficacy relative to systems and methods of this disclosure.

From the discussion above, it is clear that minimizing the spot size is an important factor for optimizing clinical outcomes. However, reducing the spot size has the undesirable consequence of reducing the penetration depth (and therefore treatment depth) of the incident laser light into the tissue. Because of the limited penetration for small spots at typical fluences, the minimum spot size typically offered by commercial systems today is 2 mm or 3 mm. In fact, the spot size is typically adjusted to be equal to or slightly larger than the lesion size to maximize treatment depth and minimize treatment time. For example, a 4 mm wide pigmented lesion is commonly treated with a 4 mm or 5 mm diameter spot. Although this results in both significant overtreatment and undertreatment of nearly all lesions, it is accepted as a tradeoff for treatments that achieve a desired depth of penetration and which can be performed by an operator in a reasonable time period.

Figure 11:
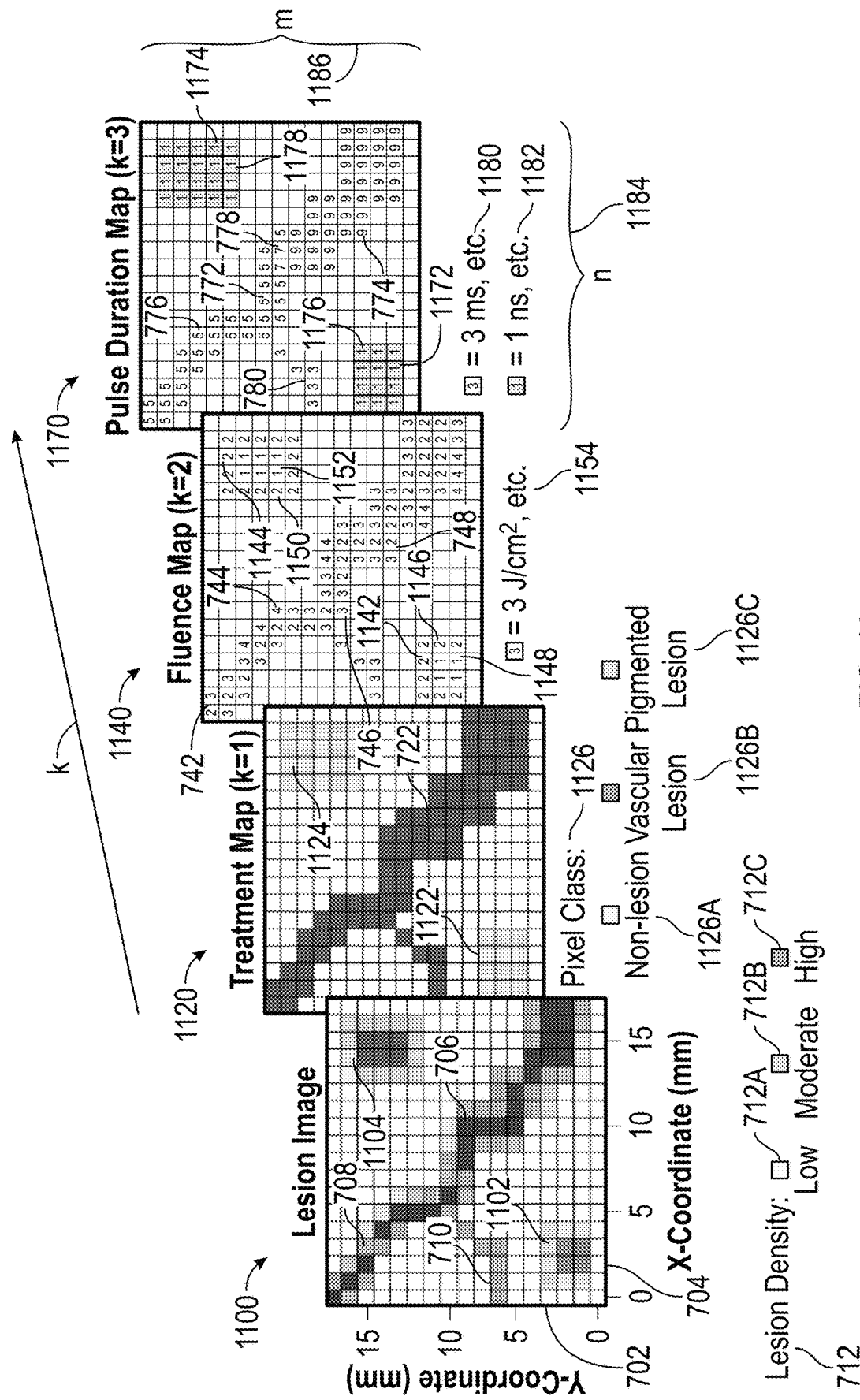
FIG. 11 illustrates a treatment mapping procedure and treatment parameters mapping for one or more target skin areas or sub-areas to be treated, according to one embodiment.

FIG. 11 shows a first image 1100 ("Lesion Image") which may include lesion 706, 708, 710 from FIG. 7, a first pigmented lesion 1102, and a second pigmented lesion 1104. The first legend 712 for the first image 1100 may include shading to identify low density areas/pixels 712A, moderate density areas/pixels 712B, and/or high density areas/pixels 712C. In one example, the lesion areas 706 and 708 are primarily high density with some moderate density areas/pixels, while second lesion branch 710 is primarily moderate density with some low density areas/pixels. In another example, the first pigmented lesion 1102 has a center area with moderate density which is enveloped by areas with low density. Finally, the second pigmented lesion 1104 has a center area of moderate density surrounded by areas with low density.

FIG. 11 further shows a second image 1120 ("Treatment Map") with the treatment map 722 for the lesion 706, 708, 710, a first treatment map 1122 for first pigmented lesion 1102, and a second treatment map 1124 for the second pigmented lesion 1104. Treatment maps 722, 1122, and 1124 distinguish treatment from non-treatment areas and provide shading to distinguish between different lesion types. A second legend 1126 for the second image 1120 may include a first shading to identify non-lesion pixels 1126A, a second shading to identify vascular lesion pixels 1126B, and a third shading to identify pigmented lesion pixels 1126C. It will be appreciated that other shadings may be provided to identify different lesion types (e.g., wrinkles). As shown in second image 1120, the treatment map 722 covers the entire vascular lesion 706, 708, 710. In various other examples, the treatment map 722 may cover any portion (e.g., 99.9%, . . . , 99.0%, . . . , 90.0%, . . . , 70.0%, . . . , 50.0%, . . . , 1.1%, . . . , 0.001%) of the vascular lesion 706, with the areas of the lesion not identified in the treatment map 722 as lesion tissue identifying lesion areas that are not to be treated (e.g., treatment map 722 may provide a treatment map for fractional treatment of the lesion 706, 708, 710). First treatment map 1122 as depicted covers the entire first pigmented lesion 1102, although it will be appreciated that in various other examples, the first treatment map 1122 may cover any portion (e.g., 99.5%, . . . , 93.3%, . . . , 79.9%, . . . , 60.0%, . . . , 45.0%, . . . , 1.1%, . . . , 0.001%) of the first pigmented lesion 1102, to provide a fractional treatment map as noted above in connection with vascular lesion 706, 708, 710. In addition, the second treatment map 1124 as shown covers the entire second pigmented lesion 1104, while in various other examples, the second treatment map 1124 may cover any portion (e.g., 99.9%, . . . , 99.3%, . . . , 89.9%, . . . , 88.0%, . . . , 87.0%, . . . , 1.1%, . . . , 0.001%) of the second pigmented lesion 1104.

FIG. 11 also shows a third image 1140 ("Fluence Map") which may include a fluence map 742 for the vascular lesion 706, 708, 710, a first fluence map 1142 for first pigmented lesion 1102, and a second fluence map 1144 for second pigmented lesion 1104. The fluence map 742 may include a first fluence number 744 (e.g., 4), a second fluence number 746 (e.g., 3), and/or an Nth fluence number 748 (e.g., 2) (see fourth image 770, FIG. 7) for treatment of each pixel or sub-area comprising the vascular lesion 706, 708, 710. As shown in fourth image 770 of FIG. 7, the laser fluence number may be determined by one or more lesion characteristics (e.g., grayscale shading, color, size/no. of pixels, etc.). In addition, a third legend 1154 may show that the second fluence number 746 equals 3 $J/cm^2$. Additional or different legends may be used to distinguish between, e.g., types of lesions, pulse power, beam diameter, etc. First fluence map 1142 may include a first fluence number 1146 (e.g., 2) and a second fluence number 1148 (e.g., 1) for treatment of first pigmented lesion 1102. Second fluence map 1144 may include a third fluence number 1150 (e.g., 2) and a fourth fluence number 1152 (e.g., 1) for treatment of second pigmented lesion 1104. In this example, the first fluence number 1146 for the first pigmented lesion 1102 and the third fluence number 1150 for the second pigmented lesion 1104 are the same number, but these numbers could be different depending upon the image processing results for each lesion. In this example, the second fluence number 1148 for the first pigmented lesion 1102 and the fourth fluence number 1152 for the second pigmented lesion 1104 are the same number, but these numbers could also be different.

FIG. 11 includes a fourth image 1170 ("Pulse Duration Map") which may include the pulse duration map 772 for the lesion 706, 708, 710. The pulse duration map 772 may include a first pulse duration 774 (e.g., 9), a second pulse duration 776 (e.g., 5), a third pulse duration 778 (e.g., 7), and/or the Nth pulse duration 780 (e.g., 3). In addition, the fourth image 1170 may have an n-coordinate 1184 and an m-coordinate 1186 corresponding to the location (e.g., pixel or spatial coordinates) of discrete sub-areas of the lesion 706, 708, 710. A fourth legend 1180 may show that the Nth pulse duration 780 is equal to 3 ms (see fourth image 770, FIG. 7). The fourth image 1170 may include a first pulse duration map 1172 for the first pigmented lesion 1102 and a second pulse duration map 1174 for the second pigmented lesion 1104. First pulse duration map 1172 for first pigmented lesion 1102 may include a first pulse duration 1176 (e.g., 1 nanosecond), and second pulse duration map 1174 for second pigmented lesion 1104 may have a second pulse duration 1178 (e.g., 1 nanosecond). A fifth legend 1182 shows that both the first pulse duration 1176 and the second pulse duration 1178 have a value of 1 nanosecond (ns). However, these duration numbers can be different and can range from 1 ns to 100 ns. It will be appreciated more generally that pulse duration map 772 may include one or more map sub-areas each corresponding to a lesion to be treated with one or more laser pulses, that the maps may include one or more pulse duration parameters each corresponding to one or more pixels/sub-areas of the lesion to be treated, and that in some embodiments legends may be provided to indicate one or more of the pulse durations used in the pulse duration map for each lesion. Finally, the maps of each lesion may comprise a fractional map in which some lesion areas are left untreated (i.e., the lesion fluence map may include areas in which a fluence of zero is provided).

In one embodiment, the laser pulse duration may be set roughly equal to or less than the thermal relaxation time of the vascular vessel to maximize treatment efficacy. For vascular lesions, the thermal relaxation time in turn is determined by the diameter of the vessel. In one example, the first pulse duration 774 is based on the diameter of the vessel. In this example, the first pulse duration 774 equals 9 and is the largest pulse duration utilized because the diameter of the vessel region 706 as shown in FIG. 7 is the largest. In another example, the third pulse duration 778 equals 7 because this area of legion 706 has the second largest diameter. In another example, the second pulse duration 776 equals 5 because this area has the third largest diameter. Further, the Nth pulse duration 780 equals 3 because this area has the smallest diameter. It should be noted that the pulse durations may be any number and/or any number disclosed in this disclosure, and depending upon the lesion under treatment, may comprise pulse durations ranging from as small as 1 picosecond (ps) to 100 milliseconds (ms) or more.

Figure 12:
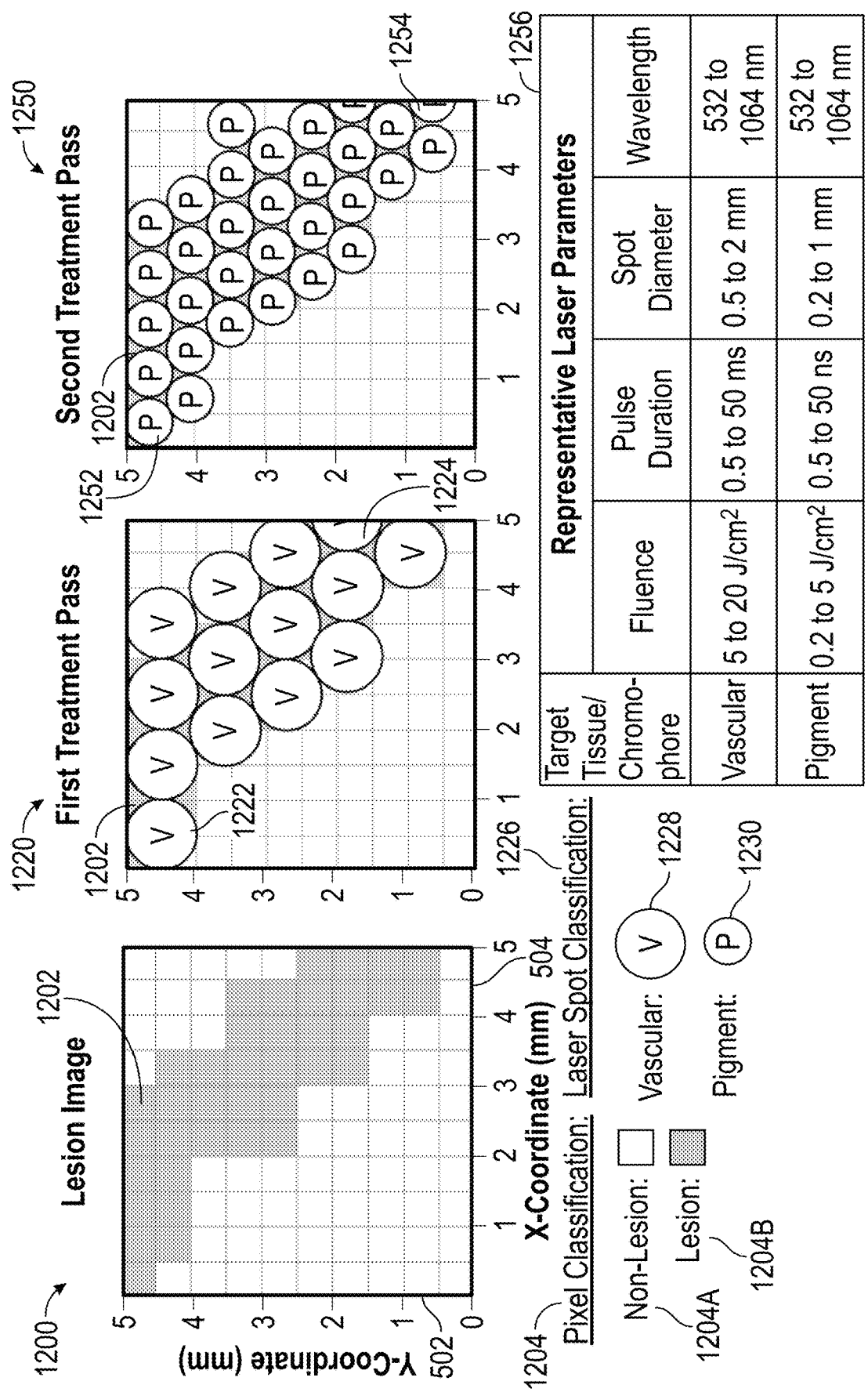
FIG. 12 illustrates a multi-factorial confluent treatment procedure, according to one embodiment.

In FIG. 12, a first skin image 1200 ("Lesion Image") of a selected first skin area is shown in pixelized form, according to one embodiment. The first skin area image 1200 includes a lesion 1202. A first legend 1204 may include shading to identify a non-lesion areas/pixels 1204A and lesion areas/pixels 1204B. FIG. 12 also includes a first treatment pass map 1220 ("First Treatment Pass") which identifies areas of lesion 1202 treated by laser pulses, e.g., a first vascular treatment laser pulse 1222, and an Nth vascular treatment laser pulse 1224, wherein the laser pulses are overlaid on the image of the lesion area/pixels 1204B. A second legend 1226 may indicate laser pulses 1228 used for treatment of vascular lesions and a laser pulses 1230 used to treat pigmented lesions. FIG. 12 further shows a second treatment pass map 1250 ("Second Treatment Pass") which identifies areas of the lesion 1202 treated by laser pulses, e.g., a first pigmented lesion treatment laser pulse 1252, and an Nth pigmented lesion treatment laser pulse 1254. A third legend 1256 shows various treatment parameters for both the vascular lesion treatment laser pulses and the pigmented lesion treatment pulses.

In one example, the first vascular treatment pulse 1222 and every vascular treatment pulse up until the Nth vascular treatment pulse 1224 in the first treatment pass map 1220 occurs during a first treatment period before the treatment shown in second treatment pass map 1250 begins. In this example, the first pigmented lesion treatment pulse 1252 and every pigmented lesion treatment pulse up until the Nth pigmented lesion treatment pulse 1254 occurs during a second treatment period. In one example, the vascular lesion treatment pulses (e.g., 1222, . . . , 1224) have a fluence of between 5 J/cm² to 20 J/cm²; a pulse duration from 0.5 to 50 ms; a spot diameter of between 0.5 to 2 mm; and/or a wavelength of between 532 to 1064 nanometers (nm). In another example, the pigmented lesion treatment pulses have a fluence of between 0.2 J/cm² to 5 J/cm²; a pulse duration of between 0.5 to 50 nanoseconds (ns); a spot diameter of between 0.2 to 1 mm; and/or a wavelength of between 532 to 1064 nm.

In should be noted that any of the foregoing pulse parameters may be changed and/or modified when moving from one treatment spot or pixel area within a target skin area to another. For example, the first vascular treatment pulse 1222 may have a fluence of 5 J/cm²; a pulse duration of 0.5 ms; a spot diameter of 1 mm; and a wavelength of 532 nm, while a second vascular treatment pulse may have a fluence of 6 J/cm²; a pulse duration of 0.7 ms; a spot diameter of 1.1 mm; and a wavelength of 600 nm. In a different embodiment, the second vascular treatment pulse may have a fluence of 6 J/cm²; a pulse duration of 0.7 ms; a spot diameter of 1.0 mm; and a wavelength of 532 nm. A third vascular treatment pulse may have a fluence of 10 J/cm²; a pulse duration of 3 ms; a spot diameter of 2 mm; and a wavelength of 1000 nm, and subsequent vascular treatment pulses (e.g., 1224) may have any desired parameter values of fluence, pulse duration, beam/spot diameter, and wavelength. In another example, all of the pulse parameters may remain the same from pulse to pulse. Further, some of the pulse parameters may remain the same from pulse to pulse.

In another example, the first pigmented lesion treatment pulse 1252 may have a fluence of 0.2 J/cm²; a pulse duration of 1.5 ns; a spot diameter of 0.3 mm; and a wavelength of 700 nm, while a second pigmented lesion treatment pulse may have a fluence of 0.4 J/cm²; a pulse duration of 1.1 ns; a spot diameter of 0.3 mm; and a wavelength of 700 nm. In a different embodiment, the second pigmented lesion treatment pulse may have a fluence of 1.1 J/cm²; a pulse duration of 40 ns; a spot diameter of 0.9 mm; and a wavelength of 532 nm. A third pigmented lesion treatment pulse may have a fluence of 3 J/cm²; a pulse duration of 3 ns; a spot diameter of 0.7 mm; and a wavelength of 980 nm. In another example, all of the pulse parameters may remain the same from pulse to pulse. Further, some of the pulse parameters may remain the same from pulse to pulse.

Further, the beam diameter/spot size for the vascular lesion and/or pigmented lesion treatment pulses may be selected to achieve a desired lesion coverage goal for a lesion (e.g., lesion 1202). For example, the beam diameter may be selected to minimize or limit the application of laser pulses to non-target skin areas (e.g., non-lesion areas). In one embodiment, the beam diameter may be automatically selected to achieve a predetermined or user-selectable (e.g., programmable) goal of providing no laser pulses to non-target skin areas determined as part of a target skin area mapping procedure. In one embodiment, the beam diameter may be selected to achieve a goal of limiting the application of laser pulses to non-target skin areas adjacent to a target skin area to 10% of the area of the target skin area. In another embodiment, beam diameter may be selected to achieve a goal of treating a specified fraction (e.g., 0-100%) of a target skin area such as a lesion identified during a mapping procedure as previously discussed. In still another example, beam diameter may be selected to achieve a first goal for the area of non-target skin areas treated with laser pulses and a second goal for the area of target skin areas treated with laser pulses.

Figure 13:
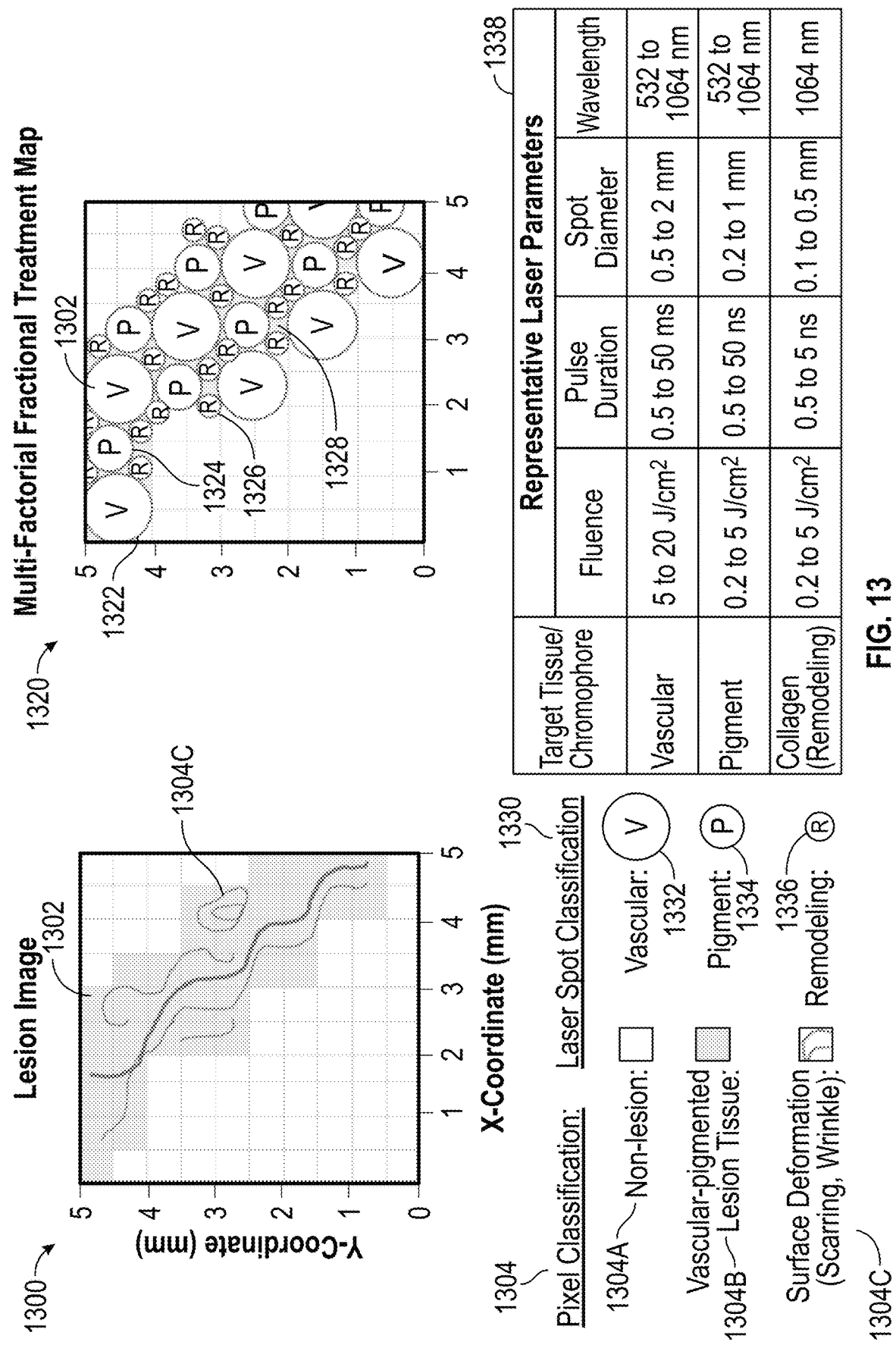
FIG. 13 shows illustrations of a multi-factorial fractional treatment procedure, according to one embodiment.

In FIG. 13, an image of a first skin area 1300 ("Lesion Image") may include a first lesion area 1302. First lesion area 1302 further comprises, a vascular-pigmented lesion area 1304B depicted by shaded pixels, and/or a surface deformation lesion 1304C depicted by curved lines within the vascular-pigmented lesion area 1304B. A first legend 1304 identifies non-lesion sub-areas/pixels 1304A as unshaded areas in the first skin area, depicts vascular-pigmented lesion areas 1304B as shaded pixels, and provides curved lines to show the surface deformation lesion 1304C.

FIG. 13 also shows a multi-factorial fractional treatment map 1320 which may be provided as an overlay of the lesion 1302 of first skin area 1300. The multi-factorial fractional treatment map 1320 includes one or more vascular treatment laser pulses 1322, one or more pigment treatment laser pulses 1324, one or more remodeling treatment laser pulses 1326, and one or more non-treatment areas designated by unshaded not overlaid by treatment pulses 1322, 1324, 1326, as identified in second legend 1330 and as shown on treatment map 1320. A third legend 1338 shows various treatment parameters for the vascular treatment pulses 1322, the pigment treatment pulses 1324, and/or the remodeling treatment pulses 1326. In one example, vascular treatment pulses 1332, pigment treatment pulses 1334, and/or remodeling treatment pulses 1336 may occur in three separate, sequential treatment passes. In other words, all of the vascular treatment pulses are applied to the areas shown on the map 1320, then all of the pigment treatment pulses are applied as shown, and then all of the remodeling treatment pulses are applied. In another example, some (but not all) of the vascular treatment pulses are applied as shown on the map 1320, then some but not all of the pigment treatment pulses are applied, and then some but not all of the remodeling treatment pulses are applied, and the sequence (vascular pulses followed by pigment pulses followed by remodeling pulses) is repeated until all of the treatment areas are treated as the map 1320 specifies. In another example, the treatments may follow one or more patterns for each treatment pass (See FIG. 8) and different patterns may be used depending on which treatment pulses are being applied in a given pass (e.g., vascular, pigment, or remodeling pulses). In another example, one or more of the vascular, pigment, or remodeling pulses may be applied simultaneously in portions of a target skin area to be treated.

In one example, as shown in legend 1338, the vascular treatment pulses have a fluence of between 5 J/cm2 to 20 J/cm2; a pulse duration from 0.5 to 50 ms; a spot diameter of between 0.5 to 2 mm; and/or a wavelength of between 532 to 1064 nm. In another example, the pigment treatment pulses have a fluence of between 0.2 J/cm2 to 5 J/cm2; a pulse duration of between 0.5 to 50 ns; a spot diameter of between 0.2 to 1 mm; and/or a wavelength of between 532 to 1064 nm. In another example, the remodeling treatment pulses (e.g., collagen treatment pulses) have a fluence of between 0.2 J/cm2 to 5 J/cm2; a pulse duration of between 0.5 to 50 ns (or 0.5 to 5 ns); a spot diameter of between 0.1 to 0.5 mm; and/or a wavelength of 1064 nm. In should be noted that any of these parameters may be changed and/or modified when moving from one treatment spot to another for treating target skin areas within a selected/imaged skin area. For example, a first vascular treatment pulse 1222 (FIG. 12) may have a fluence of 5 J/cm2; a pulse duration of 15 ms; a spot diameter of 2 mm; and a wavelength of 750 nm, while a second vascular treatment pulse (e.g., to be applied to an area having a different vessel diameter) may have a fluence of 20 J/cm2; a pulse duration of 0.5 ms; a spot diameter of 0.5 mm; and a wavelength of 1064 nm. Alternatively, the second vascular treatment pulse may have a fluence of 18 J/cm2; a pulse duration of 0.7 ms; a spot diameter of 0.8 mm; and a wavelength of 1000 nm. Further, a third vascular treatment pulse may have a fluence of 12 J/cm2; a pulse duration of 13 ms; a spot diameter of 2 mm; and a wavelength of 600 nm. It will be appreciated that a treatment algorithm analyzing an image area may identify multiple sub-areas within a target skin area (e.g., a lesion) and may specify vascular pulse parameters specific to each sub-area. In another example, a first pigmented treatment pulse 1252 (FIG. 12) may have a fluence of 0.3 J/cm2; a pulse duration of 1.0 ns; a spot diameter of 0.4 mm; and a wavelength of 725 nm, while a second pigmented treatment pulse may have a fluence of 0.5 J/cm2; a pulse duration of 1.1 ns; a spot diameter of 0.3 mm; and a wavelength of 710 nm. Alternatively, the second pigmented treatment pulse may have a fluence of 1.2 J/cm2; a pulse duration of 50 ns; a spot diameter of 0.66 mm; and a wavelength of 550 nm. Further, a pigmented treatment pulse may have a fluence of 3 J/cm2; a pulse duration of 3 ns; a spot diameter of 0.7 mm; and a wavelength of 980 nm. In another example, the first remodeling (e.g., collagen) treatment pulse 1326 may have a fluence of 1.1 J/cm2; a pulse duration of 50 ns; a spot diameter of 0.1 mm; and a wavelength of 1064 nm, while a second remodeling treatment pulse may have a fluence of 1.0 J/cm2; a pulse duration of 45 ns; a spot diameter of 0.2 mm; and a wavelength of 1064 nm. Alternatively, the second remodeling treatment pulse may have a fluence of 1.1 J/cm2; a pulse duration of 45 ns; a spot diameter of 0.1 mm; and a wavelength of 1064 nm. Further, a third remodeling treatment pulse may have a fluence of 5.0 J/cm2; a pulse duration of 0.5 ns; a spot diameter of 0.5 mm; and a wavelength of 1064 nm.

Figure 14:
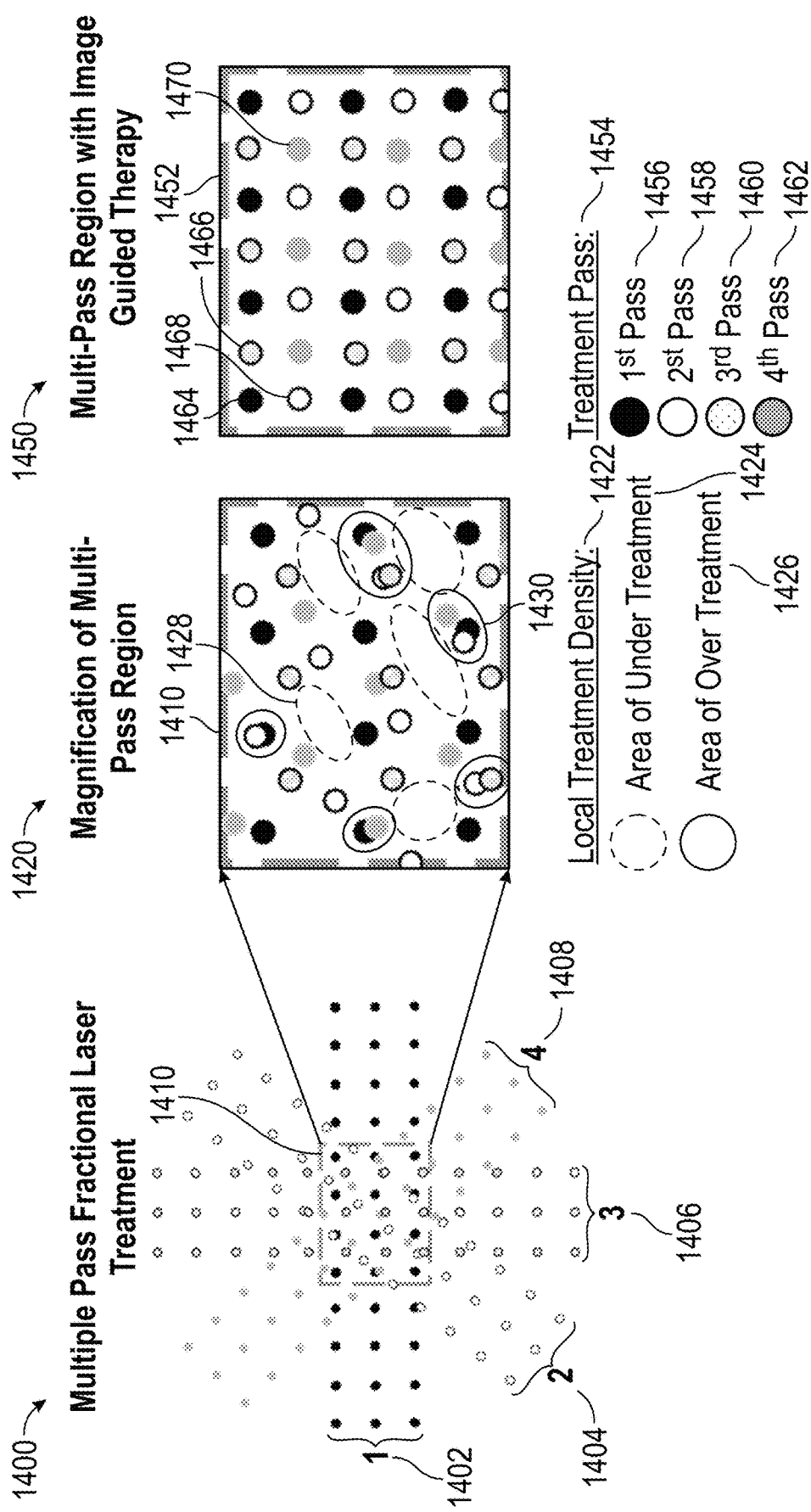
FIG. 14 is an illustration of a results comparison of different treatment procedures, according to one embodiment.

FIG. 14 is an illustration of a results comparison of different fractional laser treatment procedures, according to the prior art and one embodiment of the present disclosure. Fractional treatments, discussed above in connection with FIGS. 9A and 9B, offer several potential advantages compared to non-fractional treatments in which the entirety of a target skin area is treated (e.g., faster healing, reduced overtreatment and associated discomfort). However, except for fractional treatments involving low density coverage (e.g., 5% or less of the area of a target skin area selected for treatment, current methods of providing higher-coverage fractional treatments of a target skin area create progressively higher risks of providing zones of undertreatment as well as overtreatment within the target skin area receiving fractional treatment. Certain embodiments of the present disclosure provide improved systems and methods for providing a desired fractional treatment density (i.e., the percent or fraction of the target skin area that receives one or more laser pulses) of a target skin area such as a lesion.

A preferred method to achieve a desired fractional treatment density of a target skin area is to apply multiple lower density passes to the target skin area. For example, a cumulative treatment density of 30% may be achieved by applying 6 passes each having a 5% treatment density. To facilitate the application of multiple passes, the handpiece is typically equipped with rollers so it may be moved across the skin in a smooth, "painting" type motion. This technique is preferred because it offers multiple benefits compared to a single-pass treatment of a target skin area applied at the final treatment density. First, treatment using multiple, low density passes provides time for waste heat from a given treatment pass to dissipate before more energy is applied to the target skin area in a subsequent pass. This limits the macroscopic buildup of heat in the skin outside the treatment spots, and thereby reduces patient discomfort and the risk of adverse thermally initiated events such as erythema, edema, or blistering. Consequently, a higher final treatment density can also be achieved using the multi-pass technique, which allows the operator to manually adjust the cumulative treatment density in real time to accommodate macroscopic spatial variations in lesion density and tissue sensitivity by controlling the number of passes applied to a given area.

Despite these advantages, the manner in which the multi-pass technique is implemented in the field today has a significant limitation. In particular, the technique produces a final treatment pattern of laser spots across the treatment area that are not regularly spaced, but rather resembles more of a random distribution. A fundamental premise of fractional laser therapy is that for a particular lesion and set of laser treatment parameters, there exists an optimum treatment density that maximizes efficacy and minimizes recovery time. The current implementation cannot achieve this optimum and therefore limits the quality of clinical outcomes.

The root cause of this limitation in current devices can be understood by reviewing how commercial devices generate the cumulative treatment pattern for the multi-pass technique. First, the speed at which the handpiece is traversed across the skin (the "hand speed") is calculated by using a sensor (typically optical or electro-magnetic) to measure the rate of rotation of the rollers. This information is then used to adjust the pulse repetition rate of the laser and the rate the scanner in the handpiece sweeps the beam across the skin to produce a pattern of equally spaced treatment spots (a fixed treatment density), independent of variations in hand speed. The limitations arise because subsequent passes (e.g., a 2nd, 3rd, or Nth pass) over the treatment area are not synchronized in any way with any of the earlier passes. Consequently, the treatment patterns for each pass are spatially shifted in a random manner, and the cumulative treatment pattern approaches a random pattern as the number of passes is increased. However, because the individual passes are not each randomly oriented with respect to one another, the net result over a series of overlaid passes in a target skin area is not a uniformly distributed set of treatment pulses, but an area having sub-areas of evenly spaced treatments as well as sub-areas of over-treatment and undertreatment, as shown more clearly in illustration 1420.

FIG. 14 includes 3 illustrations 1400, 1420, and 1450, with illustration 1400 depicting a generally circular skin area in which four treatment passes (1402, 1404, 1406, 1408), each having the same fractional coverage percentage, are applied at angles to one another in different portions of the circular skin area. A treatment pass legend 1454 indicates shading that distinguish between the laser pulses 1456 associated with first pass 1402, laser pulses 1458 associated with second pass 1404, laser pulses 1460 associated with third pass 1406 and laser pulses 1462 associated with fourth pass 1408. Referring again to illustration 1400, a central target skin area 1410 represents a common target skin area through which a portion of each of the four treatment passes 1402, 1404, 1406, 1408 travels. As each treatment pass 1402-1408 approaches, travels through, and travels away from the central target skin area 1410, areas of overlap are created between the laser pulses of each treatment pass, including the central target area which includes pulses from each of the four treatment passes.

Although it may appear in illustration 1400 that the pulses 1456, 1458, 1460, and 1462 within central target skin area 1410 are randomly distributed, an enlarged view of the central target skin area, shown in central illustration 1420, reveals more clearly that areas of undertreatment 1428 and overtreatment 1430 exist therein. A legend 1422 designates areas of undertreatment 1428 by dotted-line circular or oval shapes 1424 to indicate areas where no treatment pulses are provided, and areas of overtreatment 1430 by solid-line circular or oval shapes 1426, where one or more laser pulses from different passes at least partially overlap on areas that have received two laser pulses.

In one embodiment of the present disclosure, methods and systems are provided to reduce areas of undertreatment 1428 and/or overtreatment 1430. Illustration 1450 depicts a distribution of pulses within the central target skin area using image-guided therapy methods as previously described herein. In particular, an image may be captured that includes central target skin area 1410. A high-density fractional treatment of the central target skin area 1410 (and alternatively a less dense fractional treatment of the remainder of the generally circular skin area shown in illustration 1400) may be provided in which the pulses of each pass across the central target skin area 1410 (and/or the larger generally circular area of illustration 1400) are uniformly distributed based on an image of which the central target skin area is a portion. The high-density fractional treatment shown in illustration 1450 may be achieved using one or more of the methods of FIGS. 18, 19, 20, 21, 22, and/or 23.

Figure 15:
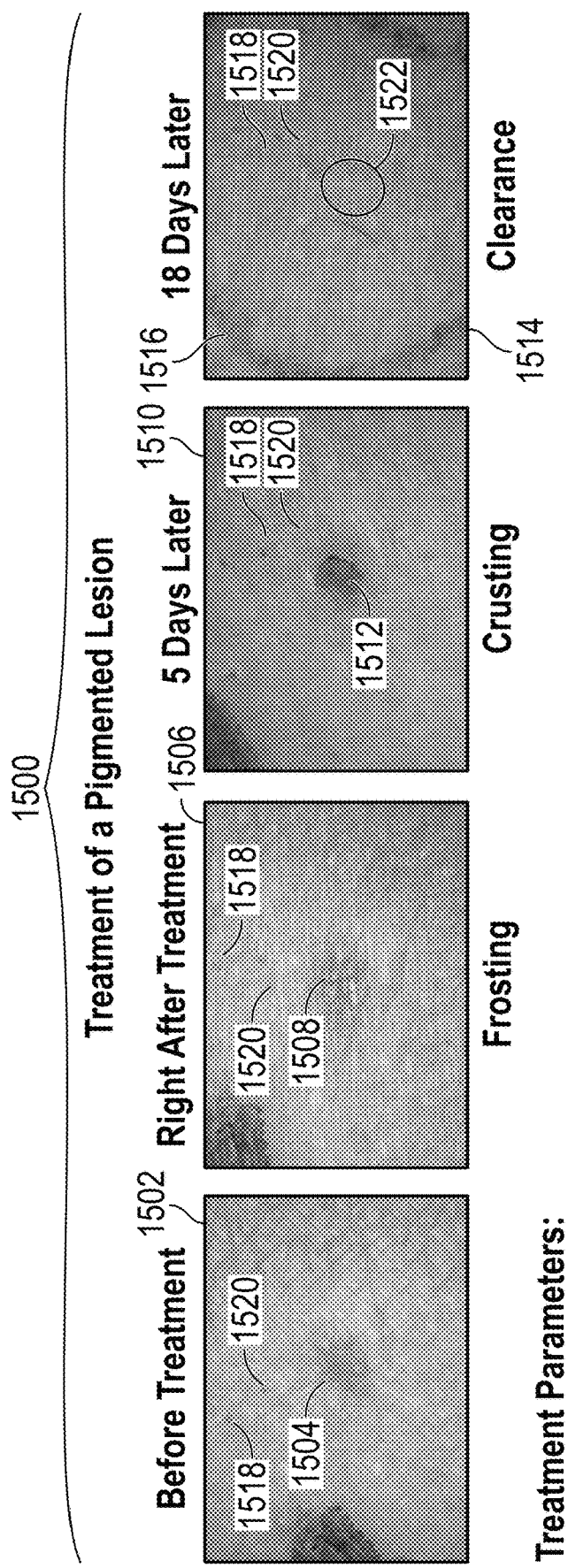
FIG. 15 is a clinical illustration of one of the treatment procedures, according to one embodiment.

In FIG. 15, a clinical illustration 1500 of the effects of a treatment method is shown, according to one embodiment. A before treatment image 1502 shows a first marker 1518, a second marker 1520, and a target skin area 1504. A treatment image 1506 taken immediately after treatment shows the target skin area 1508 in a frosting condition. A treatment image 1510 taken five days after treatment shows the target skin area 1512 in a crusting condition. Finally, a treatment image 1514 taken eighteen days after treatment shows that the treated area 1522 has become nearly indistinguishable from the surrounding skin area but can be located based on its position relative to the first marker 1518 and the second marker 1520. The target skin area 1522 is in a clearance or healed condition.

To better understand how reducing the spot size affects treatment depth, a study was performed to simulate the propagation of laser light in skin for spot diameters of 3 mm and 0.3 mm. A spot size of 0.3 mm should be adequate to treat most lesions with high spatial resolution, since most lesions have a width of 0.5 mm or more. A laser wavelength of 532 nm was used for the simulation and the laser beam was modeled as having either a top-hat or Gaussian intensity profile (this wavelength and beam profiles are commonly used for treating skin lesions). A computer model of skin was created consisting of 0.1 mm thick epidermal and 2 mm thick dermal layers. Optical scattering and absorption coefficients for each layer were included and a Monte Carlo algorithm was used to propagate the light in the tissue in 3 dimensions. To compare the conditions required to achieve equal therapeutic effect, an arbitrary incident power of 1 Watt (W) was chosen for the 3 mm top-hat beam, and the power for the 0.3 mm top-hat beam was then adjusted so the light intensity along the beam axis matched that of the 3 mm beam at the dermal-epidermal (DE) junction (0.1 mm depth in tissue). The intensities were matched at this depth since this is where the target tissue for pigmented lesions (epidermal basal layer) and superficial vascular lesions (dermal papillary layer) is located. Propagation of a 0.4 mm Gaussian beam (1/e2 diameter) was also simulated. Incident powers of 1.5 W and 1.7 W were required for the 0.3 mm and 0.4 mm diameter beams to match the intensity of the 1 W, 3 mm beam at the DE junction. Cross sections of the 3-dimensional light intensity distribution taken through the beam axis are plotted versus depth and radial distance from the beam axis for the 3 mm and 0.3 mm beams in FIG. 16A and FIG. 16B, respectively. Isointensity lines have been added to aid comparison of how the intensity decreases with depth. FIG. 16C shows the intensity for all beams versus depth along the beam axis.

Spot sizes used in current systems typically require incident intensities to be set close to the threshold of damaging surrounding non-lesion tissue to achieve high efficacy in clearing lesions. Therefore, the need for significantly higher incident power for smaller beams would seem to preclude their clinical utility. However, analysis of the result in FIGS. 16A-C leads to a non-intuitive conclusion that this is not the case due to two effects.

First, FIG. 16C shows that although the required incident power of the 0.3 mm top-hat beam is 50% higher as delivered from the laser, the maximum intensity within the skin is only 11% higher. The smaller difference in intensities in the tissue is due to scattering of light from the edges of the beam towards the beam center, which increases the intensity of light along the beam axis. This effect is less pronounced for beam sizes <2 mm and offsets the higher power required of the 0.3 mm beam.

Second, in the superficial portion of the epidermis (depth <0.05 mm) where the difference in light intensity is the highest, the concentration of light absorbing tissue chromophores is relatively low. In general, the absorbing chromophores are localized close to the DE junction (Dermis and Epidermis Junction). For example, the concentration of melanin increases monotonically by a factor of 2 from the skin surface to the DE junction and hemoglobin is confined to blood vessels that are located in the papillary dermis, just beneath the DE junction. Therefore, the degree of laser-tissue interaction is lower in the epidermis, and the threshold intensity for overtreatment of epidermal (vs. dermal) tissue is higher. Stated differently, the higher power required for smaller diameter beams to achieve the same relative intensity at the DE junction is better tolerated in the epidermis because there are relatively fewer structures that will be damaged (and cause pain) compared to the dermis. And because the intensity of smaller diameter beams falls off more rapidly from the skin surface compared to larger diameter beams, the higher initial power of the smaller diameter beams disappears entirely at the DE junction, as shown in FIG. 16C and explained more fully below.

Figure 16A:
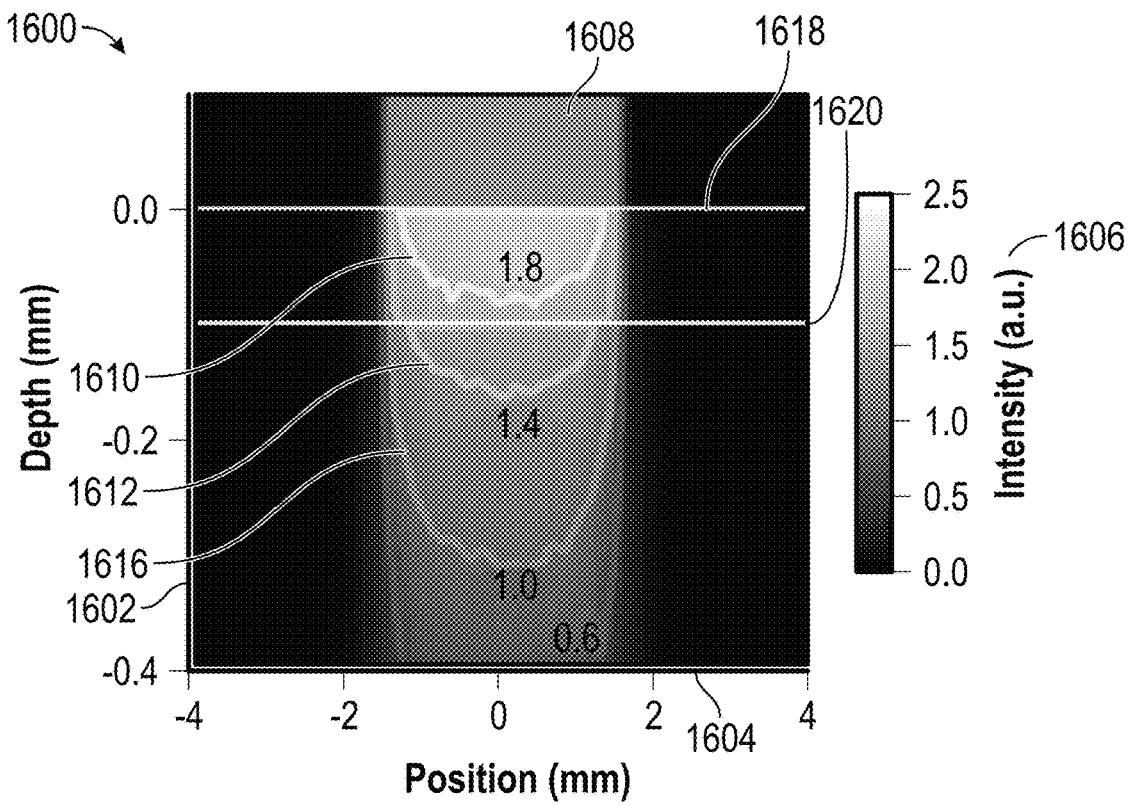
FIGS. 16A-C are illustrations of light and/or energy penetrations into skin tissue of lasers having different spot sizes and intensities, according to one embodiment.
Figure 16B:
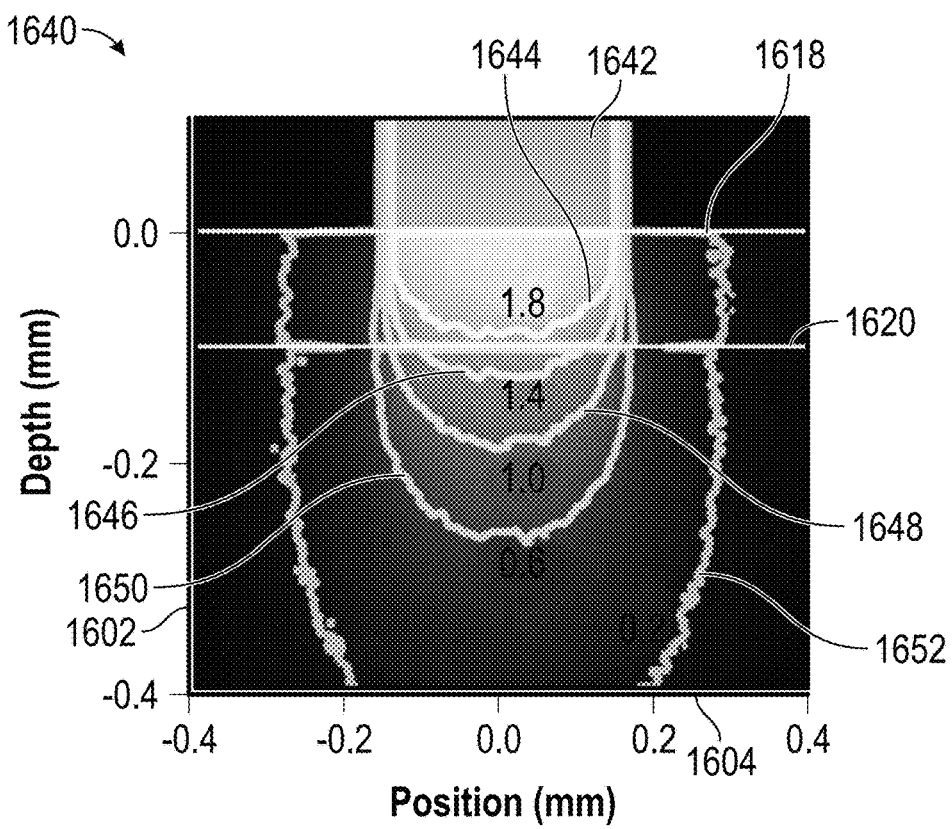
Figure 16C:
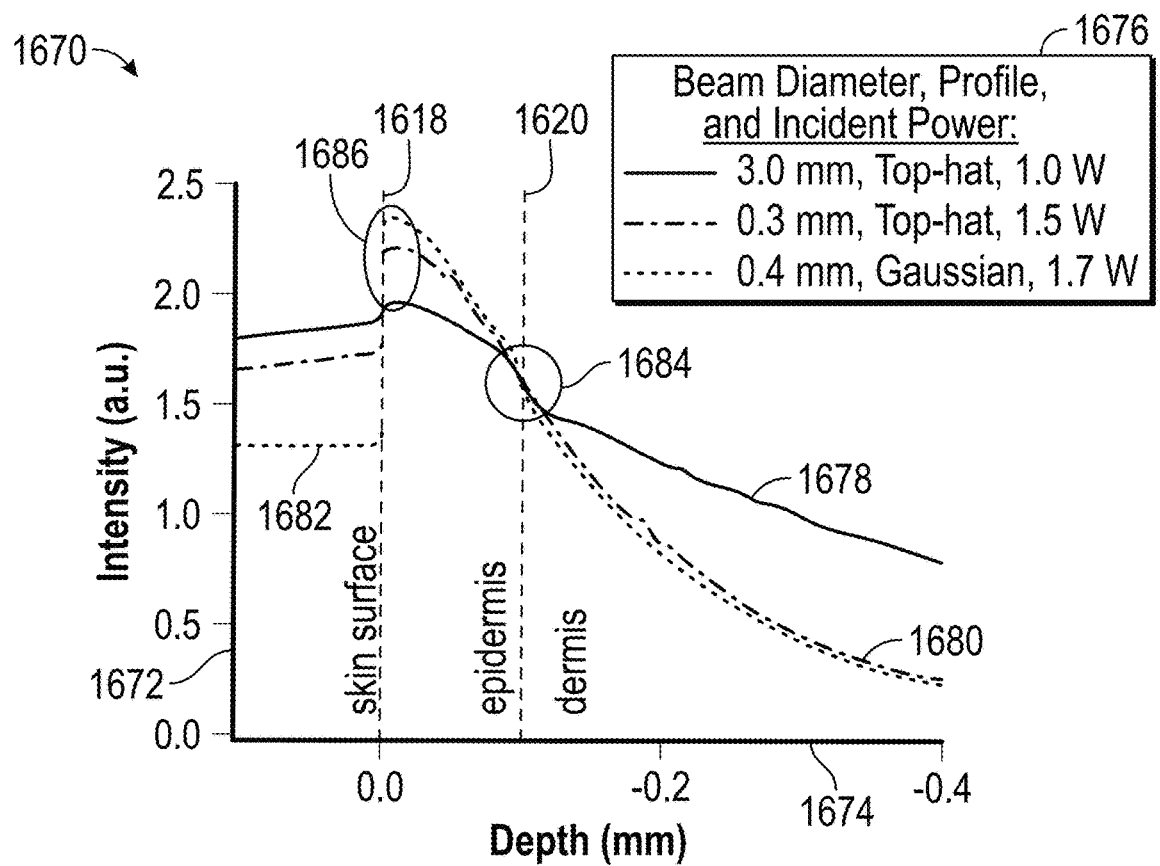

FIGS. 16A-C show Monte-Carlo simulation results for propagation of a 532 nm wavelength laser beam in skin. FIG. 16A shows a first image 1600 which may include a depth axis 1602, a position axis 1604, a first light 1608, a first isointensity line 1610, a second isointensity line 1612, a third isointensity line 1616, a skin surface line 1618, and/or a Dermis and Epidermis Junction line 1620. In this example, the first light 1608 corresponds to a 1 W, 3 mm diameter beam, which results in a beam having the first isointensity line 1610, the second isointensity line 1612, and the third isointensity line 1616. A first legend 1606 illustrates relative intensity of first light 1608 at various positions within the skin via a color graph. FIG. 16B shows a second image 1640 which may include a second light 1642 corresponding to a 1.5 W, 0.3 mm diameter beam, which creates a first isointensity line 1644, a second isointensity line 1646, a third isointensity line 1648, a fourth isointensity line 1650, and a fifth isointensity line 1652.

FIG. 16C shows a third image 1670 which may include a relative intensity (power per unit area) axis 1672, a depth axis 1674, a first legend 1676, a first line 1678, a second line 1680, a third line 1682, a Dermis and Epidermis Junction depth 1684, and/or a skin surface depth 1686. The first legend 1676 identifies the first line 1678 (corresponding to a 3 mm, 1 W tophat beam), the second line 1680 (corresponding to a 0.3 mm, 1.5 W tophat beam), and the third line 1682 (corresponding to a 0.4 mm, 1.7 W Gaussian beam). Each of the lines 1678, 1680, and 1682 illustrates the intensity vs depth for the respective laser beam associated with the line. The power level from the 0.3 mm diameter beam is 50% higher (1.5 W vs 1.0 W) than the power level from the 3.0 mm diameter beam, and the power level of the 0.4 mm diameter beam is 70% higher (1.7 W) than 3.0 mm diameter beam. Given their much smaller area, it would be expected that the relative intensity for the 0.3 and 0.4 mm beams would be significantly greater than that of the larger 3.0 mmm beam. However, in both instances, the relative intensity of the smaller beams near the skin surface are less than that of the larger 3.0 mm beam because of backscattering from the surface of the skin. In particular, it can be seen to the immediate left of the skin surface that the relative intensity of the 3.0 mm beam rises from about 1.8 to 1.9 at the skin surface, while the 0.3 mm beam risk from about 1.7 to about 1.75 at the skin surface, and the 0.4 mm beam remains essentially flat in the same region at about 1.3. The smaller beams have significantly less reflected backscatter from the beam that the larger beam. In addition, the 0.4 mm beam has a further reduction in backscatter because its profile of intensity across the beam is Gaussian instead of tophat, further reducing reflected backscatter into the beam.

Because the smaller beams have a significantly higher power and much smaller area, their relative intensities at the surface rise more significantly than the larger beam. In one example, a first area 1686 shows the various relative intensity levels for each beam at the skin surface (line 1618). In particular, the 3.0 mm diameter, 1 W beam has a relative intensity at the skin surface slightly below 2.0. Conversely, the relative intensity for the 0.3 mm diameter beam at a power level of 1.5 W at the skin surface is approximately 2.22 which is higher than that of the 3.0 mm beam, but only by 11%—significantly closer to the larger beam than would be expected based on beam power and diameter alone, again due to the much higher scattering in the skin of the light of the 3.0 mm diameter beam. Therefore, even though the power level from the 0.3 mm diameter beam is 50% greater than the power level from the 3.0 mm diameter beam, the intensity for the 0.3 mm diameter beam is only 11% higher than the intensity for the 3.0 mm diameter beam at the skin surface 1618.

Similarly, first area 1686 likewise shows that the relative intensity for the 0.4 mm diameter beam at a power level of 1.7 W at the skin surface is approximately 2.3 which is only 15% higher than the 3.0 mm diameter beam. Therefore, even though the power level from the 0.4 mm diameter beam is 70% greater than the power level from the 3.0 mm diameter beam, and its area is approximately 56 times smaller than the 3.0 mm beam, the intensity for the 0.4 mm diameter beam is only 15% higher than the intensity for the 3.0 mm diameter beam at the skin surface 1618. Thus, FIG. 16C illustrates that smaller beams, though seemingly involving perhaps as much as 50 or more times the relative intensity of the larger beam, in fact provide slightly more but relatively comparable relative intensities for power levels sufficient to achieve treatable levels of intensity at the DE junction. This is shown by second area 1684 of FIG. 16C, which shows that the intensities for the first line 1678 (3 mm beam), the second line 1680 (0.3 mm beam), and the third line 1682 (0.4 mm beam) have similar intensities at the dermal/epidermal (D/E) junction 1620.

Referring again to FIG. 16A, a cross section of the 3-dimensional light intensity distribution taken through the beam axis plotted versus depth and radial distance from the beam axis for a 1 W, 3 mm diameter beam with a top-hat intensity profile is shown. In FIG. 16B, a cross section for a 1.5 W, 0.3 mm diameter beam with a top-hat intensity profile is shown. In FIG. 16C, intensity profiles along beam axis for the 3 mm and 0.3 mm top-hat beams and a 1.7 W, 0.4 mm diameter Gaussian beam are shown. FIGS. 16A and 16B, together with the relative intensity graph of FIG. 16C, show that contrary to conventional expectations, it is possible to achieve similar intensities at the D/E junction using a 0.3 mm beam that is only ¹⁄₁₀th the width of a typical 3 mm beam often used as the smallest spot size for many dermatological laser treatment systems. Together with the automatic mapping and automated laser pulse delivery control disclosed in the present disclosure, systems and methods of treatment can be provided to achieve greater treatment efficacy, reduced pain and overtreatment, faster treatment times, and more precise targeting of lesions for a variety of dermatological conditions.

In consideration of the discussion above, the present disclosure defines a method and device design for providing Image-Guided Laser Therapy of skin lesions and eliminates the need to manually align the beam to lesions and select treatment parameters in a sequential manner without the benefit of medical diagnostic data provided by an imaging system. In general, the system is designed such that the illumination sources, camera, and scanner cover a treatment area that contains a plurality of lesions, which enables analysis and determination of treatment parameters (and in some embodiments automatically implementing treatment) with greater precision and speed than allowed by current systems. In one modality, the treatment area is imaged, treated and then the hand piece is moved to an adjacent area for treatment if the lesions in the adjacent area until the entire region of interest (for example the sides of a face) is treated. In another modality, the hand piece is moved in a continuous fashion and motion sensors in the hand piece measure the hand piece displacement such that the spatial coordinates of lesions may be updated in real time as they move across the field of view of the camera, preferably at a sampling or update rate of 100 to 10,000 times per second to ensure that laser pulses can be delivered to a desired location in a target skin area on a timescale that is significantly faster than the movement of the handpiece by the user.

Figure 17:
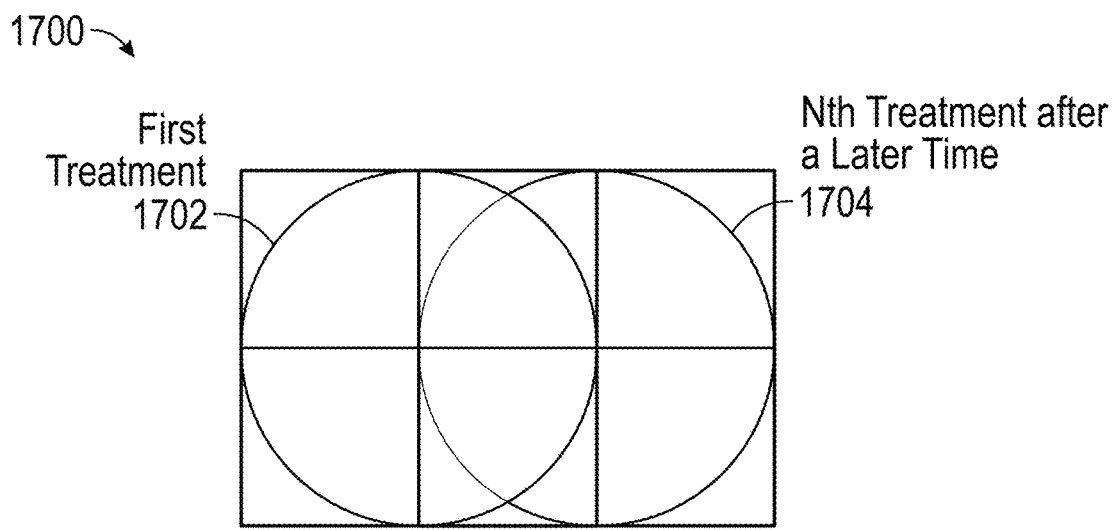
FIG. 17 is an illustration of a treatment procedure, according to one embodiment.

FIG. 17 shows a first treatment beam 1702 and an Nth treatment beam 1704 where the first treatment beam 1702 and the Nth treatment beam 1704 overlap coverage areas. In addition, the Nth treatment beam 1704 may be initiated after a delta time has elapsed between the termination of the first treatment beam 1702, which allows the treatment area to partially or fully recover from the application of the first treatment beam 1702 before the Nth treatment beam 1704 is applied. In one example, by delaying the Nth treatment beam 1704, the area already treated by the first treatment beam 1702 may have sufficient time to recover which reduces or minimizes negative effects from double treatments of the overlap area.

Figure 18:
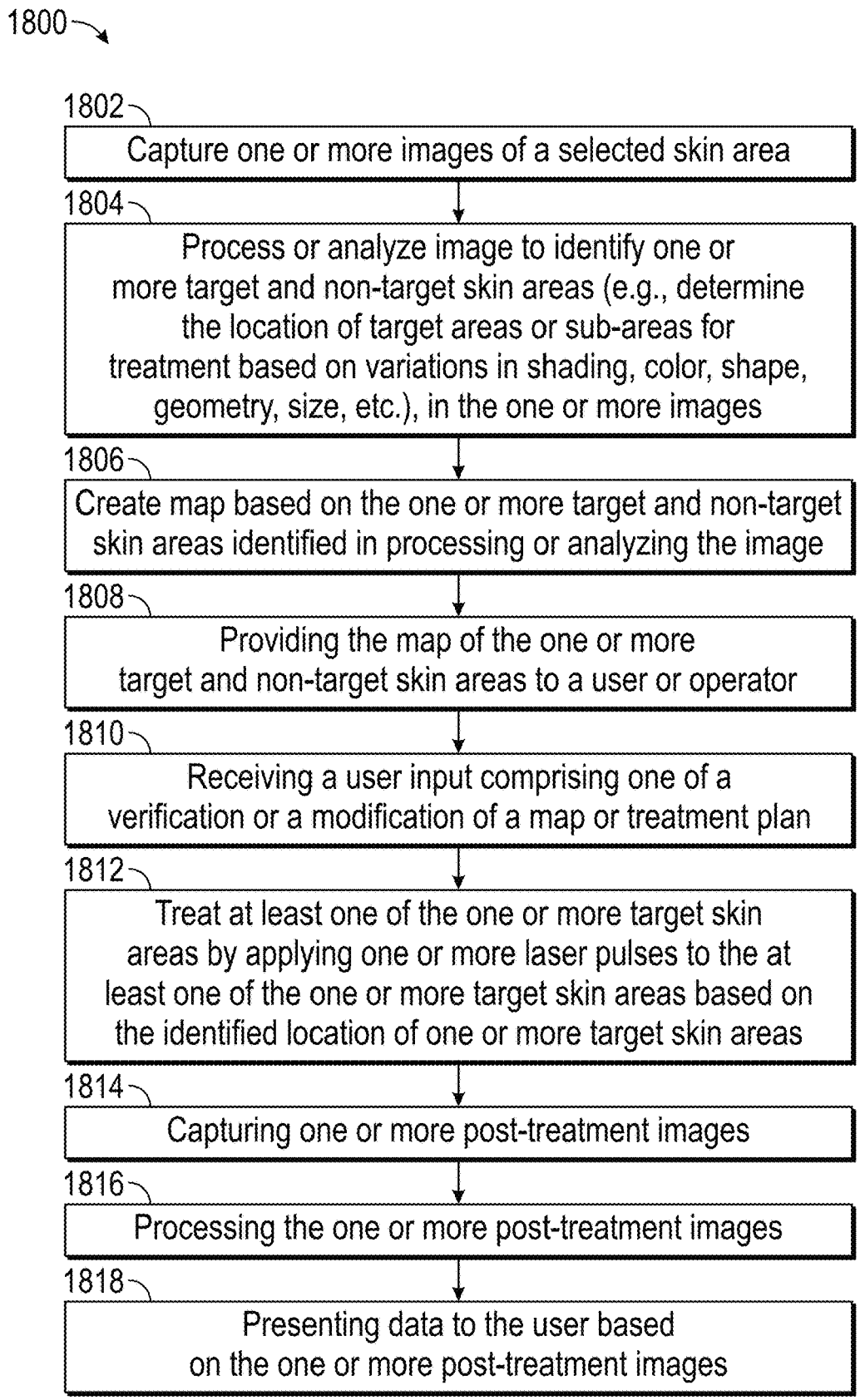
FIG. 18 is a treatment flow chart, according to one embodiment.

In FIG. 18, a treatment method 1800 is shown, according to one embodiment. Each and every combination of steps shown in the treatment method 1800 is hereby disclosed in this disclosure. Therefore, each and every step may be combined with any of the other steps and/or each and every step may be optional (and therefore omitted in a treatment). The treatment method may include capturing one or more images of a first or selected skin area that includes one or more target skin areas (e.g., areas within the imaged skin area that are to be treated) and non-target areas (e.g., areas within the imaged area for which no treatment is intended), using an imaging device (step 1802). Capturing an image may include illuminating a skin area with a light source emitting one or more of ultraviolet, visible, or infrared light (e.g., using an LED device) while the image is captured. Capturing one or more images may further comprising capturing a plurality of images under different lighting conditions (e.g., capturing one or more first images under ultraviolet lighting conditions, capturing one or more second images under visible lighting conditions, and capturing one or more third images using infrared (e.g., near infrared or NIR) lighting conditions).

The treatment method may include processing or analyzing the captured one or more images to identify one or more target skin areas (e.g., lesions or portions thereof) to receive laser pulses in at least a portion thereof, and non-target areas (step 1804). Processing the captured image may include one or more of: determining the location of one or more target skin areas (e.g., by performing a segmentation algorithm of the image to identify areas and/or sub-areas to be treated); classifying target skin areas/sub-areas for treatment (e.g., identifying a lesion type for each area or sub-area to be treated); and/or identifying variations in coloring or shading within the captured image(s), which may be used in turn to identify and/or classify the target skin areas and/or to determine treatment parameters. Determining the target skin areas within the captured image(s) may involve processing the image to identify areas based on one or more of shading, coloring, shape, geometry, size, etc. In one embodiment, the step of identifying target and non-target skin areas comprises processing or analyzing the one or more captured image(s) on a pixel-by-pixel basis (e.g., analyzing each pixel to determine if the skin area represented by the pixel is a target skin area or a non-target skin area), on a multi-pixel basis (e.g., areas comprising 4×4 pixels, 8×8 pixels), or areas corresponding to at least one laser beam size (e.g., a laser spot diameter) ranging in size from 0.03 mm to 2.0 mm), a lesion-by-lesion basis, and/or by identifying one or more groups of contiguous pixels for which at least a threshold percentage (e.g., 100%, 90%, 80%, 75%, 50%, etc.) of the pixels comprising the area should be treated in step 1812.

In a further embodiment, processing or analyzing the captured one or more images may include determining a treatment plan for target skin areas (e.g., by determining a pulse delivery location for one or more treatment pulses to target skin areas). In one embodiment, analyzing the processed image may include determining the location where each of a plurality of treatment pulses is to be applied to target skin areas within the imaged skin area, as illustrated in FIGS. 9A-B, first and second images 1000, 1050 (FIG. 10), first and second treatment pass maps 1220, 1250 (FIG. 12), and multi-factorial fractional treatment map 1320 of FIG. 13.

The treatment method may further include creating a map based on the target skin areas and non-target skin areas identified in processing or analyzing the image (step 1806). In one embodiment, this may involve generating a map showing target and non-target skin areas within the imaged skin area (e.g., an image showing target regions to be treated and non-target areas to be left untreated), such as by assigning spatial coordinates and/or treatment settings to target and non-target areas. In one embodiment, the map may illustrate target skin areas alone (e.g., with no indication of a lesion type or treatment parameters), while in another embodiment, the map may illustrate both target and/or non-target skin areas as well as additional information associated with the target skin areas (e.g., lesion type, size, or severity, treatment parameter(s), etc.). In one embodiment, the map may comprise a graphical or numerical representation of the captured and/or processed image identifying one or more target skin areas non-target skin areas.

The treatment method 1800 may also include providing the map of target and non-target skin areas to a user and/or operator (step 1808). Providing the map to a user (1808) may involve presenting a graphical or numerical representation identifying (e.g., by coloring, shading, numerical symbols, and/or graphical symbols) the one or more target skin areas and/or non-target skin areas in the captured or processed image or a portion thereof. In some embodiments, the presentation of map(s) to the user (1808) may also include presenting a treatment plan for the one or more target skin areas. In one embodiment, presenting the treatment plan may comprise displaying treatment parameters and/or laser spots overlaid on portions of the processed image (e.g., displaying a visual indication of where laser pulses would be applied to the one or more target skin areas). In some embodiments, displaying the map may include indicating where portions of laser pulses would extend outside of a target skin area and into a non-target skin area. In an alternative embodiment, a written treatment plan may be presented separately from the map. Presenting the map (with or without a treatment plan) may include displaying the map a screen or monitor for review or consideration.

The treatment method 1800 may include receiving a user or operator input response (e.g., verifying or modifying) one or more of the treatment plan and/or the treatment map (step 1810) presented to the user in step 1808. In some embodiments, the step of displaying the map 1808 may comprising displaying an interactive map that allows the user to manipulate the display of the map (e.g., by zooming in or out of the image or particular treatment or non-treatment areas to diagnose or verify a diagnosed lesion identified in the displayed map, or by toggling between ultraviolet, visible, and/or infrared views of the image or a portion thereof). The user may provide one or more inputs (e.g., via a touchscreen or other input/output device) to verify, confirm, and/or modify the treatment map and/or plan.

The treatment method 1800 may include treating at least one of the one or more target skin areas based on the processing or analyzing of the captured one or more images (1812). In one embodiment, treating step 1812 comprises applying one or more laser pulses to each of the target skin areas identified in step 1804. In one embodiment, treating step 1812 may be based on one or more of the maps created in step 1806, the map or treatment plan provided to the user in step 1808, or the map or treatment plan as verified or modified by the user in step 1810. In one embodiment, method 1800 omits one or more of steps 1806, 1808, and 1810, and the treating step 1812 is based directly on the processing or analyzing of the captured one or more images in step 1804. In yet another embodiment, the treating step 1812 comprises automatically applying one or more laser pulses to at least one target skin areas based on the processing or analysis of the image in step 1804. This may include, e.g., providing a controller to automatically control the delivery of laser pulses to one or more target skin areas by, e.g., controlling the positioning of a movable mirror used to direct laser pulses to the patient's skin. In one embodiment, a controller controls the position of a movable mirror by controlling the operation of one or more motors controlling the position of the movable mirror in one, two, or three axes.

In some embodiments, treatment method 1800 may further include capturing an image after treating at least a portion of the one or more target skin areas (step 1814). Capturing one or more post-treatment images may include capturing one or more images at any of a variety of time-points, including without limitation capturing one or more images: 1) after delivering at least one pulse but less than all of the treatment pulses (e.g., capturing intra-treatment/partial-treatment images); 2) at a predetermined time interval following a treatment of a particular pulse; 3) at a predetermined time interval following a treatment pass; 4) after treatment of the entirety of a target skin area; or 5) after treatment of all target skin areas within the imaged skin area.

Treatment method 1800 may further include processing the one or more after-treatment images (step 1816), which may include determining one or more results or effects of treatment step 1812. Processing the one or more after-treatment images may be performed for a variety of purposes including verification or assessment of therapy efficacy, identification of one or more areas of overtreatment or undertreatment, identification of side effects, determining that additional treatment pulses are needed, etc.

Treatment method 1800 may further include presenting data to the user based on the one or more post-treatment images (step 1818). The data presented may include a variety of information such as a follow-up treatment plan, a before-and-after comparison, an assessment-of-efficacy report, an adverse event report, a side effect report, etc. In one example, a patient may be shown a before-treatment image (e.g., image 1502, FIG. 15) and a post-treatment image (e.g., image 1514, FIG. 15) to show the results or efficacy of the treatment step 1812. In one embodiment, one or more follow-up treatment plans may be generated and presented to the user based at least in part on the after-treatment image as captured or processed. For example, a patient may complete a vascular treatment and the system, device, and/or method may determine that a pigmented lesion and/or remodeling/collagen treatment should be performed subsequent to the vascular treatment. Reports may be generated and/or displayed for the patient may include both positive and negative indications of efficacy (e.g., indications that the treatment was successful, unsuccessful, and/or resulted in one or more adverse events). Step 1818 may also include storing the data presented to the user and/or storing data collected during one or more other steps of the treatment method 1800.

In preferred embodiments, the step of processing or analyzing the image (1804) is employed to guide the treatment step (1812). In one example, step 1804 may include analyzing the captured images to identify one or more lesions. Such an identification is shown in, e.g., first image 500 of FIG. 5A, previously discussed, where the processing step 1804 may be used to identify first lesion 506, second lesion 508, third lesion 510, fourth lesion 512, and Nth lesion 514 based, e.g., on different shading/colors, different sizes and different shapes or configurations in the captured image(s).

In one embodiment, the step of analyzing the image (1804) is employed to guide the treatment step (1812) by determining boundaries of each of the one or more target skin areas, such as first lesion boundary 538, second lesion boundary 534, third lesion boundary 536, fourth lesion boundary 542, and Nth lesion boundary 540 as previously discussed in connection with FIG. 5B.

Figure 19:
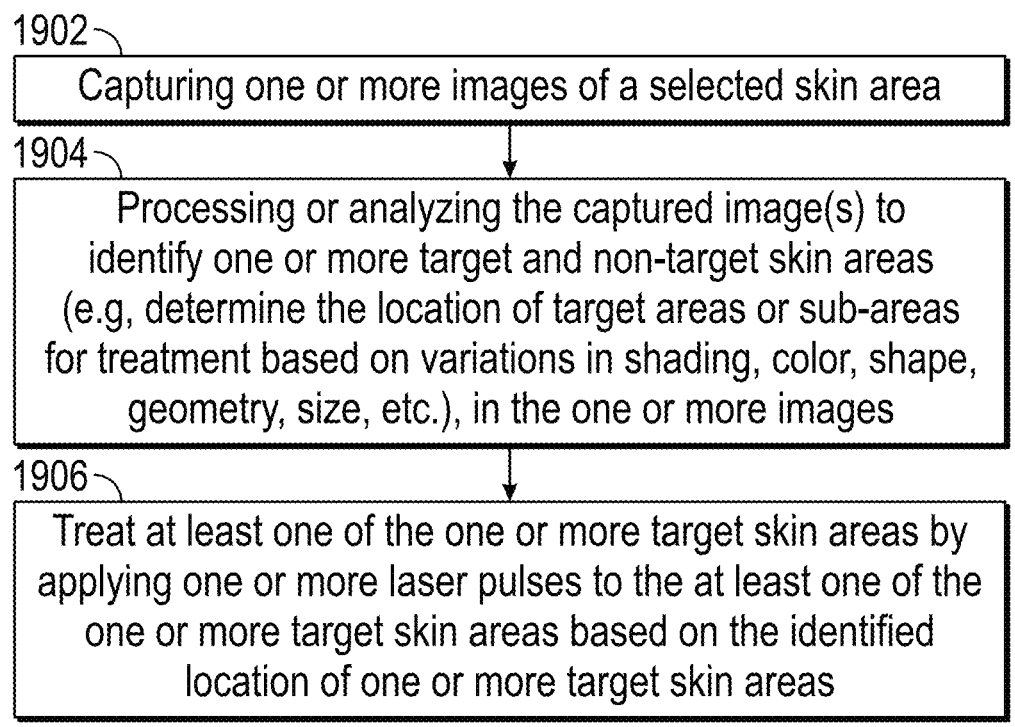
FIG. 19 is a treatment flow chart, according to one embodiment.

In FIG. 19, a treatment method 1900 is shown, according to one embodiment. The treatment method 1900 may include capturing one or more images of a first or selected skin area that includes one or more target skin areas (e.g., lesions) and non-target areas (e.g., non-lesion or clear skin areas) (step 1902). Capturing the one or more images may be performed while illuminating the skin areas with one or more of ultraviolet, visible, or infrared light while the image is captured, and may involve capturing a plurality of images under different lighting conditions (e.g., capturing one or more first images under ultraviolet lighting conditions, capturing one or more second images under visible lighting conditions, and capturing one or more third images using infrared lighting conditions). Capturing one or more images may comprise using a camera, which in various embodiments may comprise a digital camera including a CCD or CMOS image sensor or other digital sensing element, or an analog camera.

The treatment method 1900 may include processing or analyzing the captured one or more images to identify one or more target skin areas and non-target areas (step 1904). Processing the captured image may include one or more of: identifying variations in coloring or shading within the captured image(s) (which may be used to identify, classify, or determine treatment parameters for target skin areas); determining the location of the one or more target skin areas (e.g., using a segmentation algorithm of the image); and classifying target skin areas/sub-areas for treatment (e.g., identifying one or more lesion types for each target skin area or sub-area). Determining the location of the target skin areas within the captured image(s) may involve processing the image to identify areas based on one or more of shading, coloring, shape, geometry, size, etc. The step of identifying target and non-target skin areas comprises processing or analyzing the one or more captured image(s) on a pixel-by-pixel basis, a multi-pixel basis, or a lesion-by-lesion basis, or by identifying one or more groups of contiguous pixels for which at least a threshold percentage (e.g., 100%, 90%, 80%, 75%, 50%, 40, etc.) of the total area of the target skin area should be treated with laser pulses.

The treatment method 1900 may include treating at least one of the one or more target skin areas based on the processing or analyzing of the captured one or more images (1906). In one embodiment, treating step 1906 comprises applying one or more laser pulses to each of the target skin areas identified in step 1904. In one embodiment, treating step 1906 may comprise applying laser pulses to at least one of the one or more target skin areas based on the image processing or analyzing step 1904.

In some embodiments, the treating step 1906 may be based on one or more maps, treatment plans, or user inputs, as discussed in connection with FIG. 18. In a preferred embodiment, the treating step 1906 comprises automatically applying one or more laser pulses to the one or more target skin areas based on the processing or analysis of the image in step 1904. As used herein, "automatically" refers to the delivery of laser pulses to skin tissue in which the location of the laser pulse is not determined by a user. This may include, e.g., providing a controller to automatically control the delivery of laser pulses to particular locations within the one or more target skin areas. The controller may, for example, control the positioning of a movable mirror used to direct laser pulses to the patient's skin by controlling the operation of one or more motors controlling the position of the movable mirror in one, two, or three axes. In some embodiments, a safety interlock may be provided, requiring that the automatic delivery of the laser pulses to the one or more target skin areas may be initiated only in response to a user input authorizing or triggering the delivery of the laser pulses, but once started may be completed automatically based on the processing or analyzing in step 1904.

Automating (with or without user reviewing or initiation of therapy) the delivery of laser pulses, which the present disclosure facilitates, allows significantly faster and more precise treatment of lesions than currently available, while also ensuring the safety of the patient and user control of the procedure. In one embodiment, the automated delivery of laser pulses to the one or more target skin areas may occur at a frequency exceeding one of 100 pulses per second, 1000 pulses per second, 2000 pulses per second, 5000 pulses per second, or 10,000 pulses per second. In one embodiment, the pulses may be delivered at a pulse delivery rate within the range of 100-10,000 pulses per second, while in another embodiment; the pulses may be delivered at a rate within the range of 1,000-10,000 pulses per second.

In some embodiments, treatment method 1900 may further include capturing one or more images during or after the treating step 1906, and providing data, reports, or other feedback to the user, as discussed in greater detail in connection with FIG. 19.

In FIG. 20, a treatment flow chart of a method of treating one or more target skin areas within a selected skin area comprising non-target skin area and at least one target skin area is shown, according to one embodiment. Each and every combination of steps shown in the treatment flow chart is hereby disclosed herein, and each step in the method may be combined with any of the other steps and/or each and every step may be optional. A treatment method 2000 may include initiating a first laser treatment procedure with a first set of laser pulse parameters on one or more target skin areas (step 2002). The treatment method 2000 may further include initiating a second laser treatment procedure with a second set of laser pulse parameters on the one or more target skin areas (step 2004). The treatment method 2000 may further include initiating an Nth laser treatment procedure with an Nth set of laser pulse parameters on the one or more target areas (step 2006).

One example of the treatment method of FIG. 20 is described with reference to shown in FIG. 12, in which a first treatment procedure is provided by applying a first series laser pulses 1222, . . . , 1224 that together comprise a first treatment pass as shown in first treatment pass map 1220. The pulses 1222, . . . , 1224 in the first pass provide a vascular treatment for lesion 1202, and each of the pulses in the first treatment pass have parameters suitable to treatment of vascular lesions and may be described as a "vascular treatment pulse." Each of the vascular treatment pulses 1222 and every vascular treatment up until the Nth vascular treatment 1224 in the first treatment occurs before initiating a second treatment procedure/pass. The second treatment procedure is provided by applying a second series of laser pulses 1252, . . . , 1254 that together comprise a second treatment pass as shown in map 1250 to treat the lesion 1202. Each of the pulses in the second treatment pass have parameters suitable for treating a pigmented lesion and may be describes as a "pigment treatment pulse." First pigment treatment pulse 1252 and every pigment treatment up until the Nth pigment treatment pulse 1254 occurs during the second treatment, and is completed before initiating another (e.g., third, fourth, Nth, etc.) treatment procedure.

In one example, all of the vascular treatment pulses have the same pulse treatment parameters, e.g., a fluence of between 5 J/cm2 to 20 J/cm2; a pulse duration from 0.5 to 50 ms; a spot diameter of between 0.5 to 2 mm; and/or a wavelength of between 532 to 1064 nm. In another example, all of the pigment treatment pulses have the same pulse treatment parameters, e.g., a fluence of between 0.2 J/cm2 to 5 J/cm2; a pulse duration of between 0.5 to 50 ns; a spot diameter of between 0.2 to 1 mm; and/or a wavelength of between 532 to 1064 nm. In another example, one or more parameters of the vascular or pigment treatment pulses may be changed and/or modified when moving from one treatment spot to another in the first treatment pass or the second treatment pass. For example, a first vascular treatment pulse 1222 may have a fluence of 5 J/cm2; a pulse duration of 0.5 ms; a spot diameter of 1 mm; and a wavelength of 532 nm, while a second vascular treatment pulse may have slightly different parameters that are changed to optimize treatment of a different sub-area of the lesion 1202, while remaining within ranges suitable for treatment of vascular lesions. In a particular example, second vascular treatment pulse may have a fluence of 6 J/cm2; a pulse duration of 0.7 ms; a spot diameter of 1.1 mm; and/or a wavelength of 600 nm. Alternatively, the second vascular treatment pulse may have a fluence of 6 J/cm2; a pulse duration of 0.7 ms; a spot diameter of 1.0 mm; and a wavelength of 532 nm. Further, a third vascular treatment pulse in the first treatment pass may have a fluence of 10 J/cm2; a pulse duration of 3 ms; a spot diameter of 2 mm; and a wavelength of 1000 nm.

In another example, a first pigmented treatment pulse 1252 in the second treatment pass (see map 1250) may have a fluence of 0.2 J/cm2; a pulse duration of 1.5 ns; a spot diameter of 0.3 mm; and a wavelength of 700 nm, and a second pigmented treatment pulse may have a fluence of 0.4 J/cm2; a pulse duration of 1.1 ns; a spot diameter of 0.3 mm; and a wavelength of 700 nm. Alternatively, the second pigmented treatment pulse may have a fluence of 1.1 J/cm2; a pulse duration of 40 ns; a spot diameter of 0.9 mm; and a wavelength of 532 nm. Further, a third (or fourth, or Nth) pigmented treatment pulse may have a fluence of 3 J/cm2; a pulse duration of 3 ns; a spot diameter of 0.7 mm; and a wavelength of 980 nm.

In FIG. 21, a treatment flow chart for treating one or more target skin areas within a selected skin area comprising non-target skin area and at least one target skin area is shown, according to one embodiment. Each and every combination of steps shown in the treatment flow chart is hereby disclosed herein, and each step may be combined with any of the other steps and/or may be optional (and therefore omitted). A treatment method 2100 may include initiating a first laser treatment procedure by applying laser pulses having a first set of laser pulse parameters to at least a first portion of the one or more target skin areas during a first portion of the treatment procedure (step 2102). The treatment method 2100 may include initiating a second laser treatment procedure by applying laser pulses having a second set of laser pulse parameters to at least a second portion of the one or more target skin areas during a second portion of the treatment procedure (step 2104). The treatment method 2100 may further include initiating an Nth laser treatment procedure by applying laser pulses having an Nth set of laser pulse parameters to at least an Nth portion of the one or more target skin areas during an Nth portion of the treatment duration (step 2106).

In one example, vascular treatment pulses, the pigment treatment pulses, and/or the remodeling treatment pulses may be applied to one or more target skin areas as three separate treatment passes. In other words, all of the vascular treatment pulses are applied to the target skin area(s), then all of the pigment treatment pulses are applied to the target skin area(s), and then all of the remodeling treatment pulses are applied to the target skin areas. Such passes may minimize total treatment time by avoiding delays associated with switching parameters between vascular, pigment, and/or remodeling treatment pulses. In another example, some of the vascular treatment pulses are applied, then some of the pigment treatment pulses are applied, and then some of the remodeling treatment pulses are applied, and the treatment pulse application cycles for the different types of treatment pulses may be repeated until all of the treatment areas are treated. This approach may minimize time by applying, e.g., first pulses having a relatively large first beam diameter to treat a relatively large fraction of the target skin areas, then applying second pulses having a second beam diameter smaller than the first beam diameter to treat a second fraction of the target skin areas, followed by applying third pulses having a third beam diameter smaller than the second beam diameter, and applying pulses having progressively smaller beam diameters until one or more desired treatment area constraints (e.g., treatment of a desired fraction or percentage of the total target skin area such as at least 75%, at least 80%, at least 90%, or 100%; avoiding treatment of any non-target skin areas; or treating a total non-target skin area that is less than a desired fraction or percentage of the total or treated target skin area such as no more than 1%, no more than 5%, no more than 10%, no more than 25%, etc.). In another example, the treatment pulses may be applied to the one or more target skin areas in one or more patterns (see FIG. 8), with the type of treatment pulses applied (e.g., vascular, pigment, and/or remodeling) determining which of the above-described treatment approaches is utilized. In another example, multiple laser sources may be used and one or more of the vascular, pigment, and/or remodeling pulses may be applied simultaneously to different portions of the one or more target skin areas. The pulses may be applied in patterns controlled by a controller to avoid or minimize simultaneous delivery of different pulse types to the same target skin area, or to target skin areas separated by small distances (e.g., 0.5-5 mm and/or distances less than one, two, or three times the beam diameter used).

In one example, the vascular treatment pulses and pigment treatment pulses may have parameters as described in connection with FIG. 20. In another example, the remodeling or collagen treatment pulses may have a fluence of between 0.2 J/cm2 to 5 J/cm2; a pulse duration of between 0.5 to 50 ns; a beam diameter or spot size of between 0.1 to 0.5 mm; and/or a wavelength of 1064 nm. Any of these parameters may be changed and/or modified when moving from one treatment spot to another, as described in connection the discussion of the vascular and pigment treatment pulses in FIG. 20, and as shown in legend 1338 of FIG. 13. For example, a first remodeling/collagen treatment pulse 1326 may have a fluence of 1.1 J/cm2; a pulse duration of 50 ns; a spot diameter of 0.1 mm; and a wavelength of 1064 nm, while a second remodeling treatment pulse may have a fluence of 1.0 J/cm2; a pulse duration of 45 ns; a spot diameter of 0.2 mm; and a wavelength of 1064 nm. In another embodiment, the second collagen treatment pulse may have a fluence of 1.1 J/cm2; a pulse duration of 45 ns; a spot diameter of 0.1 mm; and a wavelength of 1064 nm. Further, a third collagen treatment pulse may have a fluence of 5.0 J/cm2; a pulse duration of 0.5 ns; a spot diameter of 0.5 mm; and a wavelength of 1064 nm. In various embodiments, the spot or beam diameter may comprise a diameter within the range of 0.01-5.0 mm.

Figure 22:
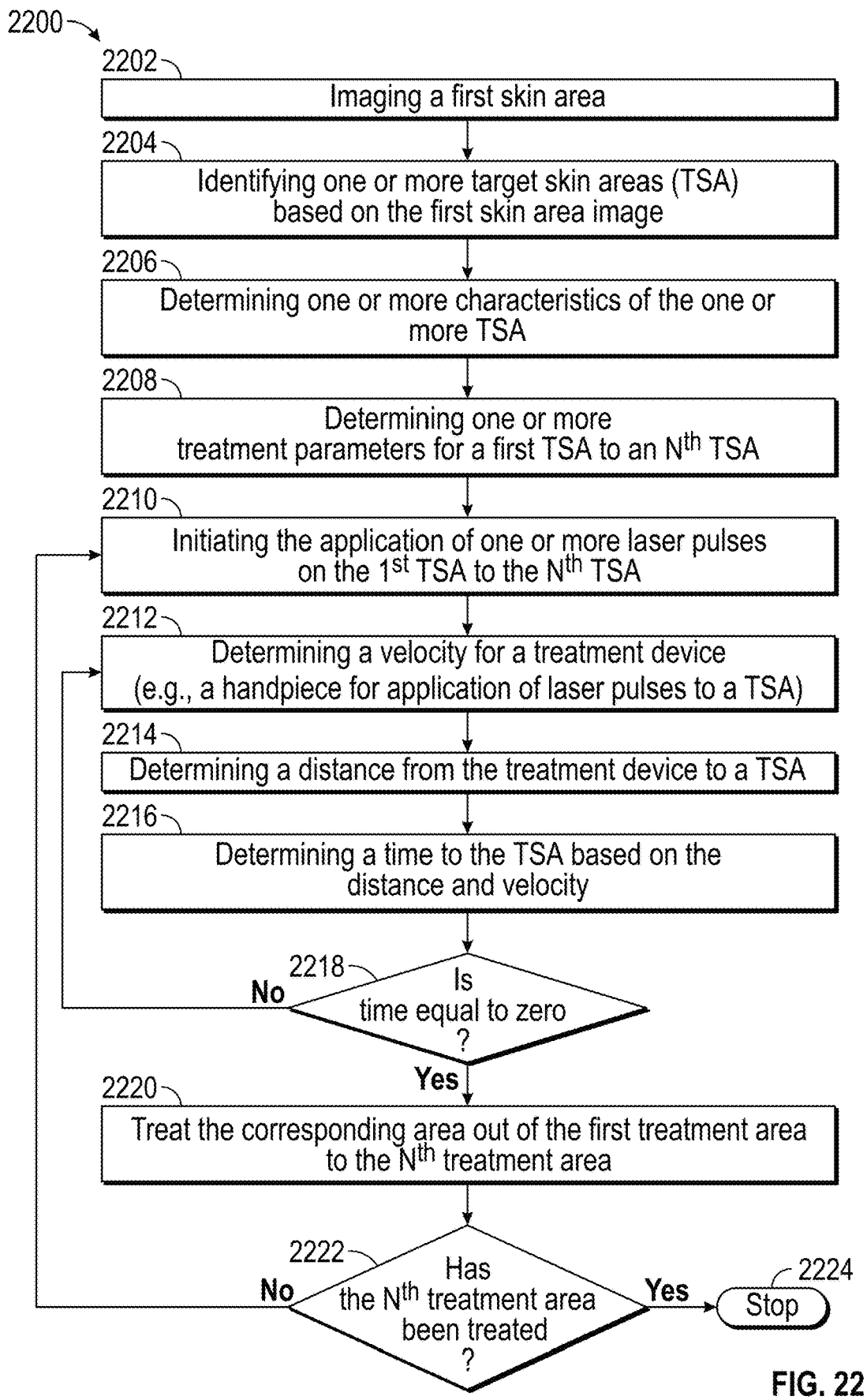
FIG. 22 is a treatment flow chart, according to one embodiment.

In FIG. 22, a treatment flow chart of a method of treating one or more target skin areas is shown, according to one embodiment. Each and every combination of steps shown in the treatment flow chart is disclosed herein, and each and every step may be combined with any of the other steps and/or may be optional. A treatment method 2200 may include imaging a first skin area via one or more imaging devices such as a digital or analog camera (step 2202). The treatment method 2200 may include identifying one or more target skin areas based on the image of the first skin (step 2204). The treatment method 2200 may include determining one or more characteristics of the one or more target skin areas (step 2206). The treatment method 2200 may include determining one or more treatment parameters for a first target skin area to an Nth target skin area (step 2208). The treatment method 2200 may include initiating the application of one or more laser pulses (e.g., pulses having the parameters determined in step 2208) to the first target skin area to an Nth treatment area (step 2210). The treatment method 2200 may include determining a velocity for a treatment device (step 2212). In one embodiment, the treatment device may comprise a handpiece such as handheld device 200 described in connection with FIG. 2 above. The treatment method 2200 may include determining one or more distances to one or more target skin areas based on a current position of the treatment device (step 2214). The treatment method 2200 may include determining one or more times to the one or more target skin areas based on the one or more distances to the one or more treatment areas and the velocity of the treatment device (step 2216). The treatment method 2200 may include determining via one or more processors whether a time value to the one or more target skin areas determined in step 2216 is equal to zero (step 2218). If the time value is not equal to zero, then the treatment method 2200 may comprise returning to step 2212, and if the time value is equal to zero, then the treatment method 2200 may comprise applying laser pulses to one or more of the first target skin area to the Nth target skin area (step 2220). The treatment method 2200 may include determining via one or more processors whether the Nth target skin area has been treated (step 2222). If the Nth target skin area has not been treated, then the treatment method 2200 may comprise returning to step 2210. If the Nth target skin area has been treated, then the treatment method 2200 may stop (step 2224).

In one example, a treatment plan with various treatment parameters is determined for three treatment areas by accomplishing steps 2202; 2204; 2206; and 2208 with one or more methods disclosed in this document. The system, device, and/or method may initiate the application of one or more laser pulses to the first target skin area, the second target skin area, and the third target skin area. The system, device, and/or method may determine one or more movement characteristics of the treatment device. For example, the system, device, and/or method may determine a velocity, an acceleration, and/or an angle of movement for the treatment device. The system, device, and/or method may determine that at time X the treatment device will reach the first skin area in 1 second, the treatment device will reach the second target skin area in 4 seconds, and the treatment device will reach the third target skin area in 5 seconds. The system, device, and/or method may continue to calculate the time of arrival for each target skin area until a time to each target skin area reaches a zero value. Once the time reaches a zero value, application of laser pulses to the corresponding target skin area is initiated.

Figure 23:
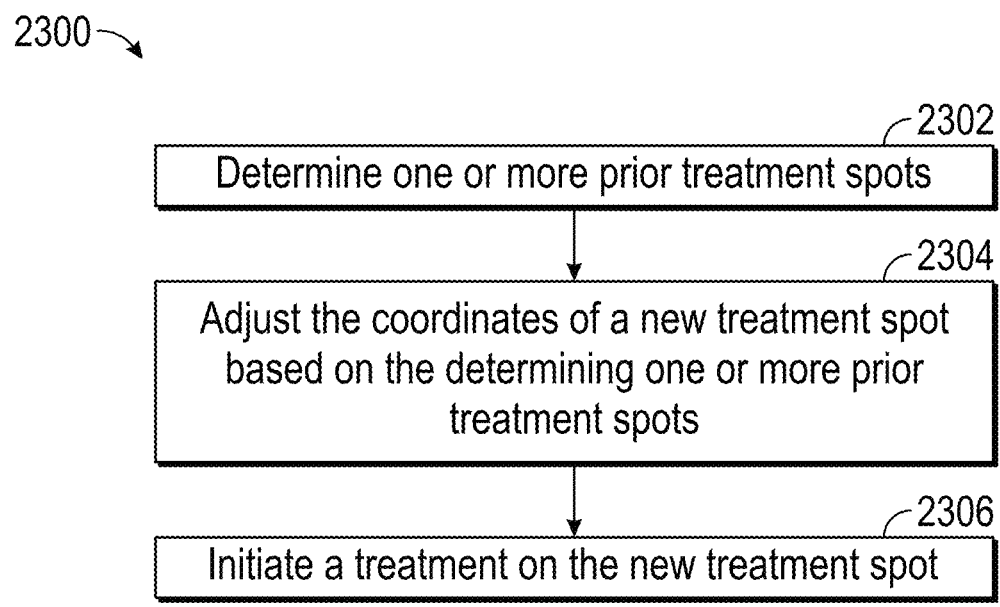
FIG. 23 is a treatment flow chart, according to one embodiment.

FIG. 23 shows a treatment method. A treatment method 2300 may include determining one or more prior treatment spots (step 2302). The treatment method 2300 may include adjusting the coordinates of a new treatment spot based on the determining one or more prior treatment spots (step 2304). The treatment method 2300 may include initiating a treatment on the new treatment spot (step 2306). For example, the system, device, and/or method may determine a previous treatment spot at a position Y. The system, device, and/or method may determine that an upcoming treatment spot at a position X is too close to a previous treatment spot at a position Y. Based on this information, the system, device, and/or method may adjust and/or move the upcoming treatment spot to a position of X'. In another example, the system, device, and/or method may determine that a previous treatment spot was at a position Z. The system, device, and/or method may determine that the upcoming treatment spot at a position of X' is too close to the previous treatment spot at position Z. Based on this information, the system, device, and/or method may adjust and/or move the upcoming treatment spot to a position of X". The system, device, and/or method may utilize one or more previous treatment spots (and any interactions with each other—previous treatment spot one interacts with previous treatment spot two, etc.) to determine where the upcoming treatment spot should be located and/or any modifications of treatment parameters.

In various embodiments, the present disclosure relates to the subject matter of the following numbered paragraphs.

101. A method of treating a skin of a patient with therapeutic laser light, the method comprising:
 a) imaging a first skin area of the patient to obtain at least a first image;
 b) processing the at least a first image of the first skin area with at least one processor to identify within the first skin area:
  1) one or more target skin areas, and
  2) a non-target skin area;
 c) generating a treatment map of the first skin area based on the identified one or more target skin areas and the non-target skin area; and
 d) treating at least a portion of the one or more target skin areas with therapeutic laser light based on the generated treatment map, while leaving the non-target area substantially untreated with the therapeutic laser light.

102. The method of 101, wherein treating at least a portion of the one or more target skin areas comprises:
 1) providing a therapeutic laser light source capable of generating pulsed therapeutic laser light;
 2) providing at least one movable optical element optically coupled to the therapeutic laser light source for receiving and directing the pulsed therapeutic laser light to a desired portion of the one or more target skin areas;
 3) providing at least one controller for controlling the movable optical element to direct the pulsed therapeutic laser light to the desired portion of the one or more target skin areas;
 4) generating pulsed therapeutic laser light using the therapeutic laser light source;
 5) controlling the movable optical element using the controller to direct one or more therapeutic laser light pulses to a first desired portion of a selected one of the one or more target skin areas;
 6) moving the movable optical element using the controller to direct one or more therapeutic laser light pulses to a desired portion of the selected one of the target skin areas that is different from the first desired portion; and
 7) repeating step 6 one or more times until a desired fraction of the selected one of the one or more target skin area has been treated with therapeutic laser light pulses.

103. The method of 102, further comprising:
 8) repeating steps 5-7 one or more times, wherein each repetition of step 5 comprises applying one or more therapeutic laser light pulses to a different selected one of the one or more target skin areas.

104. The method of 101, wherein imaging the first skin area comprises obtaining at least one of an image under ultraviolet lighting, an image under infrared lighting, and an image under visual lighting.

105. The method of 101, wherein processing the at least a first image to identify at least one of the one or more target skin areas comprises identifying one or more target skin areas as areas having at least one of a different skin color and a different skin pigmentation compared to the non-target skin area.

106. The method of 101, wherein generating a treatment map of the one or more target skin areas comprises generating a map identifying the geographic location and boundary of each of the one or more target skin areas within the first skin area.

107. The method of 102, wherein steps (5)-(7) are performed automatically to direct the generated pulsed therapeutic laser light to the desired portions of the one or more target skin areas, while not directing the generated pulsed therapeutic laser light to the non-target skin area.

201. A system for treating a skin of a patient with therapeutic laser light, the system comprising:
 a) a therapeutic laser light source capable of generating pulsed therapeutic laser light;
 b) an applicator optically coupled to the therapeutic laser light source for receiving the pulsed therapeutic laser light from the therapeutic laser light source and directing the pulsed therapeutic laser light to the skin of the patient, the applicator comprising at least one movable optical element for directing the pulsed therapeutic laser light to a desired portion of the skin of the patient;
 c) at least one imaging unit capable of imaging a first skin area of a patient to obtain at least a first image of the first skin area; and
 d) a controller having one or more processors for:
  1) processing the at least a first image of the first skin area to identify within the first skin area:

A) one or more target skin areas, and

B) a non-target skin area;

2) generating a treatment map of the first skin area based on the identified one or more target skin areas and the non-target skin area;

3) controlling the movable optical element using the treatment map to direct the generated pulsed therapeutic laser light to a first desired portion of the one or more target skin areas;

4) moving the movable optical element to direct the generated pulsed therapeutic laser light to a second desired portion of the one or more target skin areas; and 5) repeating step 4 one or more times until the one or more target skin areas have been treated with the pulsed therapeutic laser light, while leaving the non-target skin areas substantially untreated.

301. A treatment device comprising:

an imaging device;

a camera;

a scanner;

a light source;

a laser device; and a processor configured to generate via the camera image data, the processor configured to determine one or more treatment areas, the processor configured to determine one or more characteristics of the one or more treatment areas, and the processor configured to determine one or more laser device parameters for the treatment of the determined one or more treatment areas based on the determined characteristics of the one or more treatment areas.

302. The treatment device of 301, wherein the light source is capable of emitting visible light.

303. The treatment device of 301, wherein the light source is capable of emitting ultraviolet (UV) light.

304. The treatment device of 301, wherein the light source capable of emitting near infrared (NIR) light.

305. The treatment device of 301, wherein the light source is a LED device.

306. The treatment device of 301, wherein the light source is selected from ambient light and an electrically powered light source.

400. A system for treating a skin of a patient with therapeutic laser light, the system comprising:

a) a controller configured to control a therapeutic laser source and an applicator;

b) the therapeutic laser light source configured to generate pulsed therapeutic laser light, the therapeutic laser light source configured to adjust one or more parameters of the generated pulsed therapeutic laser light; and c) the applicator optically coupled to the therapeutic laser light source configured to receive the pulsed therapeutic laser light from the therapeutic laser light source, the applicator configured to direct the pulsed therapeutic laser light to the skin of the patient, the applicator including one or more movable optical elements for directing the pulsed therapeutic laser light to a targeted portion of the skin of the patient.

401. The system of 400, wherein the controller is configured to determine via one or more processors one or more target skin areas.

402. The system of 401, wherein the controller is configured to determine via one or more processors at least one therapy procedure based on one or more characteristics of the one or more target skin areas.

403. The system of 402, wherein the one or more characteristics of the one or more target skin areas are at least one of a color, size, thickness, layers, and/or a shape of the area.

404. The system of 402, wherein a first therapy procedure includes a multi factorial confluent treatment.

405. The system of 404, wherein the multi factorial confluent treatment includes a first therapy treatment being completed on at least a first portion of one or more target skin areas and after the first therapy treatment is completed on the one or more target skin areas initiating a second therapy treatment on at least a second portion of the one or more target skin areas.

406. The system of 405, wherein at least a first spot size and a second spot size are utilized during the first therapy treatment and a third spot size is utilized during the second therapy treatment.

407. The system of 406, wherein the controller is configured to determine at least one of the dimensions of the first spot size, the dimensions of the second spot size, and the dimensions of the third spot size based on one or more characteristics of the one or more target skin areas.

408. The system of 402, wherein a second therapy procedure includes a multi factorial fractional treatment.

409. The system of 408, wherein the multi factorial fractional treatment includes at least a first treatment procedure for a first medical condition and a second treatment procedure for a second medical condition.

410. The system of 409, wherein the first treatment procedure utilizes a first spot size and the second treatment procedure utilizes a second spot size.

411. The system of claim 400, wherein the applicator is configured to adjust a size of the pulsed therapeutic light via one or more adjustable elements.

500. A system for treating a skin of a patient with therapeutic laser light, the system comprising:

a) a controller configured to control a therapeutic laser source and an applicator;

b) the therapeutic laser light source configured to generate pulsed therapeutic laser light, the therapeutic laser light source configured to adjust one or more parameters of the generated pulsed therapeutic laser light; and c) the applicator optically coupled to the therapeutic laser light source configured to receive the pulsed therapeutic laser light from the therapeutic laser light source, the applicator configured to direct the pulsed therapeutic laser light to the skin of the patient, the applicator including one or more movable optical elements for directing the pulsed therapeutic laser light to a portion of the skin of the patient.

501. The system of 500, wherein the controller is configured to determine via one or more processors one or more target skin areas.

502. The system of 501, wherein the controller is configured to determine via one or more processors one or more therapy procedures based on one or more characteristics of the one or more target skin areas.

503. The system of 502, wherein the one or more characteristics of the one or more target skin areas are at least one of a color, size, thickness, layers, and/or a shape of the area.

504. The system of 502, wherein a first therapy procedure includes a multi factorial confluent treatment.

505. The system of 504, wherein the multi factorial confluent treatment includes a first therapy treatment being completed on at least a first portion of one or more target skin areas during a first pass of a first pulsed therapeutic laser light and a second therapy treatment on at least a second portion of the one or more target skin areas during a second pass of a second pulsed therapeutic laser light.

506. The system of 505, wherein a first spatial treatment procedure is utilized during the first therapy treatment and a second spatial treatment procedure is utilized during the second therapy treatment.

507. The system of 502, wherein a second therapy procedure includes a multi factorial fractional treatment.

508. The system of 507, wherein the multi factorial fractional treatment includes at least a first treatment procedure for a first medical condition and a second treatment procedure for a second medical condition.

509. The system of 508, wherein the first treatment procedure utilizes a first pulse duration and the second treatment procedure utilizes a second pulse duration.

510. The system of 508, wherein the first treatment procedure occurs concurrently with the second treatment procedure.

511. The system of 508, wherein a delay period is utilized between the first treatment procedure and the second treatment procedure.

600. A system for treating a skin of a patient with therapeutic laser light, the system comprising:
   a) a controller configured to control a therapeutic laser source and an applicator;
   b) the therapeutic laser light source configured to generate pulsed therapeutic laser light, the therapeutic laser light source configured to adjust one or more parameters of the generated pulsed therapeutic laser light;
   c) the applicator optically coupled to the therapeutic laser light source configured to receive the pulsed therapeutic laser light from the therapeutic laser light source, the applicator configured to direct the pulsed therapeutic laser light to the skin of the patient, the applicator including one or more movable optical elements for directing the pulsed therapeutic laser light to a targeted portion of the skin of the patient; and
   d) an imaging device configured to provide imaging data for one or more treatment areas to the controller, the controller configured to determine a velocity of the applicator via a sensor, the controller configured to determine one or more distances to the one or more treatment areas based on the imaging data for the one or more treatment areas, the controller configured to determine one or more times to the one or more treatment areas based on the velocity of the applicator and the one or more distances to the one or more treatment areas, and the controller configured to initiate one or more treatments for the one or more treatment areas based on one or more times reaching a zero value.

601. The system of 600, wherein the one or more treatments are part of a multiple passing treatment procedure.

602. The system of 601, wherein the multiple passing treatment procedure provides treatment layers during multiple passes of the applicator.

603. The system of 602, wherein the treatment layers are located on the one or more treatment areas.

604. The system of 603, wherein the treatment layers have a targeted value of between 25 percent to 35 percent density.

605. The system of 602, wherein the treatment layers have a targeted value of 30 percent density.

606. The system of 600, wherein the one or more treatments includes a multi factorial confluent treatment.

607. The system of 606, wherein the multi factorial confluent treatment includes a first therapy treatment being completed on at least a first portion of the one or more treatment areas during a first pass of a first pulsed therapeutic laser light and a second therapy treatment on at least a second portion of the one or more treatment areas during a second pass of a second pulsed therapeutic laser light.

In one embodiment, a method of treating a skin of a patient with therapeutic laser light may include: imaging a first skin area of the patient to obtain at least a first image; processing the at least a first image of the first skin area with at least one processor to identify within the first skin area: one or more target skin areas and a non-target skin area; generating a treatment map of the first skin area based on the identified one or more target skin areas and the non-target skin area; and/or treating at least a portion of the one or more target skin areas with therapeutic laser light based on the generated treatment map, while leaving the non-target area untreated with the therapeutic laser light.

In another example, the treating at least a portion of the one or more target skin areas may include: providing (and/or using) a therapeutic laser light source capable of generating pulsed therapeutic laser light; providing (and/or using) at least one movable optical element optically coupled to the therapeutic laser light source for receiving and directing the pulsed therapeutic laser light to a desired portion of the one or more target skin areas; providing (and/or using) at least one controller for controlling the movable optical element to direct the pulsed therapeutic laser light to the desired portion of the one or more target skin areas; generating pulsed therapeutic laser light using the therapeutic laser light source; controlling the movable optical element using the controller to direct one or more therapeutic laser light pulses to a first desired portion of a selected one of the one or more target skin areas; moving the movable optical element using the controller to direct one or more therapeutic laser light pulses to a desired portion of the selected one of the target skin areas that is different from the first desired portion; and/or repeating the moving the movable optical element using the controller to direct one or more therapeutic laser light pulses to a desired portion of the selected one of the target skin areas that is different from the first desired portion step one or more times until a desired fraction of the selected one of the one or more target skin area has been treated with therapeutic laser light pulses.

In another example, the method may include: repeating generating pulsed therapeutic laser light using the therapeutic laser light source; controlling the movable optical element using the controller to direct one or more therapeutic laser light pulses to a first desired portion of a selected one of the one or more target skin areas; moving the movable optical element using the controller to direct one or more therapeutic laser light pulses to a desired portion of the selected one of the target skin areas that is different from the first desired portion steps one or more times, wherein each repetition of generating pulsed therapeutic laser light using the therapeutic laser light sources step includes applying one or more therapeutic laser light pulses to a different selected one of the one or more target skin areas.

In another example, the imaging the first skin area includes obtaining at least one of an image under ultraviolet lighting, an image under infrared lighting, and an image under visual lighting. In another example, the processing the at least a first image to identify at least one of the one or more target skin areas includes identifying one or more target skin areas as areas having at least one of a different skin color and a different skin pigmentation compared to the non-target skin area. In another example, the generating a treatment map of the one or more target skin areas includes generating a map identifying the geographic location and boundary of each of the one or more target skin areas within the first skin area.

In another example, generating pulsed therapeutic laser light using the therapeutic laser light source; controlling the movable optical element using the controller to direct one or more therapeutic laser light pulses to a first desired portion of a selected one of the one or more target skin areas; moving the movable optical element using the controller to direct one or more therapeutic laser light pulses to a desired portion of the selected one of the target skin areas that is different from the first desired portion steps are performed automatically to direct the generated pulsed therapeutic laser light to the desired portions of the one or more target skin areas, while not directing the generated pulsed therapeutic laser light to the non-target skin area.

In another embodiment, a system for treating a skin of a patient with therapeutic laser light may include: a therapeutic laser light source capable of generating pulsed therapeutic laser light; an applicator optically coupled to the therapeutic laser light source for receiving the pulsed therapeutic laser light from the therapeutic laser light source and directing the pulsed therapeutic laser light to the skin of the patient, the applicator comprising at least one movable optical element for directing the pulsed therapeutic laser light to a desired portion of the skin of the patient; at least one imaging unit capable of imaging a first skin area of a patient to obtain at least a first image of the first skin area; and/or a controller having one or more processors for: processing the at least a first image of the first skin area to identify within the first skin area: one or more target skin areas, and a non-target skin area; generating a treatment map of the first skin area based on the identified one or more target skin areas and the non-target skin area; controlling the movable optical element using the treatment map to direct the generated pulsed therapeutic laser light to a first desired portion of the one or more target skin areas; moving the movable optical element to direct the generated pulsed therapeutic laser light to a second desired portion of the one or more target skin areas; and/or repeating moving the movable optical element to direct the generated pulsed therapeutic laser light to a second desired portion of the one or more target skin areas step one or more times until the one or more target skin areas have been treated with the pulsed therapeutic laser light, while leaving the non-target skin areas substantially untreated.

In another embodiment, a treatment device includes: an imaging device; a camera; a scanner; a light source; a laser device; and/or a processor which generates via the camera image data, the processor determines one or more treatment areas, the processor determines one or more characteristics of the one or more treatment areas, and the processor determines one or more laser device parameters for the treatment of the determined one or more treatment areas based on the determined characteristics of the one or more treatment areas.

In another example, the light source is capable of emitting visible light. In another example, the light source is capable of emitting ultraviolet (UV) light. In another example, the light source capable of emitting near infrared (NIR) light. In another example, the light source is a LED device. In another example, the light source is selected from ambient light and an electrically powered light source. In another example, any of the light sources disclosed in this document may be utilized and/or combined in any manner.

In another embodiment, a system for treating a skin of a patient with therapeutic laser light include: a controller controls a therapeutic laser source and an applicator; the therapeutic laser light source generates pulsed therapeutic laser light, the therapeutic laser light source adjusts one or more parameters of the generated pulsed therapeutic laser light; and/or the applicator optically coupled to the therapeutic laser light source receives the pulsed therapeutic laser light from the therapeutic laser light source, the applicator directs the pulsed therapeutic laser light to the skin of the patient, the applicator including one or more movable optical elements for directing the pulsed therapeutic laser light to a targeted portion of the skin of the patient, the applicator adjusts a size of the pulsed therapeutic light via one or more adjustable elements.

In another example, the controller determines via one or more processors one or more target skin areas. In another example, the controller determines via one or more processors at least one therapy procedure based on one or more characteristics of the one or more target skin areas. In another example, the one or more characteristics of the one or more target skin areas are at least one of a color, size, thickness, layers, and/or a shape of the area. In another example, a first therapy procedure includes a multi factorial confluent treatment. In another example, the multi factorial confluent treatment includes a first therapy treatment being completed on at least a first portion of one or more target skin areas and after the first therapy treatment is completed on the one or more target skin areas initiating a second therapy treatment on at least a second portion of the one or more target skin areas. In another example, at least a first spot size and a second spot size are utilized during the first therapy treatment and a third spot size is utilized during the second therapy treatment. In another example, the controller determines at least one of the dimensions of the first spot size, the dimensions of the second spot size, and the dimensions of the third spot size based on one or more characteristics of the one or more target skin areas. In another example, a second therapy procedure includes a multi factorial fractional treatment. In another example, the multi factorial fractional treatment includes at least a first treatment procedure for a first medical condition and a second treatment procedure for a second medical condition. In another example, the first treatment procedure utilizes a first spot size and the second treatment procedure utilizes a second spot size.

In another embodiment, a system for treating a skin of a patient with therapeutic laser light includes: a controller configured to control a therapeutic laser source and an applicator; the therapeutic laser light source configured to generate pulsed therapeutic laser light, the therapeutic laser light source configured to adjust one or more parameters of the generated pulsed therapeutic laser light; and/or the applicator optically coupled to the therapeutic laser light source configured to receive the pulsed therapeutic laser light from the therapeutic laser light source, the applicator configured to direct the pulsed therapeutic laser light to the skin of the patient, the applicator including one or more movable optical elements for directing the pulsed therapeutic laser light to a portion of the skin of the patient.

In another example, the controller determines via one or more processors one or more target skin areas. In another example, the controller determines via one or more processors one or more therapy procedures based on one or more characteristics of the one or more target skin areas. In another example, the one or more characteristics of the one or more target skin areas are at least one of a color, size, thickness, layers, and/or a shape of the area. In another example, a first therapy procedure includes a multi factorial confluent treatment. In another example, the multi factorial confluent treatment includes a first therapy treatment being completed on at least a first portion of one or more target skin areas during a first pass of a first pulsed therapeutic laser light and a second therapy treatment on at least a second portion of the one or more target skin areas during a second pass of a second pulsed therapeutic laser light. In another example, a first spatial treatment procedure is utilized during the first therapy treatment and a second spatial treatment procedure is utilized during the second therapy treatment. In another example, a second therapy procedure includes a multi factorial fractional treatment. In another example, the multi factorial fractional treatment includes at least a first treatment procedure for a first medical condition and a second treatment procedure for a second medical condition. In another example, the first treatment procedure utilizes a first pulse duration and the second treatment procedure utilizes a second pulse duration. In another example, the first treatment procedure occurs concurrently with the second treatment procedure. In another example, a delay period is utilized between the first treatment procedure and the second treatment procedure.

In another embodiment, a system for treating a skin of a patient with therapeutic laser light includes: a controller configured to control a therapeutic laser source and an applicator; the therapeutic laser light source configured to generate pulsed therapeutic laser light, the therapeutic laser light source configured to adjust one or more parameters of the generated pulsed therapeutic laser light; the applicator optically coupled to the therapeutic laser light source configured to receive the pulsed therapeutic laser light from the therapeutic laser light source, the applicator configured to direct the pulsed therapeutic laser light to the skin of the patient, the applicator including one or more movable optical elements for directing the pulsed therapeutic laser light to a targeted portion of the skin of the patient; and/or an imaging device configured to provide imaging data for one or more treatment areas to the controller, the controller configured to determine a velocity of the applicator via a sensor, the controller configured to determine one or more distances to the one or more treatment areas based on the imaging data for the one or more treatment areas, the controller configured to determine one or more times to the one or more treatment areas based on the velocity of the applicator and the one or more distances to the one or more treatment areas, and the controller configured to initiate one or more treatments for the one or more treatment areas based on one or more times reaching a zero value.

In another example, the one or more treatments are part of a multiple passing treatment procedure. In another example, the multiple passing treatment procedure provides treatment layers during multiple passes of the applicator. In another example, the treatment layers are located on the one or more treatment areas. In another example, the treatment layers have a targeted value of between 25 percent to 35 percent density. In another example, the treatment layers have a targeted value of 30 percent density. In another example, the treatment layers have a targeted value of between 5 percent to 45 percent density. In another example, the one or more treatments include a multi factorial confluent treatment. In another example, the multi factorial confluent treatment includes a first therapy treatment being completed on at least a first portion of the one or more treatment areas during a first pass of a first pulsed therapeutic laser light and a second therapy treatment on at least a second portion of the one or more treatment areas during a second pass of a second pulsed therapeutic laser light.

As used herein, the term "mobile device" refers to a device that may from time to time have a position that changes. Such changes in position may comprise of changes to direction, distance, and/or orientation. In particular examples, a mobile device may comprise of a cellular telephone, wireless communication device, user equipment, laptop computer, other personal communication system ("PCS") device, personal digital assistant ("PDA"), personal audio device ("PAD"), portable navigational device, or other portable communication device. A mobile device may also comprise of a processor or computing platform adapted to perform functions controlled by machine-readable instructions.

The methods and/or methodologies described herein may be implemented by various means depending upon applications according to particular examples. For example, such methodologies may be implemented in hardware, firmware, software, or combinations thereof. In a hardware implementation, for example, a processing unit may be implemented within one or more application specific integrated circuits ("ASICs"), digital signal processors ("DSPs"), digital signal processing devices ("DSPDs"), programmable logic devices ("PLDs"), field programmable gate arrays ("FPGAs"), processors, controllers, micro-controllers, microprocessors, electronic devices, other devices units designed to perform the functions described herein, or combinations thereof.

Some portions of the detailed description included herein are presented in terms of algorithms or symbolic representations of operations on binary digital signals stored within a memory of a specific apparatus or a special purpose computing device or platform. In the context of this particular specification, the term specific apparatus or the like includes a general purpose computer once it is programmed to perform particular operations pursuant to instructions from program software. Algorithmic descriptions or symbolic representations are examples of techniques used by those of ordinary skill in the arts to convey the substance of their work to others skilled in the art. An algorithm is considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals, or the like. It should be understood, however, that all of these or similar terms are to be associated with appropriate physical quantities and are merely convenient labels. Unless specifically stated otherwise, as apparent from the discussion herein, it is appreciated that throughout this specification discussions utilizing terms such as "processing," "computing," "calculating," "determining" or the like refer to actions or processes of a specific apparatus, such as a special purpose computer or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

Reference throughout this specification to "one example," "an example," "embodiment," "a method", and/or "another example" should be considered to mean that the particular features, structures, or characteristics may be combined in one or more examples. Any combination of any element in this disclosure with any other element in this disclosure is hereby disclosed. For example, an element on page 3 can be combined with any element in this document (e.g., an element from page 6). In another example, any element from a first flow chart (FIG. 14) may be combined with any element in an Nth flow chart (FIG. 22) and/or any other element in any other flow chart and/or any other element in this document.

While there has been illustrated and described what are presently considered to be example features, it will be understood by those skilled in the art that various other modifications may be made, and equivalents may be substituted, without departing from the disclosed subject matter. Additionally, many modifications may be made to adapt a particular situation to the teachings of the disclosed subject matter without departing from the central concept described herein. Therefore, it is intended that the disclosed subject matter not be limited to the particular examples disclosed.

What is claimed is:

1. A system for treating skin tissue of a patient with therapeutic laser light, the system comprising:
   a) at least one imaging unit capable of imaging a first skin area of the patient to obtain at least a first image of the first skin area;
   b) an image processor for processing the at least a first image to identify at least one target skin area and at least one non-target skin area in the at least a first image based on at least one of shadings, colors, and shapes in the at least a first image;
   c) a therapeutic laser light source configured to generate therapeutic laser light pulses;
   d) an applicator optically coupled to the therapeutic laser light source, wherein the applicator is configured to receive the therapeutic laser light pulses from the therapeutic laser light source and to direct the therapeutic laser light pulses to a skin of the patient, the applicator further comprising a scanner to direct the therapeutic laser light pulses to the skin of the patient; and
   e) a controller for controlling the scanner to treat a skin area of the patient corresponding to at least a portion of the identified at least one target skin area by directing the therapeutic laser light pulses to the skin area of the patient corresponding to the identified at least one target skin area in the at least a first image, and not directing therapeutic laser light pulses to areas of the patient's skin corresponding to the identified at least one non-target skin area in the at least a first image.

2. The system of claim 1, further comprising:
   f) at least one light source capable of generating light in at least one of an ultraviolet wavelength range, a visible wavelength range, and an infrared wavelength range, wherein the at least one imaging unit is adapted to image the first skin area to obtain the at least a first image under at least one of an ultraviolet lighting condition, a visible lighting condition, and an infrared lighting condition.

3. The system of claim 1, wherein the at least one imaging unit comprises a camera configured to capture the at least a first image.

4. The system of claim 1, wherein the scanner comprises at least one movable optical element for directing the therapeutic laser light pulses to the skin area of the patient corresponding to the identified at least one target skin area in the at least a first image, and not directing therapeutic laser light pulses to areas of the patient's skin corresponding to the identified at least one non-target skin area in the at least a first image.

5. The system of claim 1, wherein the image processor is adapted to generate a treatment map based on the identified at least one target skin area and the identified at least one non-target skin area.

6. The system of claim 5, wherein the treatment map comprises a map of the geographic location of the identified at least one target skin area and the identified at least one non-target skin area within the first skin area.

7. The system of claim 5, wherein the treatment map comprises a map of the geographic location to which each of the therapeutic laser light pulses is to be applied in the identified at least one target skin area.

8. The system of claim 7, wherein the treatment map comprises a map of the geographic location to which therapeutic laser light pulses having a plurality of beam diameters are to be applied relative to the identified at least one target skin area.

9. The system of claim 5, wherein the treatment map comprises a pattern sequence for applying a plurality of therapeutic laser light pulses sequentially to geographic locations relative to the identified at least one target skin area, and wherein the controller controls the applicator by directing the each of the plurality of therapeutic laser light pulses sequentially according to the pattern sequence to geographic locations on the skin of the patient corresponding to the geographic locations in the treatment map.

10. The system of claim 9, wherein the pattern sequence defines a path for applying the sequence of pulses to the identified at least one target skin area to achieve at least one clinical objective selected from minimizing temperature buildup from a therapeutic laser light pulse into adjacent areas, ensuring heat dissipation from a therapeutic laser light pulse before delivering a different therapeutic laser light pulse to adjacent areas, minimizing treatment time, minimizing overtreatment of target skin area tissue, minimizing undertreatment of target skin area, maximizing treatment of target skin areas, minimizing treatment of non-target skin area, and avoiding treatment of non-target skin area.

11. The system of claim 5, wherein the treatment map comprises a timing sequence for applying each therapeutic laser light pulse to a geographic location relative to the identified at least one target skin area at a particular time relative to each other therapeutic laser pulse, and wherein the controller controls the applicator to direct each therapeutic laser light pulse according to the timing sequence to geographic locations on the skin of the patient corresponding to the geographic locations in the treatment map.

12. The system of claim 5, wherein the treatment map comprises an instruction set for applying the therapeutic laser light pulses to the identified at least one target skin area, wherein the instruction set comprises one or more parameters for each therapeutic light pulse selected from a timing parameter, a beam diameter, a fluence, a geographic location relative to the at least one target skin area, a pulse wavelength, and a pulse duration, and wherein the controller controls the applicator to direct each therapeutic light pulse according to the instruction set to geographic locations on the skin of the patent corresponding to the locations specified in the treatment map instruction set.

13. The system of claim 12, wherein the instruction set comprises a plurality of instruction sets to be applied in a series of passes to the target skin areas, wherein each instruction set in the plurality of instruction sets defines a plurality of pulses having the same pulse parameters to be delivered sequentially to portions of one or more of the target skin areas, the pulse parameters of each instruction set comprising at least one different pulse parameter from the pulse parameters of every other instruction set, wherein the controller delivers all of the pulses defined by an instruction set before delivering any pulse of another instruction set.

14. The system of claim 5, further comprising:
   f) a user interface comprising a display, wherein the user interface displays the treatment map on the display.

15. The system of claim 1, wherein the image processor is adapted to perform one or more image processing algorithms to perform at least one action selected from:
   1) Identifying a location of one or more skin lesions as a target skin area within the at least a first image;
   2) Identifying boundaries of the one or more skin lesions within the at least a first image;
   3) Identifying a location of the at least one non-target skin area within the at least a first image;
   4) Determining one or more treatment maps of the one or more target skin areas;
   5) Determining one or more therapeutic laser light pulse parameters for treating one or more target skin areas within the at least a first image, wherein the one or more therapeutic laser light pulse treatment parameters comprise at least one of a) a time of applying one or more therapeutic laser light pulses relative to the time of applying one or more other therapeutic laser light pulses, b) a beam diameter, c) a fluence, d) a geographic location for applying one or more therapeutic laser light pulses to at least one target skin area, e) a therapeutic laser light pulse wavelength, and f) a therapeutic laser light pulse duration;
   6) Classifying one or more portions of each of the at least one target skin areas within the at least a first image as a type of lesion based on at least one of shadings in the at least a first image, colors in the at least a first image, shapes in the at least a first image, and lighting conditions under which the at least a first image was captured;
   7) Determining one or more spatial coordinates for control of the scanner module in the applicator to enable the controller to direct the therapeutic laser light pulses to one or more geographic locations on the skin of the patient corresponding to the identified at least one target skin area in the at least a first image;
   8) Capturing one or more pre-treatment images as the at least a first image before the controller controls the applicator to direct any treatment pulses to any target skin area;
   9) Capturing one or more post-treatment images as at least one second image after delivery of one or more pulses to the at least one target skin area;
   10) Initiating a treatment analysis by comparing one or more pre-treatment images to one or more post-treatment images;
   11) Determining one or more recommended post-treatment procedures based on the treatment analysis; and
   12) Determining one or more further treatment procedures based on the treatment analysis.

16. The system of claim 15, wherein the system further comprises:
   f) a user interface comprising a display, wherein the user interface displays the treatment map on the display, and wherein the user interface is adapted to allow the user to perform one or more operations selected from:
      1) Confirming one or more target skin areas displayed in the treatment map;
      2) Rejecting one or more target skin areas displayed in the treatment map;
      3) Initiating a classification analysis of the identified at least one target skin area by the image processor, wherein the classification analysis comprises classifying one or more portions of each of the identified at least one target skin areas as a type of lesion based on at least one of shadings, colors, and shapes in the at least a first image;
      4) Modifying the treatment map generated by the image processor;
      5) Initiating a treatment of skin area of the patient corresponding to the identified at least one target skin area in the at least a first image;
      6) Initiating the capture of one or more pre-treatment images as the at least a first image using the imaging unit;
      7) Initiating the capture of one or more post-treatment images as at least one second image after delivery of one or more pulses to the at least one target skin area using the imaging unit;
      8) Initiating the treatment analysis of treatment results after the treatment of a skin area of the patient with therapeutic laser light pulses;
      9) Initiating the treatment analysis of the at least a first image to determine one or more recommended treatment procedures; and
      10) Initiating the treatment analysis of the one or more post-treatment images to determine at least one of recommended post-treatment procedures and recommended further treatment procedures.

17. The system of claim 1, wherein the controller controls the applicator to direct therapeutic laser light pulses to the skin area of the patient corresponding to the identified at least one target skin area at a rate of from 100-10,000 pulses per second.

18. The system of claim 1, wherein the controller controls the applicator to direct therapeutic laser light pulses to the skin area of the patient corresponding to the identified at least one target skin area via at least one of a) automatically without intervention by a user, and b) automatically without further intervention by the user after initiation of a delivery of the therapeutic laser light pulses by the user.

19. The system of claim 1, wherein the scanner comprises at least one movable mirror driven for directing the therapeutic laser light pulses to a skin area of the patient corresponding to a least a portion of a target skin area identified in the at least a first image, and not directing therapeutic laser light pulses to areas of the patient's skin corresponding to any non-target skin area identified in the at least a first image.

20. The system of claim 19, wherein the scanner comprises a movable mirror driven by one or more motors for controlling the position of the movable mirror in one or more axes, and wherein the controller controls the position of the movable mirror by controlling the operation of the one or more motors.

21. The system of claim 1, further comprising:
   f) a medical condition identifier module, wherein the image processor processes the at least a first image using the medical condition identifier module to identify at least one target skin area associated with a medical condition based on at least one of shadings, colors, and shapes in the at least a first image.

22. A system for treating skin tissue of a patient with therapeutic laser light, the system comprising:
   a) at least one imaging unit capable of imaging a first skin area of the patient to obtain at least a first image of a first skin area;

b) an image processor for processing the at least a first image to identify at least one target skin area and at least one non-target skin area in the at least a first image based on at least one of shadings, colors, and shapes in the at least a first image;
c) a therapeutic laser light source configured to generate therapeutic laser light pulses;
d) an applicator optically coupled to the therapeutic laser light source, wherein the applicator comprises a scanner having one or more movable optical elements to receive the therapeutic laser light pulses from the therapeutic laser light source and to direct the therapeutic laser light pulses to a skin of the patient; and
e) a controller for controlling the scanner to treat at least a portion of the at least one target skin area by directing the therapeutic laser light pulses to the at least one target skin area and not directing therapeutic laser light pulses to the at least one non-target skin area.

23. The system of claim 22, further comprising:
f) at least one light source capable of generating light in at least one of an ultraviolet wavelength range, a visible wavelength range, and an infrared wavelength range, wherein the at least one imaging unit is adapted to image the first skin area to obtain the at least a first image under at least one of an ultraviolet lighting condition, a visible lighting condition, and an infrared lighting condition.

24. The system of claim 22, wherein the image processor is adapted to perform one or more image processing algorithms to perform at least one action selected from:
1) Identifying a location of one or more skin lesions as the at least one target skin area within the at least a first image;
2) Identifying boundaries of the one or more skin lesions within the at least a first image;
3) Identifying a location of the at least one non-target skin area within the at least a first image;
4) Determining a treatment map for one or more target skin areas;
5) Determining one or more therapeutic laser light pulse parameters for treating one or more target skin areas, wherein the one or more therapeutic laser light pulse treatment parameters comprise at least one of a) a relative timing based on a comparison of a first time for applying one or more therapeutic laser light pulses to a second time of applying one or more other therapeutic laser light pulses, b) a beam diameter, c) a fluence, d) a geographic location for applying each of the therapeutic laser light pulses to the one or more target skin area, e) a therapeutic laser light pulse wavelength, and f) a therapeutic laser light pulse duration;
6) Classifying one or more portions of each of the at least one target skin areas within the at least a first image as a type of lesion based on at least one of shadings in the at least a first image, colors in the at least a first image, shapes in the at least a first image, and lighting conditions under which the at least a first image was captured;
7) Determining one or more spatial coordinates for control of a scanner module in the applicator to enable the controller to direct the therapeutic laser light pulses to the at least one target skin area on the skin of the patient;
8) Capturing one or more pre-treatment images as the at least a first image before the controller controls the applicator to direct any treatment pulses to any target skin area;
9) Capturing one or more post-treatment images as at least one second image after delivery of one or more pulses to the at least one target skin area;
10) Initiating a treatment analysis by comparing one or more pre-treatment images to one or more post-treatment images;
11) Determining one or more recommended post-treatment procedures based on the treatment analysis; and
12) Determining one or more further treatment procedures based on the treatment analysis.

25. The system of claim 24, wherein the system further comprises:
f) a user interface comprising a display, wherein the user interface displays the treatment map on the display, and wherein the user interface is adapted to allow the user to perform one or more operations selected from:
1) Confirming one or more target skin areas displayed in the treatment map;
2) Rejecting one or more target skin areas displayed in the treatment map;
3) Initiating a classification analysis of the identified at least one target skin area by the image processor, wherein the classification analysis comprises classifying one or more portions of each of the identified at least one target skin areas as a type of lesion based on at least one of shadings, colors, and shapes in the at least a first image;
4) Modifying the treatment map generated by the image processor;
5) initiating a treatment of a skin area of the patient corresponding to the identified at least one target skin area in the at least a first image;
6) Initiating the capture of one or more pre-treatment images as the at least a first image using the imaging unit;
7) Initiating the capture of one or more post-treatment images as at least one second image after delivery of one or more pulses to the at least one target skin area using the imaging unit;
8) Initiating the treatment analysis of treatment results after the treatment of a skin area of the patient with therapeutic laser light pulses;
9) Initiating the treatment analysis of the at least a first image to determine one or more recommended treatment procedures; and
10) Initiating the treatment analysis of the one or more post-treatment images to determine at least one of recommended post-treatment procedures and recommended further treatment procedures.

26. The system of claim 22, wherein the controller controls the applicator to direct therapeutic laser light pulses to the at least one target skin area at a rate of from 100-10,000 pulses per second.

27. The system of claim 22, wherein the controller controls the applicator to direct therapeutic laser light pulses to the at least one target skin area via at least one of a) automatically without intervention by a user, and b) automatically without further intervention by the user after initiation of a delivery of the therapeutic laser light pulses by the user.

28. The system of claim 22, wherein the controller is adapted to control the applicator to direct therapeutic laser light pulses having a beam diameter within the range of 0.01-5.0 mm to the at least one target skin area.

* * * * *